United States Patent
SelVakumar et al.

(10) Patent No.: US 6,861,587 B1
(45) Date of Patent: Mar. 1, 2005

(54) LOW STRESS DIE ATTACHMENT

(75) Inventors: Arjun SelVakumar, Bellaire, TX (US); James L. Marsh, San Antonio, TX (US); Howard D. Goldberg, Sugar Land, TX (US); Duli Yu, Sugar Land, TX (US); W. Marc Stalnaker, Sugar Land, TX (US)

(73) Assignee: Input/Output, Inc., Stafford, TX (US)

( * ) Notice: Subject to any disclaimer, the term of this patent is extended or adjusted under 35 U.S.C. 154(b) by 0 days.

(21) Appl. No.: 09/914,421

(22) PCT Filed: Mar. 15, 2000

(86) PCT No.: PCT/US00/06832

§ 371 (c)(1),
(2), (4) Date: Jan. 22, 2002

(87) PCT Pub. No.: WO00/56132

PCT Pub. Date: Sep. 21, 2000

Related U.S. Application Data

(60) Provisional application No. 60/125,076, filed on Mar. 17, 1999.

(51) Int. Cl.[7] .................................................. H05K 5/00
(52) U.S. Cl. ....................................... 174/52.1; 206/521
(58) Field of Search .......................... 174/52.1; 439/66; 206/521

(56) References Cited

U.S. PATENT DOCUMENTS

| | | | |
|---|---|---|---|
| 5,273,440 A | | 12/1993 | Ashman et al. |
| 5,285,559 A | * | 2/1994 | Thompson et al. ............ 29/841 |
| 5,375,469 A | | 12/1994 | Levy et al. ................ 73/517 B |
| 5,535,626 A | | 7/1996 | Bullis et al. .............. 73/514.32 |
| 5,540,593 A | | 7/1996 | Takahashi |
| 5,810,607 A | | 9/1998 | Shih et al. |
| 5,932,891 A | | 8/1999 | Higashi et al. |
| 5,993,248 A | | 11/1999 | Bethurum |

FOREIGN PATENT DOCUMENTS

| | | |
|---|---|---|
| GB | 2304903 | 3/1997 |
| JP | 11072534 | 9/1999 |

* cited by examiner

Primary Examiner—Hung V. Ngo
(74) Attorney, Agent, or Firm—Madan, Mossman & Sriram, P.C.

(57) ABSTRACT

A system for resiliently attaching a mass to a package. The system includes a mass, a housing, resilient couplings for resiliently attaching the mass to the housing, bumpers for slidingly supporting the mass, and electrical connections for electrically coupling the mass to the housing.

41 Claims, 64 Drawing Sheets

LOW STRESS DIE ATTACHMENT

This application claims the benefit of Provisional application Ser. No. 60/125,076 filed Mar. 17, 1999.

BACKGROUND OF THE INVENTION

The present disclosure relates generally to a method of attaching a mass to a package, and in particular to attaching a mass to a package in order to minimize stress.

In attaching a mass to a package, thermally induced contraction and expansion effects are created in the mass as well as other package stress effects. Elastomer or epoxy-based attach materials minimize thermally induced contraction and expansion effects but limit the shock withstanding of the mass and cannot facilitate vacuum sealing due to out gassing. Mechanical attachment processes minimize thermally induced contraction and expansion effects created in the mass, but are complex.

The present invention is directed at minimizing the thermally induced contraction and expansion stresses along with other stress effects in the mass and the housing, while providing good manufacturability and enabling a vacuum-sealing process.

SUMMARY OF THE INVENTION

An apparatus is provided that includes a package, a mass coupled to the package, and one or more resilient couplings for attaching the mass to the package.

A method of coupling a mass to a package is provided that includes resiliently attaching the mass to the package at one or more different locations.

BRIEF DESCRIPTION OF THE DRAWINGS

FIG. 5AA is a top view of an alternate embodiment of the sliding supports of the apparatus of FIG. 5X.

FIG. 5BB is a top view of an alternate embodiment of the sliding supports of the apparatus of FIG. 5X.

FIG. 6P is a top view of an alternate embodiment of the bond pad of the apparatus of FIG. 6A.

FIG. 6Q is a top view of an alternate embodiment of the bond pad of the apparatus of FIG. 6A.

FIG. 6R is a top view of an alternate embodiment of the bond pad of the apparatus of FIG. 6A.

FIG. 6S is a top view of an alternate embodiment of the bond pad of the apparatus of FIG. 6A.

FIG. 6T is a top view of an alternate embodiment of the first resilient coupling of the apparatus of FIG. 6A.

FIG. 6U is a detailed view of the alternate embodiment of the first resilient coupling of FIG. 6T.

FIG. 6V is a top view of an alternate embodiment of the second resilient coupling of the apparatus of FIG. 6A.

FIG. 6W is a detailed view of the alternate embodiment of the second resilient coupling of FIG. 6V.

FIG. 6X is a cross-sectional view illustrating an alternate embodiment of an apparatus for resiliently attaching a mass to a package.

FIG. 6Y is a top view of an embodiment of the sliding supports of the apparatus of FIG. 6X.

FIG. 6Z is a top view of an alternate embodiment of the sliding supports of the apparatus of FIG. 6X.

Figure 6A:
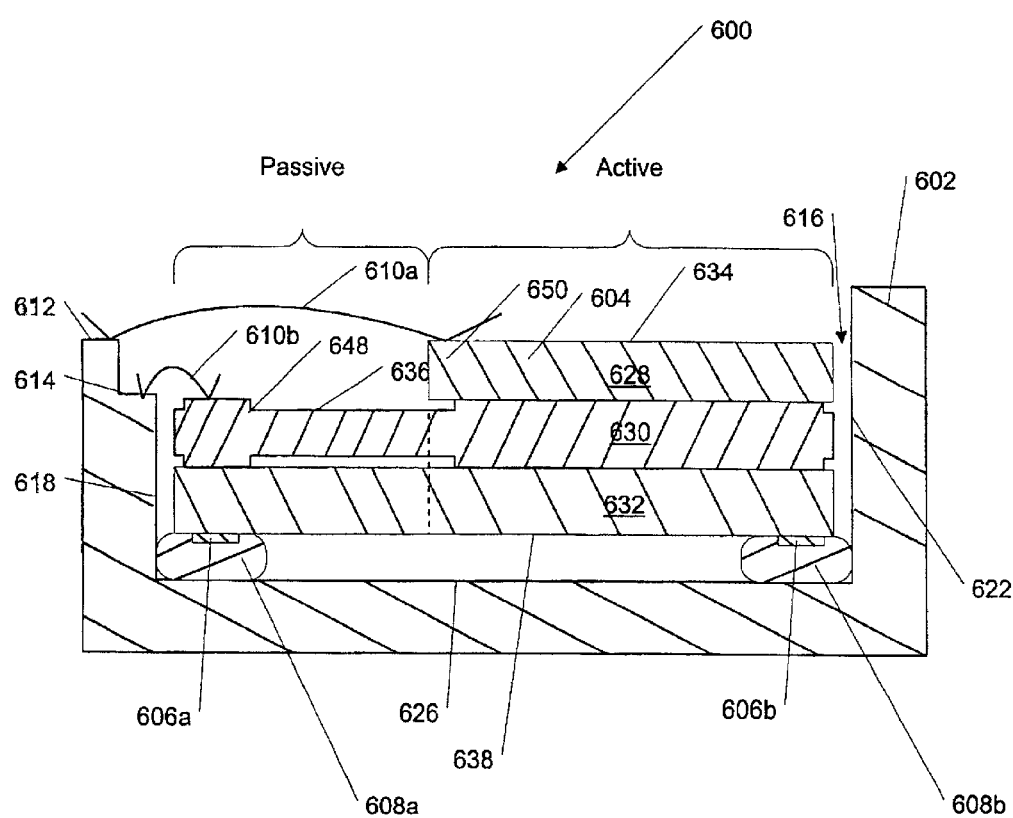
FIG. 6A is a cross-sectional view illustrating an embodiment of an apparatus for resiliently attaching a mass to a package.
Figure 6B:
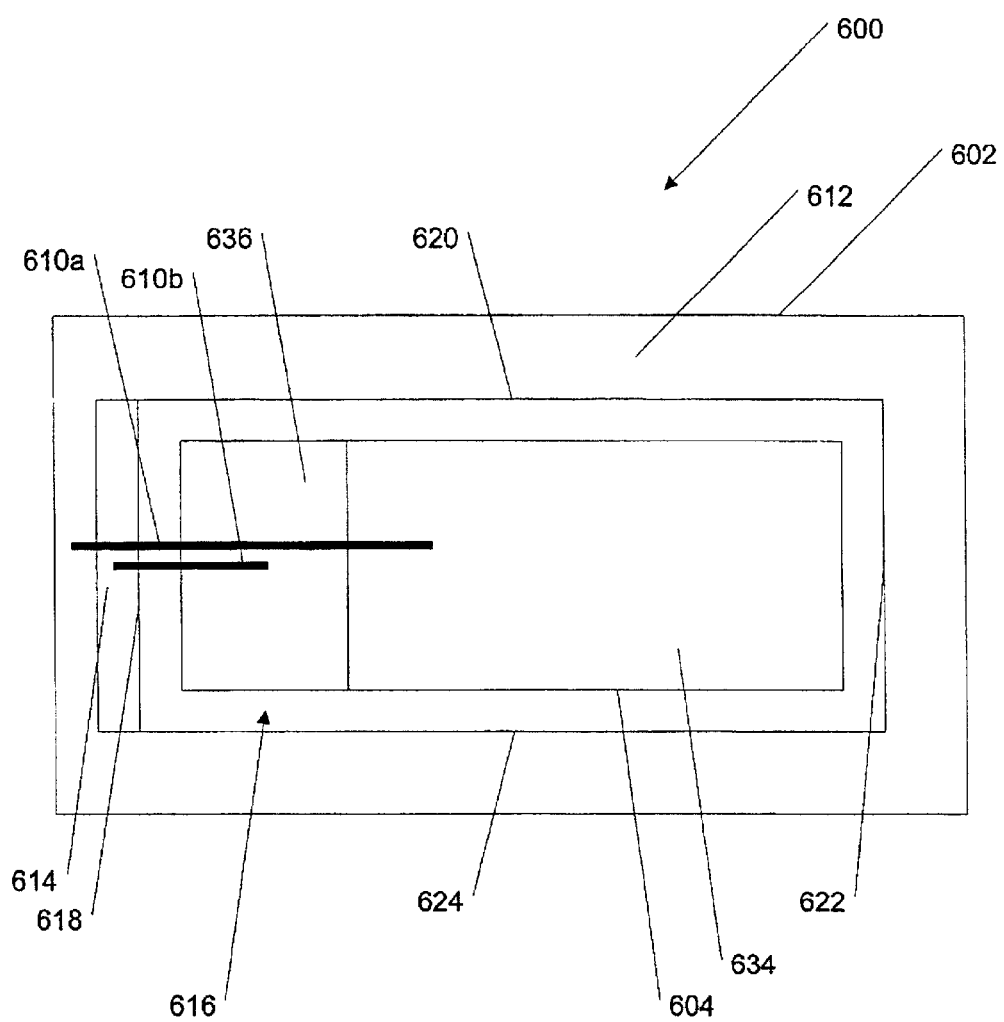
FIG. 6B is a top view of an embodiment of the apparatus of FIG. 6A.
Figure 6C:
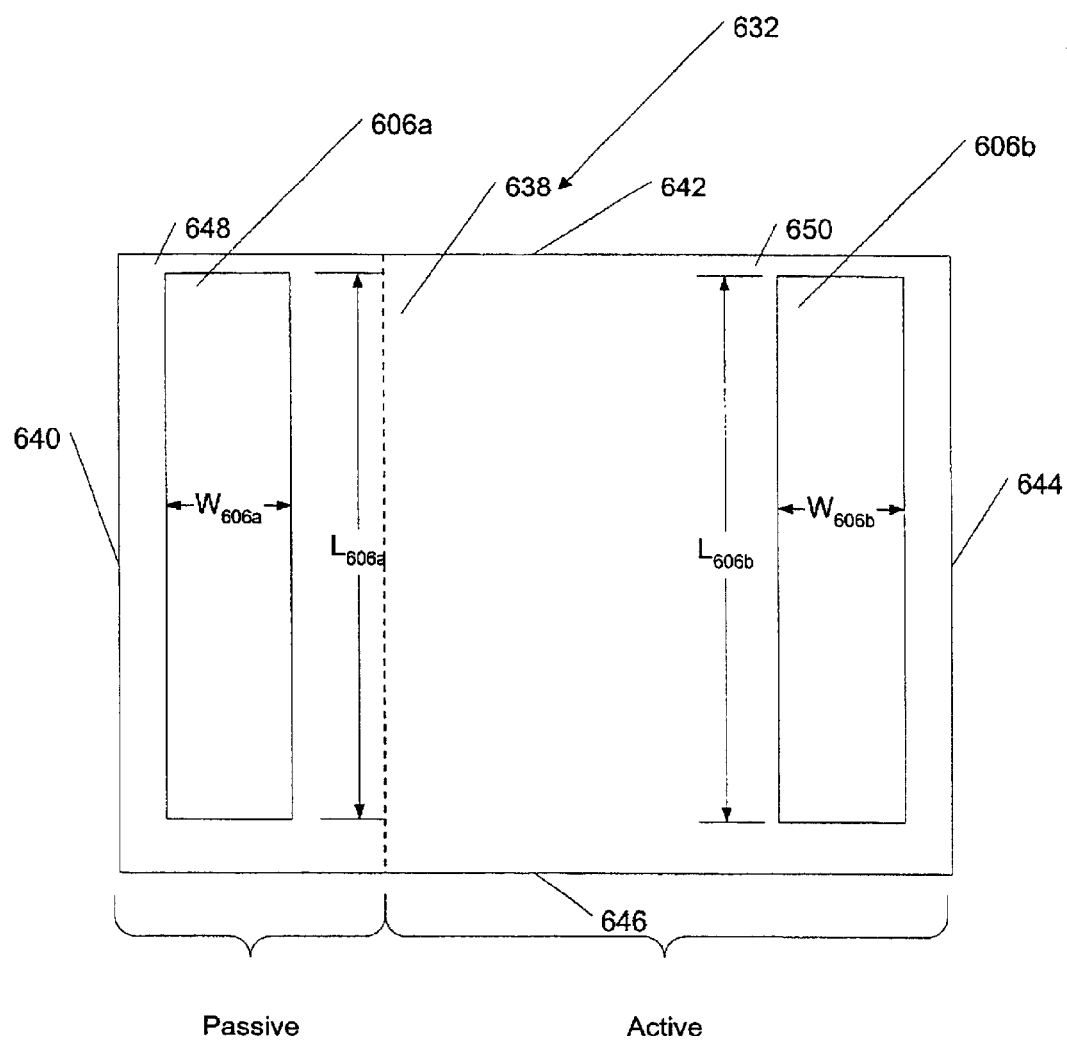
FIG. 6C is a bottom view of an embodiment of the mass of the apparatus of FIG. 6A.
Figure 6D:
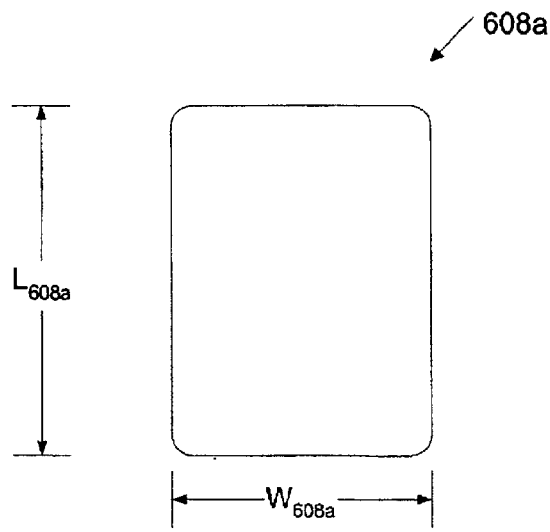
FIG. 6D is a top view of an embodiment of the first resilient coupling of the apparatus of FIG. 6A.
Figure 6E:
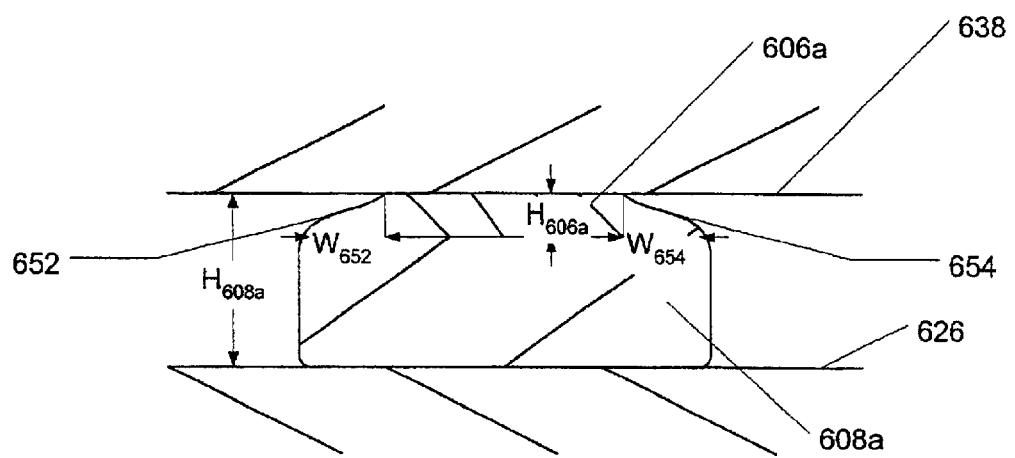
FIG. 6E is a detailed view of the embodiment of the first resilient coupling of FIG. 6D.
Figure 6F:
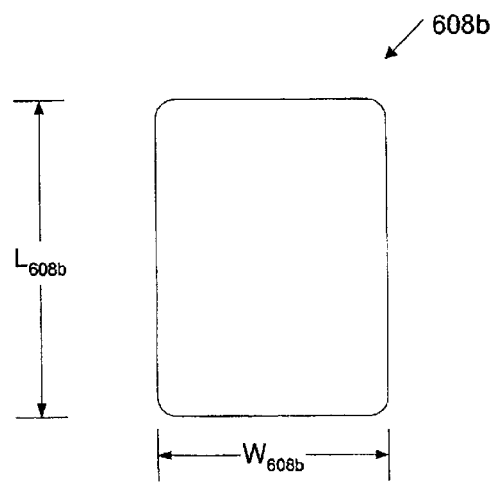
FIG. 6F is a top view of an embodiment of the second resilient coupling of the apparatus of FIG. 6A.
Figure 6G:
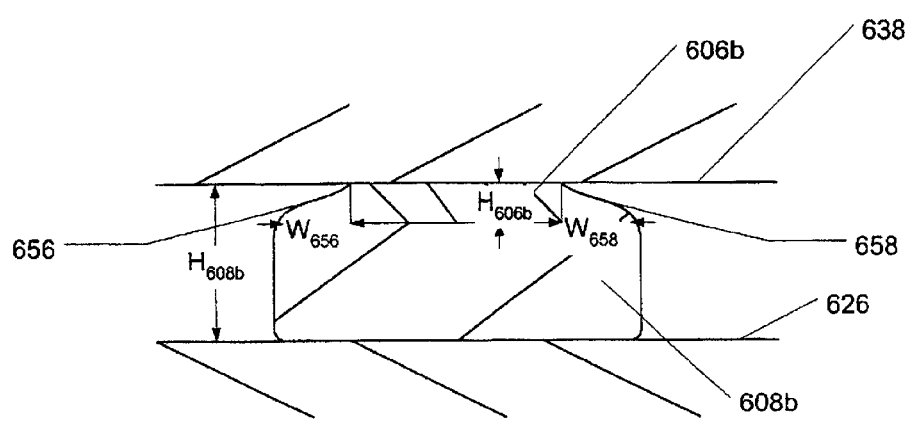
FIG. 6G is a detailed view of the embodiment of the second resilient coupling of FIG. 6F.
Figure 6H:
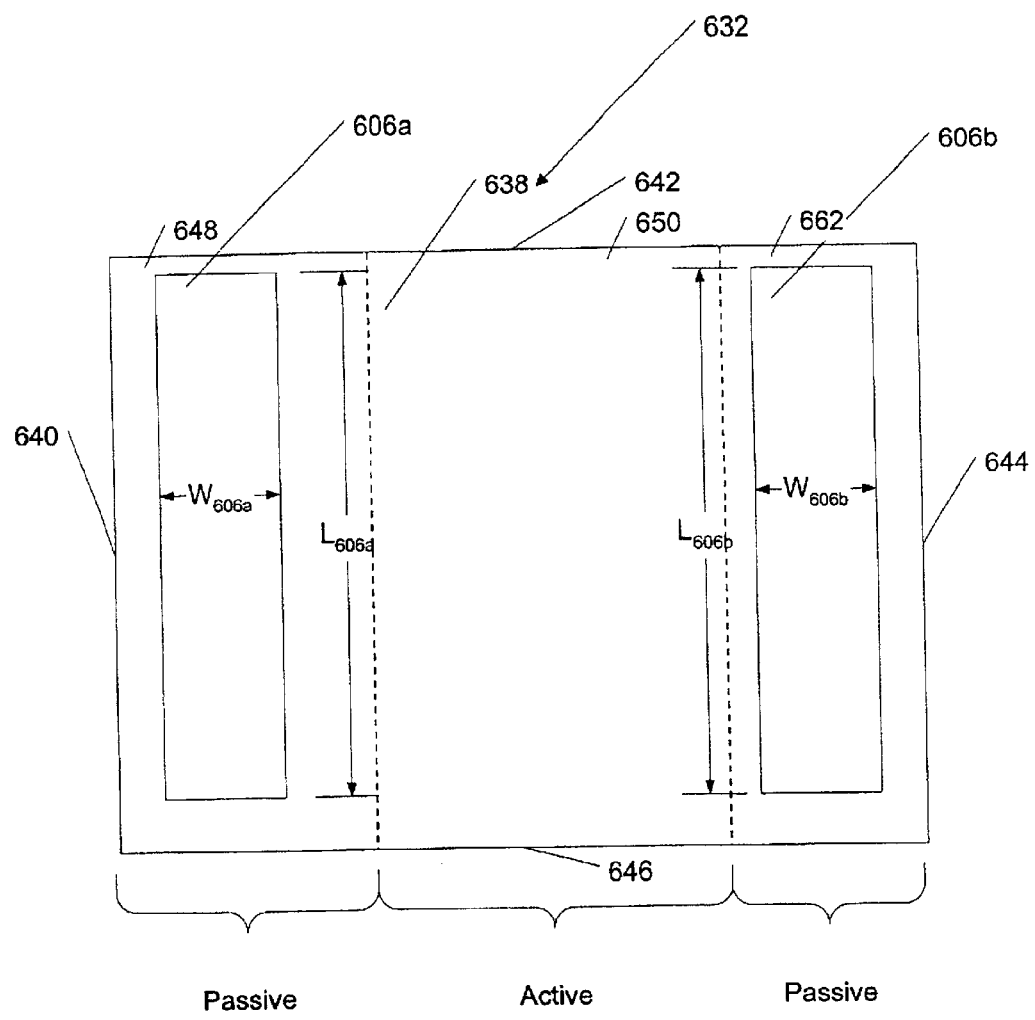
FIG. 6H is a bottom view of an alternate embodiment of the mass of the apparatus of FIG. 6A.
Figure 6J:
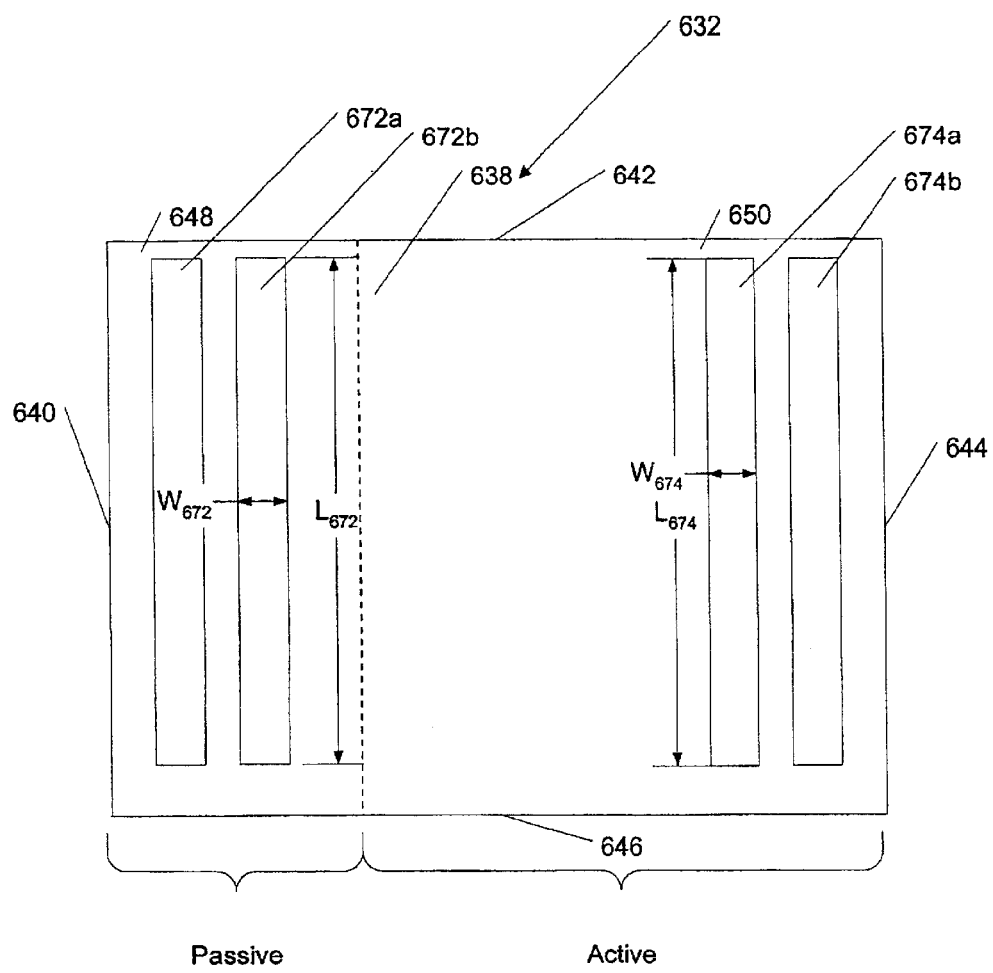
FIG. 6J is a bottom view of an alternate embodiment of the mass of the apparatus of FIG. 6A.
Figure 6K:
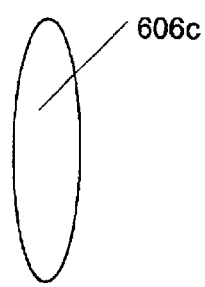
FIG. 6K is a top view of an alternate embodiment of the bond pad of the apparatus of FIG. 6A.
Figure 6L:
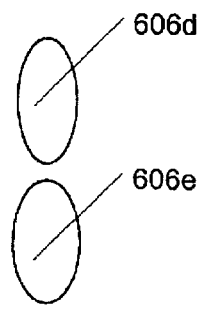
FIG. 6L is a top view of an alternate embodiment of the bond pad of the apparatus of FIG. 6A.
Figure 6M:
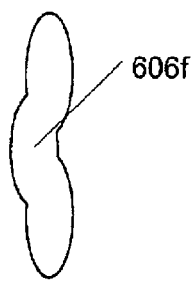
FIG. 6M is a top view of an alternate embodiment of the bond pad of the apparatus of FIG. 6A.
Figure 6N:
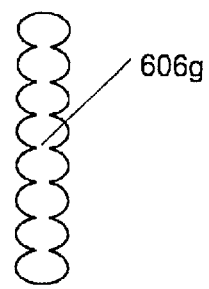
FIG. 6N is a top view of an alternate embodiment of the bond pad of the apparatus of FIG. 6A.
Figure 6P:
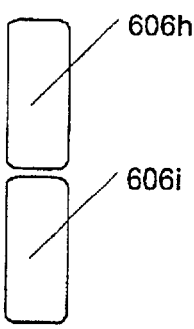
Figure 6Q:
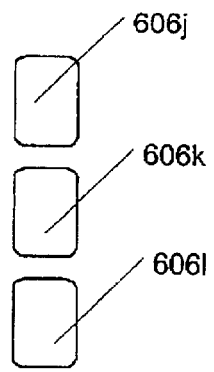
Figure 6R:
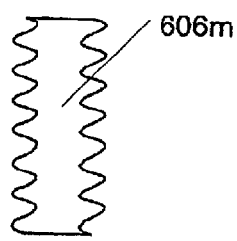
Figure 6S:
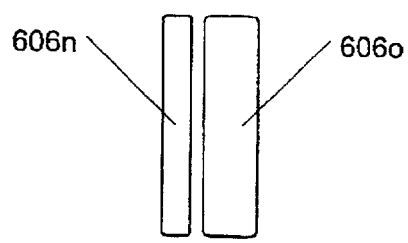
Figure 6T:
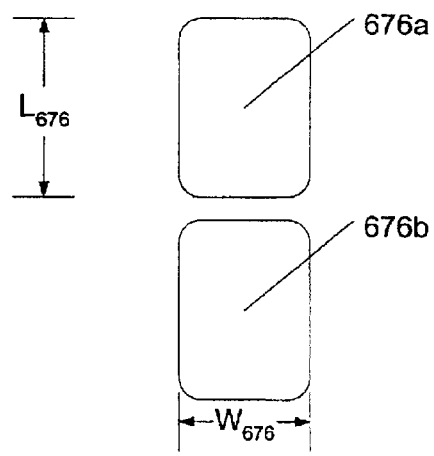
Figure 6U:
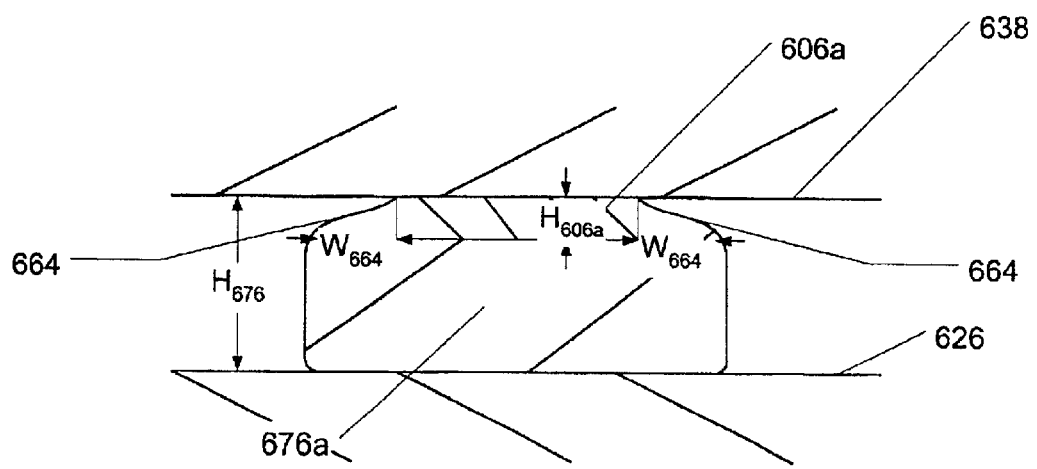
Figure 6V:
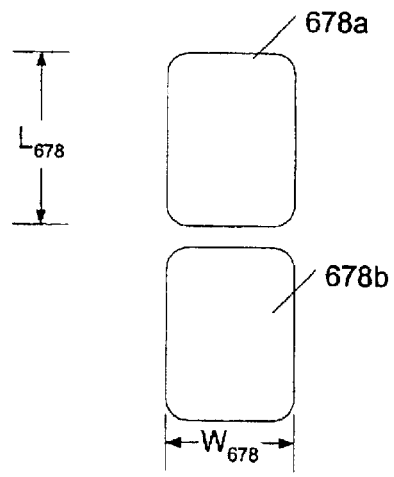
Figure 6W:
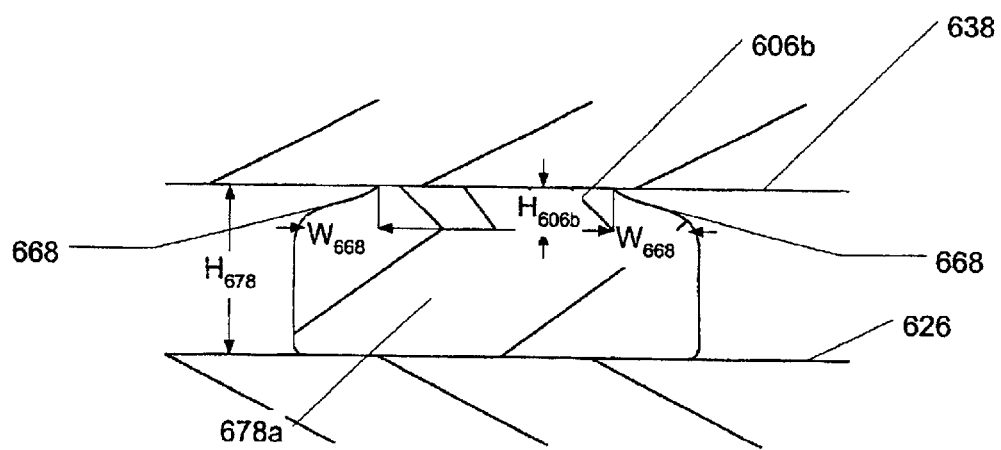
Figure 6X:
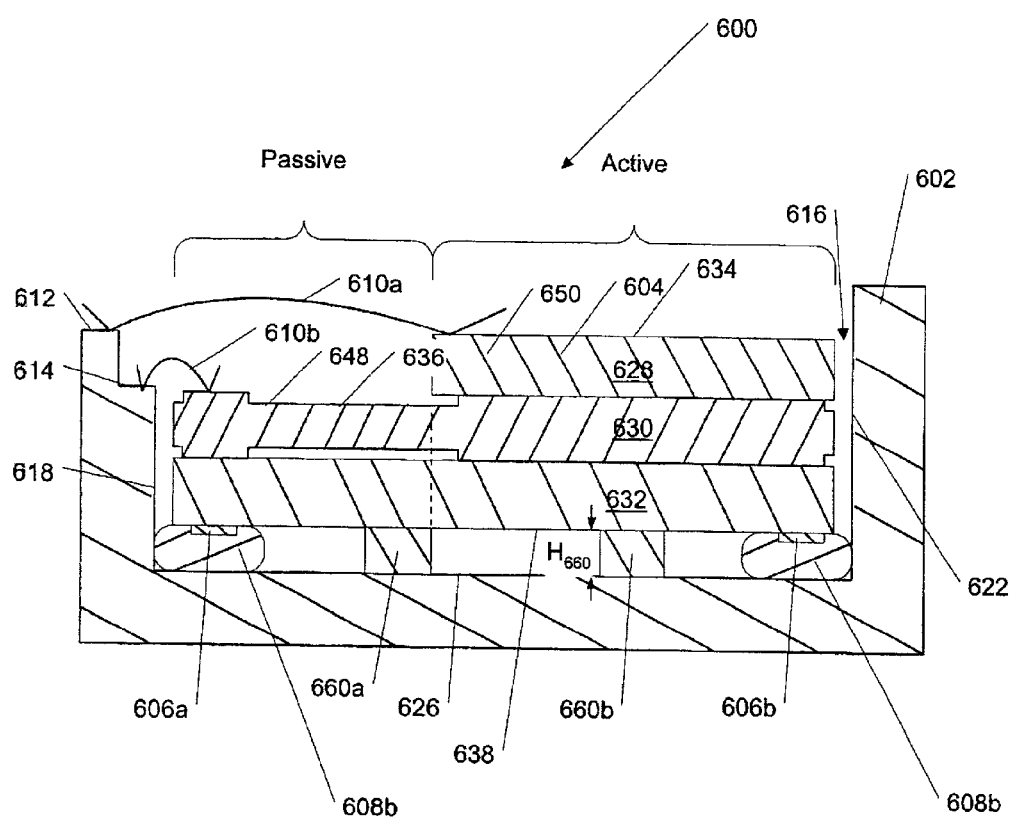
Figure 6Y:
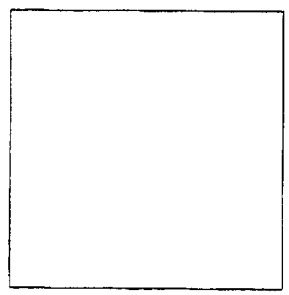
Figure 6Z:
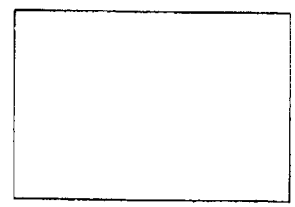
Figure 6A:
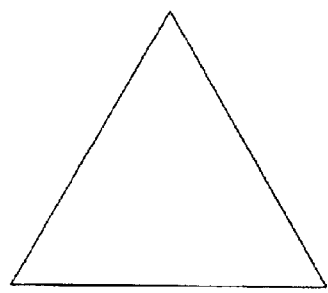
Figure 6B:
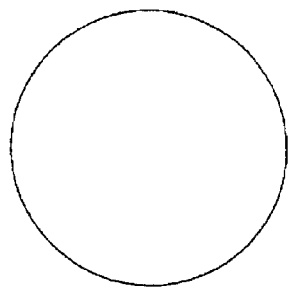

FIG. 6AA is a top view of an alternate embodiment of the sliding supports of the apparatus of FIG. 6X.

FIG. 6BB is a top view of an alternate embodiment of the sliding supports of the apparatus of FIG. 6X.

Figure 1A:
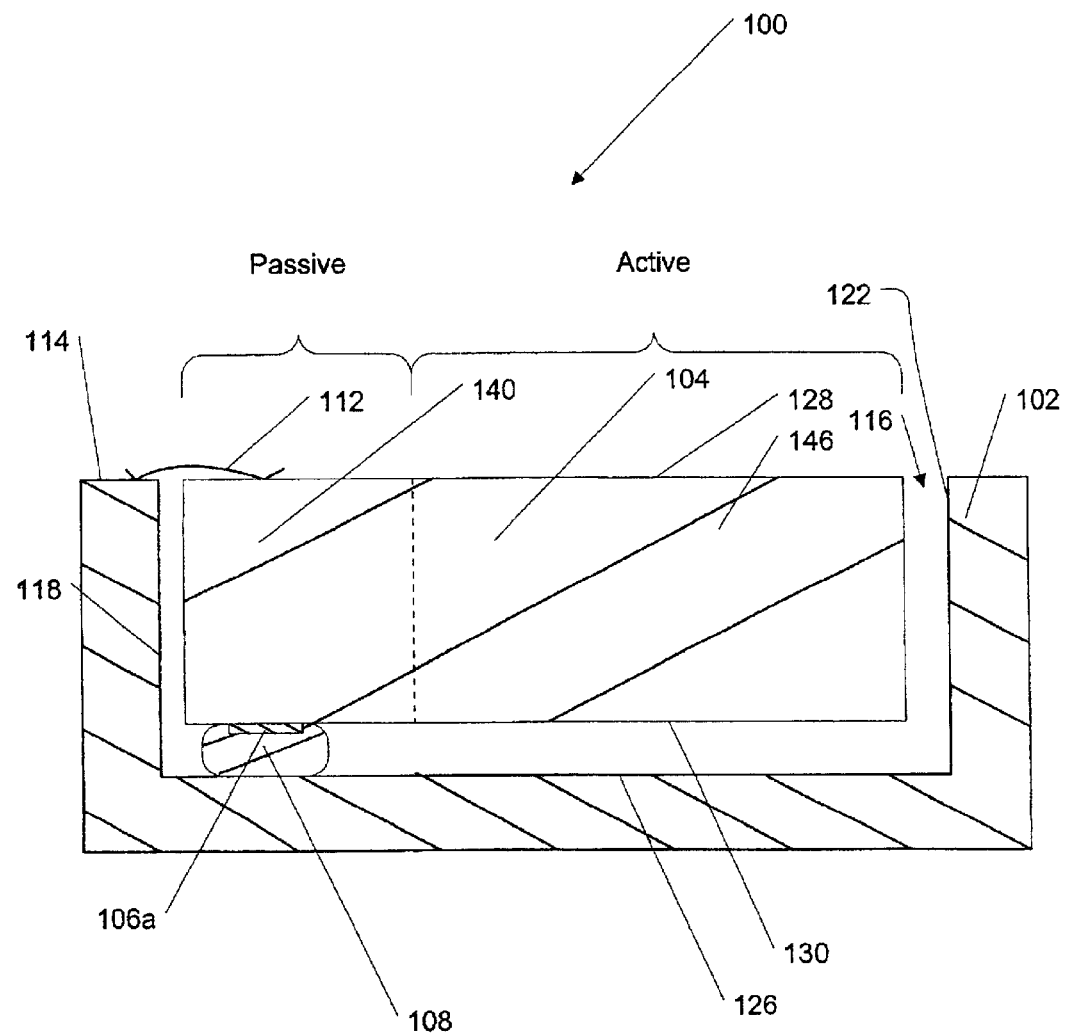
FIG. 1A is a cross-sectional view illustrating an embodiment of an apparatus for resiliently attaching a mass to a package.
Figure 1B:
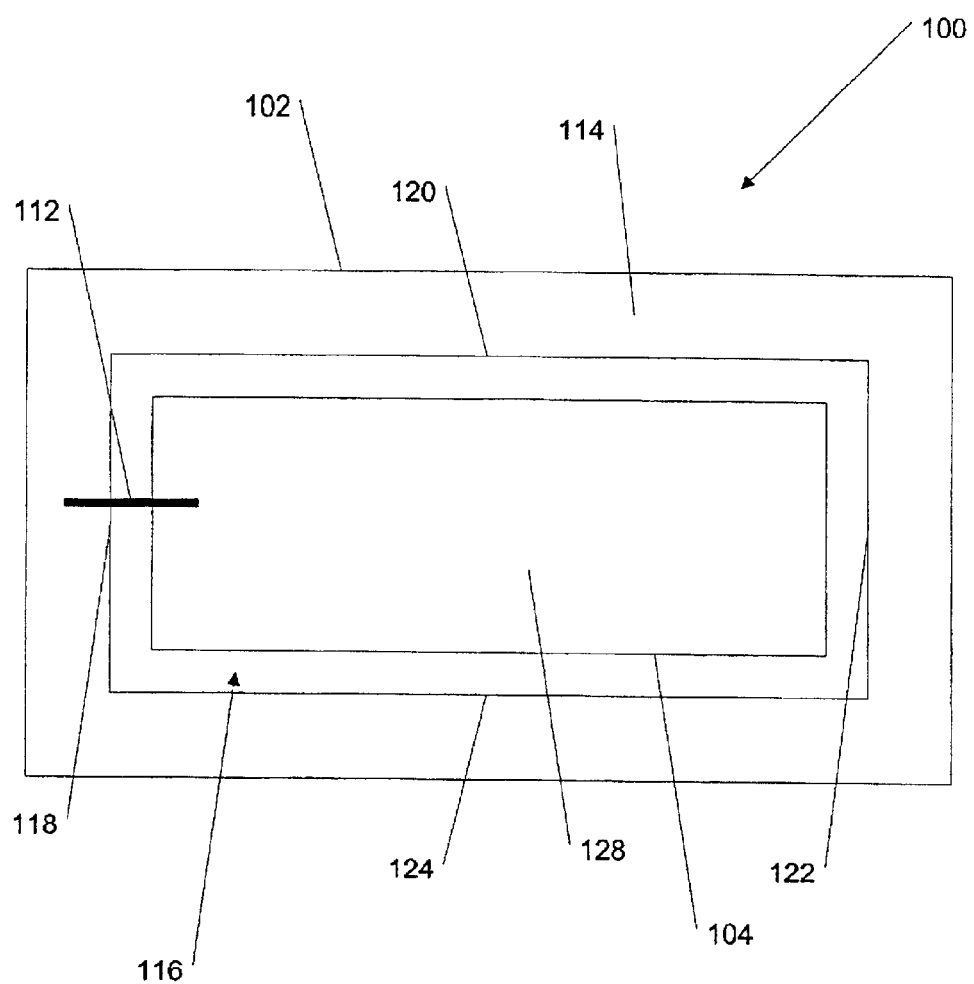
FIG. 1B is a top view of an embodiment of the apparatus of FIG. 1A.
Figure 1C:
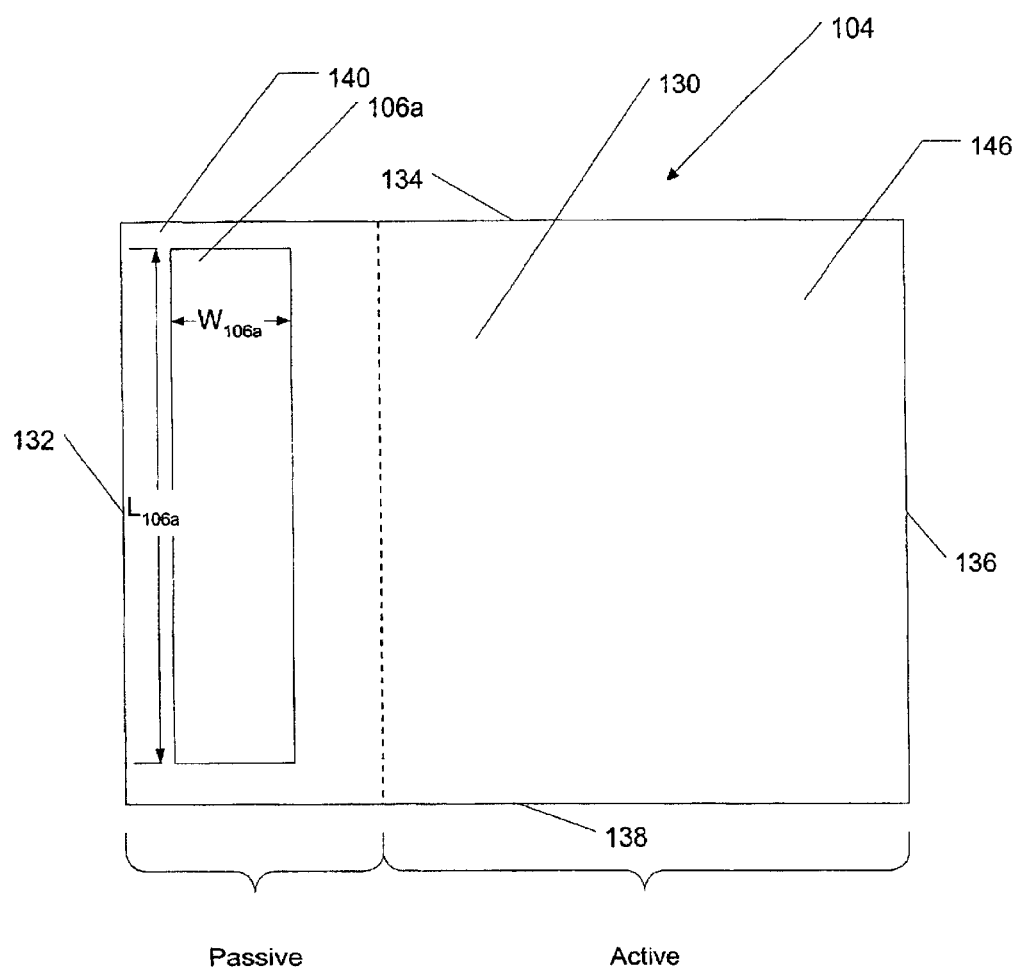
FIG. 1C is a bottom view of an embodiment of the mass of the apparatus of FIG. 1A.
Figure 1D:
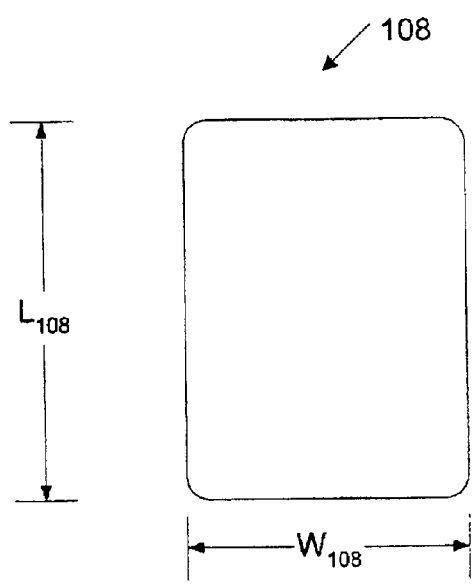
FIG. 1D is a top view of an embodiment of the resilient coupling of the apparatus of FIG. 1A.
Figure 1E:
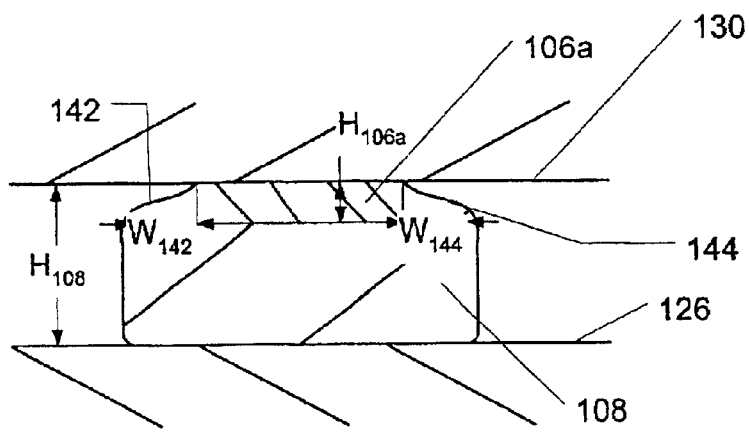
FIG. 1E is a detailed view of the embodiment of the resilient coupling of FIG. 1D.
Figure 7A:
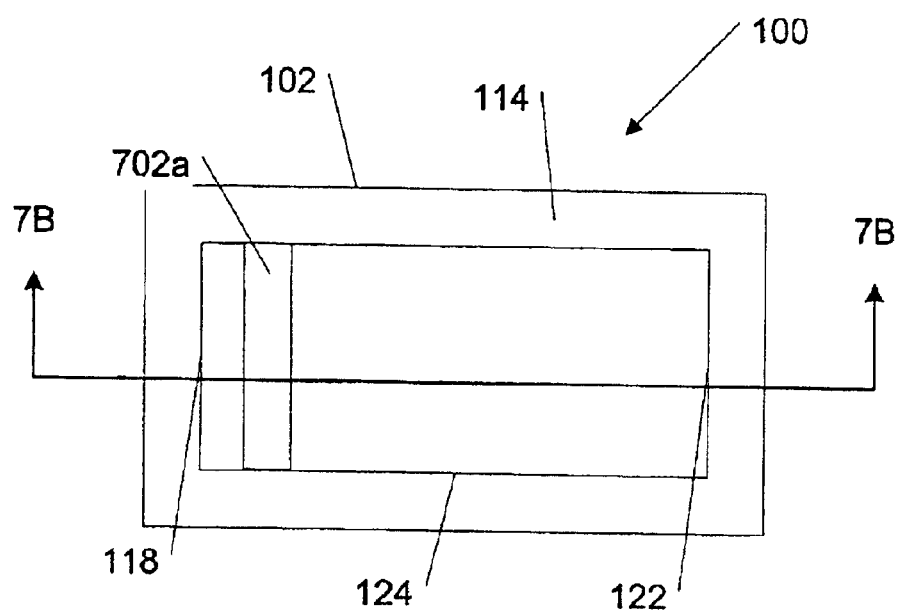

FIG. 7A is a top view of an alternate embodiment of the apparatus of FIG. 1A.

Figure 7B:
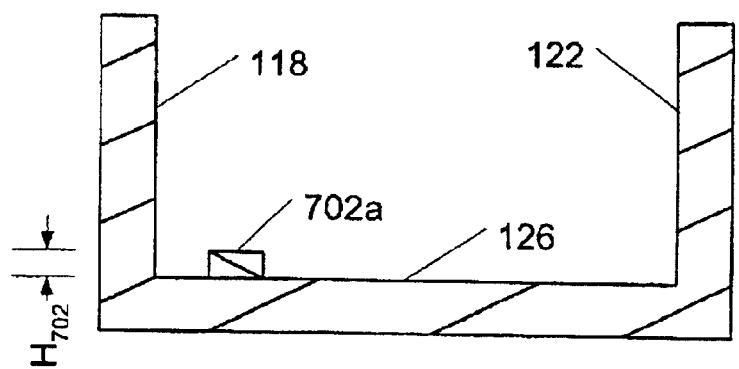

FIG. 7B is a cross-sectional view of an alternate embodiment of the apparatus of FIG. 1A.

Figure 7C:
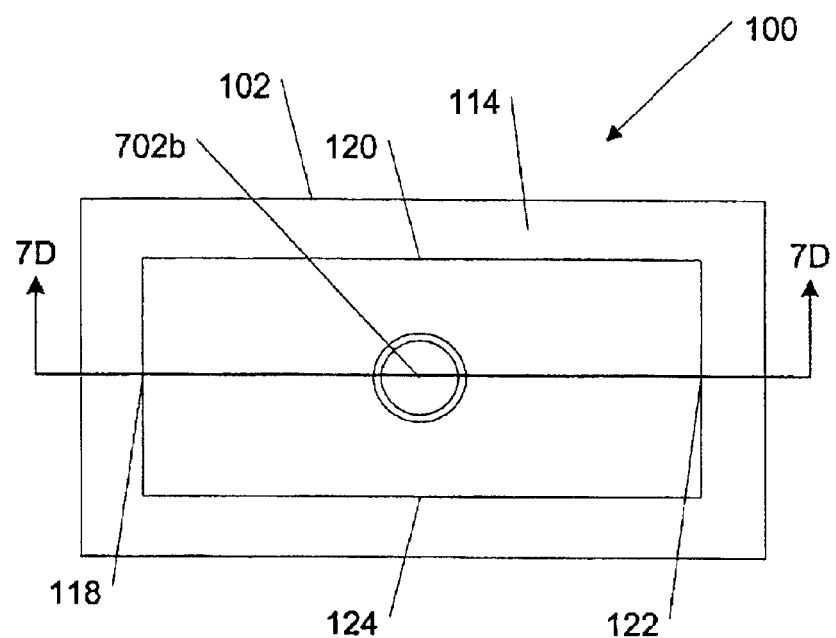

FIG. 7C is a top view of an alternate embodiment of the apparatus of FIG. 1A.

Figure 7D:
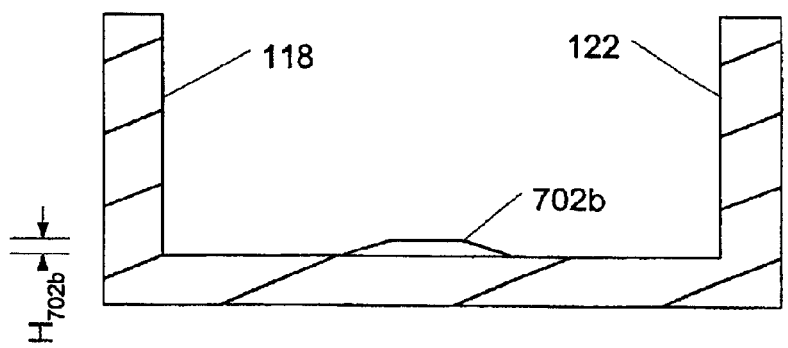

FIG. 7D is a cross-sectional view of an alternate embodiment of the apparatus of FIG. 1A.

DETAILED DESCRIPTION OF THE ILLUSTRATIVE EMBODIMENTS

Referring initially to FIGS. 1A through 1E, an embodiment of a system 100 for resiliently coupling a mass to a package preferably includes a package 102, a mass 104, one or more bond pads 106, one or more resilient couplings 108, and one or more electrical connections 112.

The package 102 is preferably coupled to the resilient couplings 108 and the electrical connections 112. The package 102 may be, for example, a housing or a substrate. In a preferred embodiment, the package 102 is a housing in order to optimally provide a surface mount component. The package 102 preferably includes a top parallel planar surface 114 and a cavity 116. The cavity 116 preferably includes a first wall 118, a second wall 120, a third wall 122 and a fourth wall 124. The first wall 118 and the third wall 122 are preferably approximately parallel to each other and the second wall 120 and the fourth wall 124 are preferably approximately parallel to each other. The second wall 120 and the fourth 124 wall are also preferably perpendicular to the first wall 118 and the third wall 122. The cavity 116 preferably includes a bottom surface 126. The package 102 may be any number of conventional commercially available housings of the type ceramic, metal or plastic. In a preferred embodiment, the package 102 is ceramic in order to optimally provide vacuum sealing of the mass 104 within the package 102.

The mass 104 is preferably resiliently attached to the package 102 by the resilient couplings 108 and electrically coupled to the package 102 by the electrical connections 112. The mass 104 preferably has an approximately rectangular cross-sectional shape. In a preferred embodiment, the mass 104 is a micro machined sensor substantially as disclosed in copending U.S. patent application Ser. No. 09/936,640, filed on Sep. 12, 2001, the disclosure of which is incorporated herein by reference.

In a preferred embodiment, the mass 104 includes a top parallel planar surface 128 and a bottom parallel planar surface 130. The bottom parallel planar surface 130 of the mass 104 preferably includes a first side 132, a second side 134, a third side 136, and a fourth side 138. The first side 132 and the third side 136 are preferably approximately parallel to each other and the second side 134 and the fourth side 138 are preferably approximately parallel to each other and preferably approximately perpendicular to the first side 132 and the third side 136. The mass 104 preferably includes a passive region 140 at one end and an active region 146 at the opposite end.

In a preferred embodiment, the bottom parallel planar surface 130 of the mass 104 includes the bond pads 106. In a preferred embodiment, the bond pads 106 are located in the passive region 140 of the bottom parallel planar surface 130 of the mass 104. The bond pads 106 may be located a perpendicular distance ranging, for example, from about 5 to 25 mils from the first side 132 of the bottom parallel planar surface 130 of the mass 104 and may be located a perpendicular distance ranging, for example, from about 5 to 25 mils from the second side 134 of the bottom parallel planar surface 130 of the mass 104. In a preferred embodiment, the bond pads 106 are located a perpendicular distance ranging from about 7 to 12 mils from the first side 132 of the bottom parallel planar surface 130 of the mass 104 in order to optimally minimize thermal stresses and located a perpendicular distance ranging from about 7 to 12 mils from the second side 134 of the bottom parallel planar surface 130 of the mass 104 in order to optimally minimize thermal stresses. The bond pads 106 may be used for, for example, solder, conductive epoxy, non-conductive epoxy, or glass frit bonding. In a preferred embodiment, the bond pads 106 are used for solder bonding in order to optimally provide good manufacturability. In a preferred embodiment, the bond pads 106 contact area is maximized in order to optimize the shock tolerance of the mass 104. In a preferred embodiment, the bond pads 106 have minimal discontinuities in order to optimize the distribution of thermal stresses in the mass 104. In several alternate embodiments, there is a plurality of bond pads 106 in order to optimize the relief of thermal stresses in the mass 104. In a preferred embodiment, there is a single bond pad 106a. The bond pad 106a preferably has an approximately rectangular cross-sectional shape. The length $L_{106a}$ of the bond pad 106a may range, for example, from about 180 to 240 mils. In a preferred embodiment, the length $L_{106a}$ of the bond pad 106a ranges from about 200 to 220 mils in order to optimally minimize thermal stresses. The width $W_{106a}$ of the bond pad 106a may range, for example, from about 15 to 25 mils. In a preferred embodiment, the width $W_{106a}$ of the bond pad 106a ranges from about 18 to 22 mils in order to optimally minimize thermal stresses. The height $H_{106a}$ of the bond pad 106a may range, for example, from about 0.1 to 1 micron. In a preferred embodiment, the height $H_{106a}$ of the bond pad 106a ranges from about 0.24 to 0.72 microns in order to optimally minimize thermal stresses.

The resilient couplings 108 preferably resiliently attach the bond pads 106 to the package 102. The resilient couplings 108 are preferably coupled to the bottom surface 126 of the cavity 116 of the package 102. In a preferred embodiment, the resilient couplings 108 are solder preforms. In a preferred embodiment, the resilient couplings 108 have an approximately rectangular cross-sectional shape. In a preferred embodiment, the resilient couplings 108 have minimal discontinuities in order to optimize the distribution of thermal stresses. In several alternate embodiments, there is a plurality of resilient couplings 108 in order to optimize the relief of thermal stresses in the mass 104. The resilient couplings 108 may be any number of conventional commercially available solder preforms of the type, for example, eutectic or non-eutectic. In a preferred embodiment, the resilient couplings 108 are a eutectic type in order to optimally provide good yield strength with a reasonable melt temperature. The resilient couplings 108 may be located a perpendicular distance ranging, for example, from about 6 to 25 mils from the first wall 118 of the cavity 116 of the package 102 and may be located a perpendicular distance ranging, for example, from about 5 to 25 mils from the second wall 120 of the cavity 116 of the package 102. In a preferred embodiment, the resilient couplings 108 are located a perpendicular distance ranging from about 7 to 12 mils from the first wall 118 of the cavity 116 of the package 102 in order to optimally minimize thermal stresses and located a distance ranging from about 7 to 12 mils from the second wall 120 of the cavity 116 of the package 102 in order to optimally minimize thermal stresses. In a preferred embodiment, there is a single resilient coupling 108. The length $L_{108}$ of the resilient coupling 108 may range, for example, from about 200 to 250 mails. In a preferred embodiment, the length $L_{108}$ of the resilient coupling 108 ranges from about 225 to 235 mils in order to optimally minimize thermal stresses. The width $W_{108}$ of the resilient coupling 108 may range, for example, from about 20 to 35 mils. In a preferred embodiment, the width $W_{108}$ of the resilient coupling 108 ranges from about 25 to 30 mils in order to optimally minimize thermal stresses. The height $H_{108}$ of the resilient coupling 108 may range, for example, from about 2 to 4 mils. In a preferred embodiment, the height $H_{108}$ of the resilient coupling 108 ranges from about 2.5 to 3 mils in order to optimally minimize thermal stresses.

In a preferred embodiment, the resilient couplings 108 further include one or more first bumpers 142 and one or more second bumpers 144 for slidingly supporting the mass 104. In a preferred embodiment, the first bumpers 142 are located on one side of the bond pads 106 and the second bumpers 144 are located on another side of the bond pads 106. In a preferred embodiment, the first bumpers 142 and the second bumpers 144 are proximate to the bond pads 106. The width $W_{142}$ of the first bumpers 142 may range, for example, from about 2 to 6 mils. In a preferred embodiment, the width $W_{142}$ of the first bumpers 142 ranges from about 3 to 5 mils in order to minimize thermal stresses. The width $W_{144}$ of the second bumpers 144 may range, for example, from about 2 to 6 mils. In a preferred embodiment, the width $W_{144}$ of the second bumpers 144 ranges from about 3 to 5 mils in order to minimize thermal stresses. In a preferred embodiment, the resilient couplings 108 are coupled to the bond pads 106 using conventional solder equipment and processes. In a preferred embodiment, the resilient couplings 108 are coupled to the bottom surface 126 of the cavity 116 of the package 102 using conventional solder equipment and processes. In a preferred embodiment, there is a single first bumper 142 and a single second bumper 144.

The electrical connections 112 preferably electrically couple the mass 104 to the package 102. In a preferred embodiment, there is a single electrical connection 112. The electrical connection 112 preferably electrically couples the top parallel planar surface 114 of the package 102 to the top parallel planar surface 128 of the mass 104. In a preferred embodiment, the electrical connection 112 is a wire bond. The electrical connection 112 may be any number of conventional commercially available wire bonds of the type, for example, aluminum or gold. In a preferred embodiment, the electrical connection 112 is gold in order to optimally provide compatibility with the package 102 and the mass 104 metallization. In a preferred embodiment, the electrical connection 112 is coupled to the package 102 using conventional wire-bonding equipment and processes. In a preferred embodiment, the electrical connection 112 is coupled to the mass 104 using conventional wire-bonding equipment and processes.

Figure 1F:
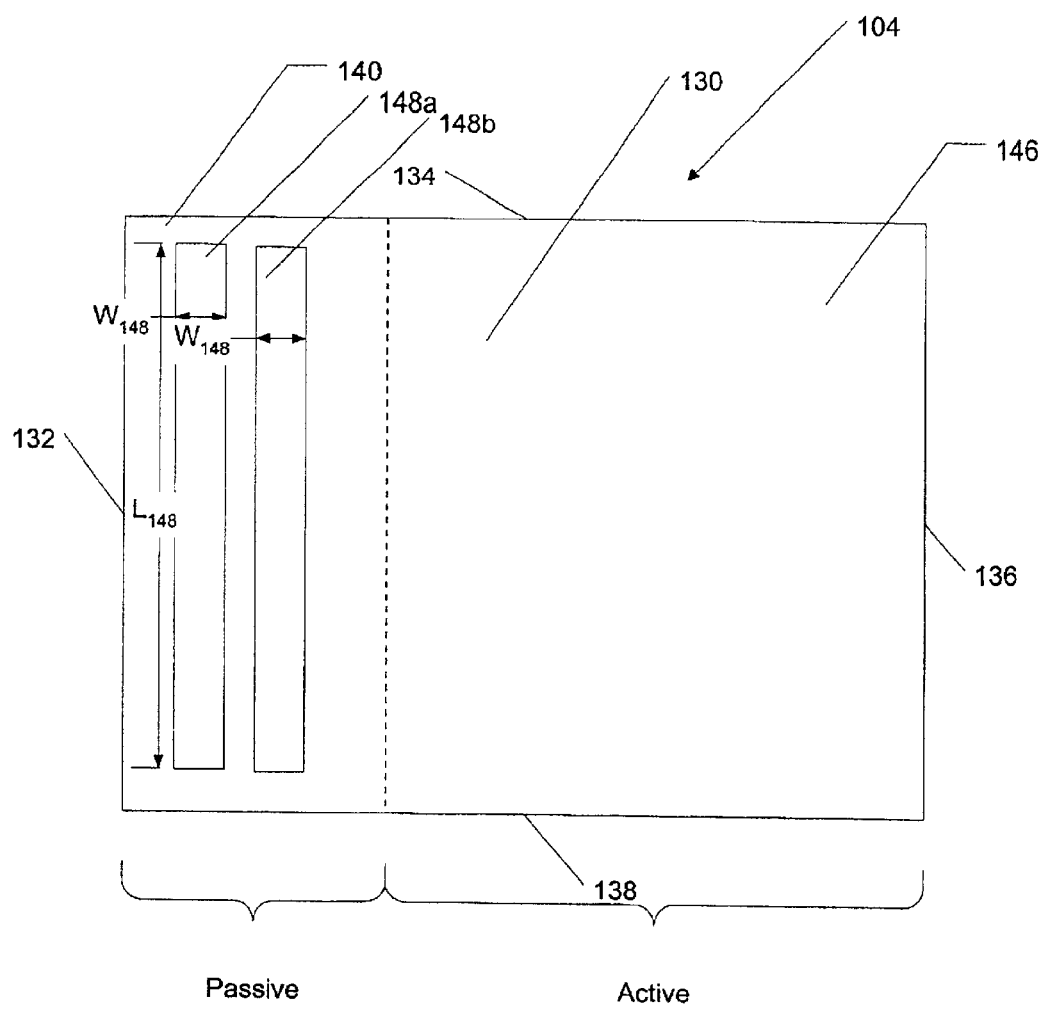
FIG. 1F is a bottom view of an alternate embodiment of the mass of the apparatus of FIG. 1A.

Referring to FIG. 1F, in an alternate embodiment, there is a first bond pad 148a and a second bond pad 148b that are substantially equal in size and horizontally proximate to each other. The bond pads 148a and 148b may be used for, for example, solder, conductive epoxy, non-conductive epoxy, or glass frit bonding. In a preferred embodiment, the bond pads 148a and 148b are used for solder bonding in order to optimally provide good manufacturability. The bond pads 148a and 148b preferably have an approximately rectangular cross-sectional shape. The length $L_{148}$ of the bond pads 148a and 148b may range, for example, from about 180 to 240 mils. In a preferred embodiment, the length $L_{148}$ of the bond pads 148a and 148b range from about 200 to 220 mils in order to optimally minimize thermal stresses. The width $W_{148}$ of the bond pads 148a and 148b may range, for example, from about 10 to 20 mils. In a preferred embodiment, the width $W_{148}$, of the bond pads 148a and 148b range from about 13 to 18 mils in order to optimally minimize thermal stresses. The height $H_{148}$ of the bond pads 148a and 148b may range, for example, from about 0.1 to 1 micron. In a preferred embodiment, the height $H_{148}$ of the bond pads 148a and 148b range from about 0.24 to 0.72 microns in order to optimally minimize thermal stresses.

The first bond pad 148a is preferably located in the passive region 140 of the bottom parallel planar surface 130 of the mass 104. The first bond pad 148a may be located a perpendicular distance ranging, for example, from about 5 to 25 mils from the first side 132 of the bottom parallel planar surface 130 of the mass 104 and may be located a perpendicular distance ranging, for example, from about 5 to 25 mils from the second side 134 of the bottom parallel planar surface 130 of the mass 104. The first bond pad 148a is preferably located a perpendicular distance ranging from about 7 to 12 mils from the first side 132 of the bottom parallel planar surface 130 of the mass 104 in order to optimally minimize thermal stresses and located a perpendicular distance ranging from about 7 to 12 mils from the second side 134 of the bottom parallel planar surface 130 of the mass 104 in order to optimally minimize thermal stresses.

The second bond pad 148b is preferably located in the passive region 140 of the bottom parallel planar surface 130 of the mass 104. The second bond pad 148b may be located a perpendicular distance ranging, for example, from about 15 to 45 mils from the first side 132 of the bottom parallel planar surface 130 of the mass 104 and may be located a perpendicular distance ranging, for example, from about 5 to 25 mils from the second side 134 of the bottom parallel planar surface 130 of the mass 104. The second bond pad 148b is preferably located a perpendicular distance ranging from about 20 to 30 mils from the first side 132 of the bottom parallel planar surface 130 of the mass 104 in order to optimally minimize thermal stresses and located a perpendicular distance ranging from about 7 to 12 mils from the second side 134 of the bottom parallel planar surface 130 of the mass 104 in order to optimally minimize thermal stresses.

Figure 1G:
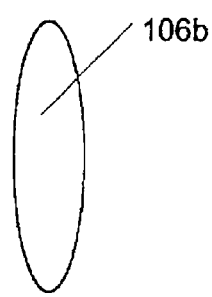
FIG. 1G is a top view of an alternate embodiment of the bond pad of the apparatus of FIG. 1A.

Referring to FIG. 1G, in an alternate embodiment, there is a single bond pad 106b. The bond pad 106b may have an approximately oval cross-sectional shape. The bond pad 106b may have an approximate cross-sectional area ranging from about 4000 to 8750 square mils. In a preferred embodiment, the bond pad 106b has an approximate cross-sectional area ranging from about 5625 to 7050 square mils in order to optimally minimize thermal stresses. The height $H_{106}$ of the bond pad 106b may range, for example, from about 0.1 to 1 micron. In a preferred embodiment, the height $H_{106}$ of the bond pad 106b range from about 0.24 to 0.72 microns in order to optimally minimize thermal stresses.

Figure 1H:
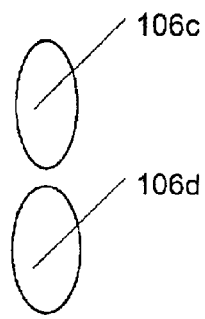
FIG. 1H is a top view of an alternate embodiment of the bond pad of the apparatus of FIG. 1A.

Referring to FIG. 1H, in an alternate embodiment, there is a bond pad 106c and a bond pad 106d. The bond pads 106c and 106d are substantially equal in size, vertically proximate to each other, and have an approximately oval cross-sectional shape. The bond pads 106c and 106d may have an approximate total cross-sectional area ranging from about 4000 to 8750 square mils. In a preferred embodiment, the bond pads 106c and 106d have an approximate total cross-sectional area ranging from about 5625 to 7050 square mils in order to optimally minimize thermal stresses. The height $H_{106}$ of the bond pads 106c and 106d may range, for example, from about 0.1 to 1 micron. In a preferred embodiment, the height $H_{106}$ of the bond pads 106c and 106d range from about 0.24 to 0.72 microns in order to optimally minimize thermal stresses.

Figure 1J:
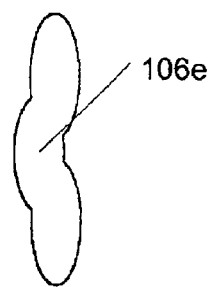
FIG. 1J is a top view of an alternate embodiment of the bond pad of the apparatus of FIG. 1A.

Referring to FIG. 1J, in an alternate embodiment, there is a single bond pad 106e. The bond pad 106e has an approximately tri-oval cross-sectional shape. The bond pad 106e may have an approximate cross-sectional area ranging from about 4000 to 8750 square mils. In a preferred embodiment, the bond pad 106e has an approximate total cross-sectional area ranging from about 5625 to 7050 square mils in order to optimally provide minimize thermal stresses. The height $H_{106}$ of the bond pad 106e may range, for example, from about 0.1 to 1 micron. In a preferred embodiment, the height $H_{106}$ of the bond pad 106e ranges from about 0.24 to 0.72 microns in order to optimally minimize thermal stresses.

Figure 1K:
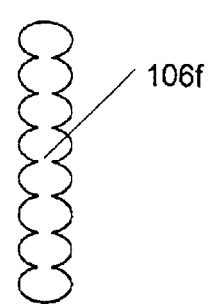
FIG. 1K is a top view of an alternate embodiment of the bond pad of the apparatus of FIG. 1A.

Referring to FIG. 1K, in an alternate embodiment, there is a single bond pad 106f. The bond pad 106f may have an approximately oct-oval cross-sectional shape. The bond pad 106f may have an approximate cross-sectional area ranging from about 4000 to 8750 square mils. In a preferred embodiment, the bond pad 106f has an approximate cross-sectional area ranging from about 5625 to 7050 square mils in order to optimally minimize thermal stresses. The height $H_{106}$ of the bond pad 106f may range, for example, from about 0.1 to 1 micron. In a preferred embodiment, the height $H_{106}$ of the bond pad 106b ranges from about 0.24 to 0.72 microns in order to optimally minimize thermal stresses.

Figure 1L:
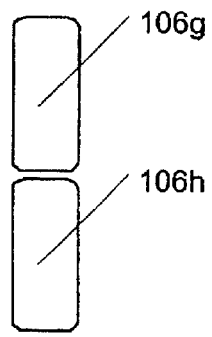
FIG. 1L is a top view of an alternate embodiment of the bond pad of the apparatus of FIG. 1A.

Referring to FIG. 1L, in an alternate embodiment, there is a bond pad 106g and a bond pad 106h. The bond pads 106g and 106h are substantially equal in size, vertically proximate to each other, and have an approximately rectangular cross-sectional shape. The bond pads 106g and 106h may have an approximate total cross-sectional area ranging from about 4000 to 8750 square mils. In a preferred embodiment, the bond pads 106g and 106h have an approximate total cross-sectional area ranging from about 5625 to 7050 square mils in order to optimally minimize thermal stresses. The height $H_{106}$ of the bond pads 106g and 106h may range, for example, from about 0.1 to 1 micron. In a preferred embodiment, the height $H_{106}$ of the bond pads 106g and 106h range from about 0.24 to 0.72 microns in order to optimally minimize thermal stresses.

Figure 1M:
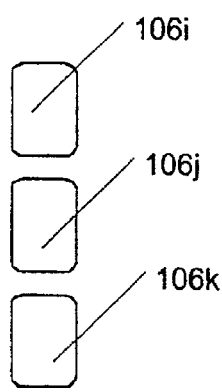
FIG. 1M is a top view of an alternate embodiment of the bond pad of the apparatus of FIG. 1A.

Referring to FIG. 1M, in an alternate embodiment, there is a bond pad 106i, a bond pad 106j, and a bond pad 106k. The bond pads 106i, 106j, and 106k are substantially equal in size, vertically proximate to each other, and have an approximately rectangular cross-sectional shape. The bond pads 106i, 106j, and 106k may have an approximate total cross-sectional area ranging from about 4000 to 8750 square mils. In a preferred embodiment, the bond pads 106i, 106j, and 106k have an approximate total cross-sectional area ranging from about 5625 to 7050 square mils in order to optimally minimize thermal stresses. The height $H_{106}$ of the bond pads 106i, 106j, and 106k may range, for example, from about 0.1 to 1 micron. In a preferred embodiment, the height $H_{106}$ of the bond pads 106i, 106j, and 106k range from about 0.24 to 0.72 microns in order to optimally minimize thermal stresses.

Figure 1N:
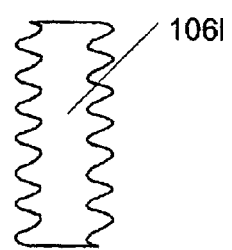
FIG. 1N is a top view of an alternate embodiment of the bond pad of the apparatus of FIG. 1A.

Referring to FIG. 1N in an alternate embodiment, there is a single bond pad 106l. The bond pad 106l may have an approximately wavy sided rectangular cross-sectional shape. The bond pad 106l may have an approximate cross-sectional area ranging from about 4000 to 8750 square mils. In a preferred embodiment, the bond pad 106l has an approximate cross-sectional area ranging from about 5625 to 7050 square mils in order to optimally minimize thermal stresses. The height $H_{106}$ of the bond pad 106l may range, for example, from about 0.1 to 1 micron. In a preferred embodiment, the height $H_{106}$ of the bond pad 106*l* ranges from about 0.24 to 0.72 microns in order to optimally minimize thermal stresses.

Figure 1P:
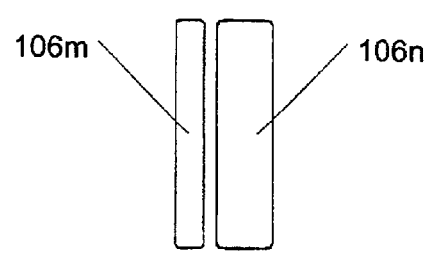
FIG. 1P is a top view of an alternate embodiment of the bond pad of the apparatus of FIG. 1A.

Referring to FIG. 1P, in an alternate embodiment, there is a bond pad 106*m* and a bond pad 106*n*. The bond pads 106*m* and 106*n* are horizontally proximate to each other and have an approximately rectangular cross-sectional shape. The bond pad 106*m* is approximately smaller in size than the bond pad 106*n*. The bond pads 106*m* and 106*n* may have an approximate total cross-sectional area ranging from about 4000 to 8750 square units. In a preferred embodiment, the bond pads 106*m* and 106*n* have an approximate total cross-sectional area ranging from about 5625 to 7050 square mils in order to optimally minimize thermal stresses. The height $H_{106}$ of the bond pads 106*m* and 106*n* may range, for example, from about 0.1 to 1 micron. In a preferred embodiment, the height $H_{106}$ of the bond pads 106*m* and 106*n* range from about 0.24 to 0.72 microns in order to optimally minimize thermal stresses.

Figure 1Q:
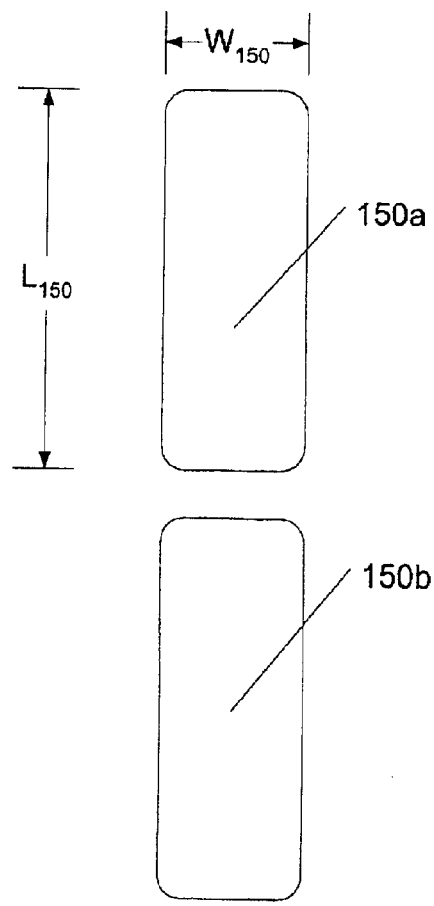
FIG. 1Q is a top view of an alternate embodiment of the resilient coupling of the apparatus of FIG. 1A.
Figure 1R:
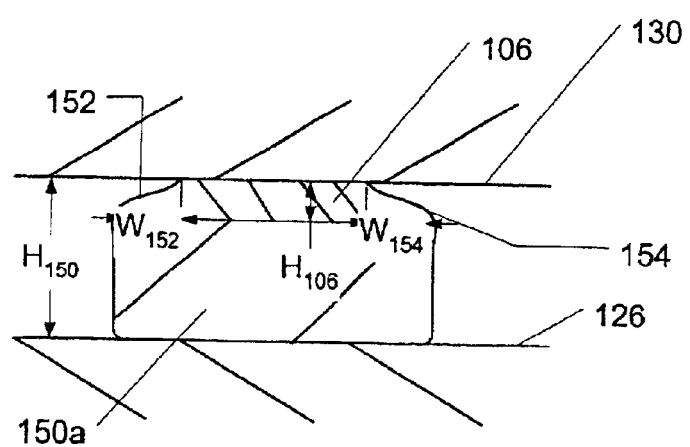
FIG. 1R is a detailed view of the alternate embodiment of the resilient coupling of FIG. 1Q.
Figure 1S:
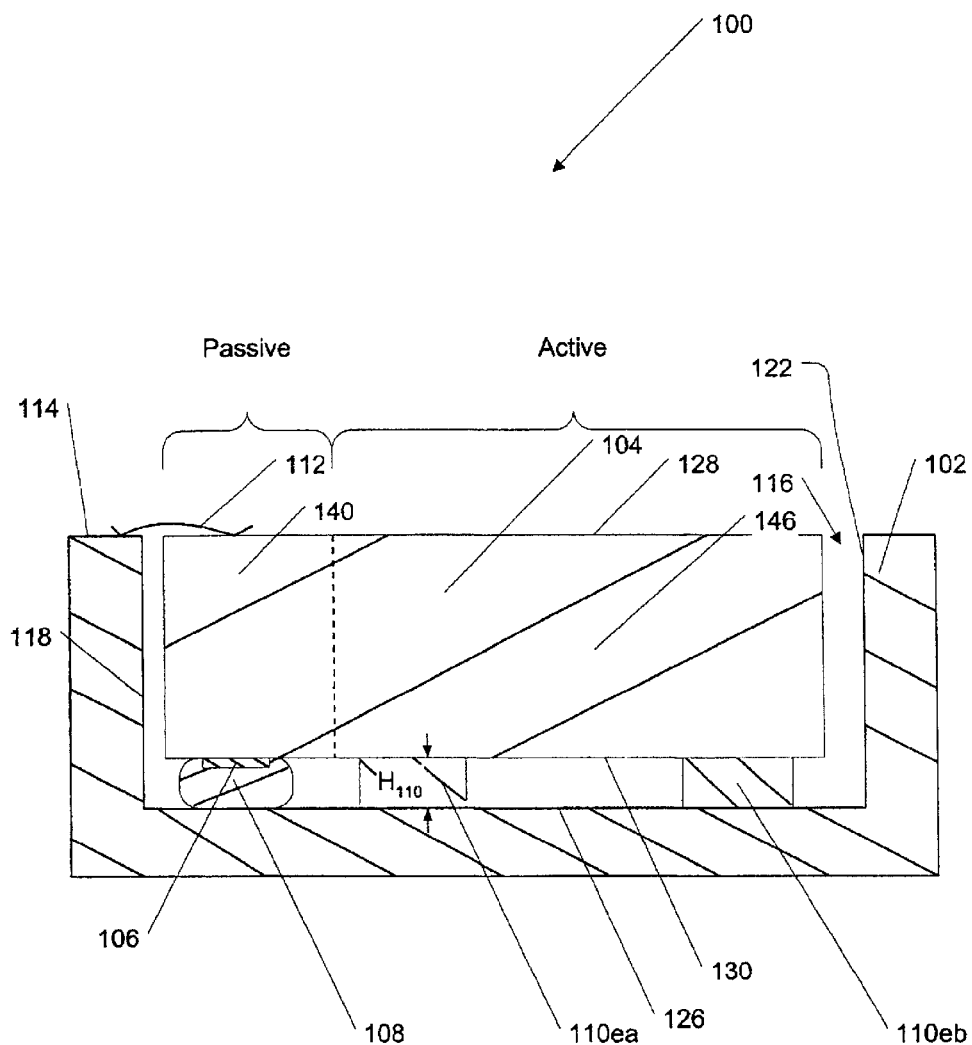
FIG. 1S is a cross-sectional view illustrating an alternate embodiment of an apparatus for resiliently attaching a mass to a package.
Figure 1T:
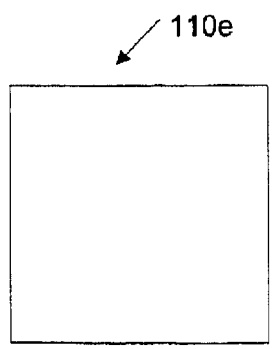
FIG. 1T is a top view of an embodiment of the sliding supports of the apparatus of FIG. 1S.
Figure 1U:
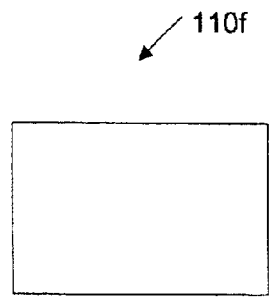
FIG. 1U is a top view of an alternate embodiment of the sliding supports of the apparatus of FIG. 1S.
Figure 1V:
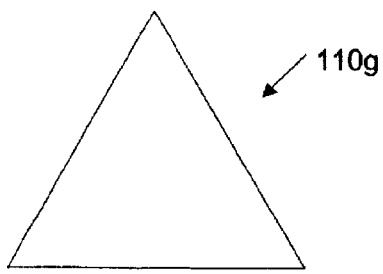
FIG. 1V is a top view of an alternate embodiment of the sliding supports of the apparatus of FIG. 1S.
Figure 1W:
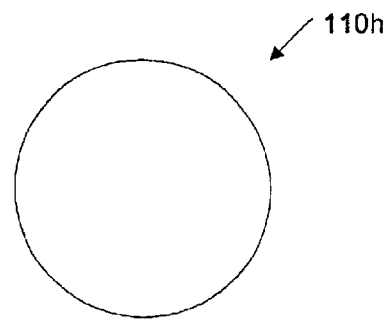
FIG. 1W is a top view of an alternate embodiment of the sliding supports of the apparatus of FIG. 1S.

Referring to FIGS. 1Q and 1R, in an alternate embodiment, there is a first resilient coupling 150*a* and a second resilient coupling 150*b*. In a preferred embodiment, the resilient couplings 150*a* and 150*b* are solder preforms preferably having an approximately rectangular cross-sectional shape. The resilient couplings 150*a* and 150*b* are vertically proximate to each other and substantially equal in size. The resilient couplings 150*a* and 150*b* may be any number of conventional commercially available solder preforms of the type, for example, eutectic or non-eutectic. In a preferred embodiment, the resilient couplings 150*a* and 150*b* are a eutectic type in order to optimally provide good yield strength with a reasonable melt temperature. The length $L_{150}$ of the resilient couplings 150*a* and 150*b* may range, for example, from about 90 to 120 mils. In a preferred embodiment, the length $L_{150}$ of the resilient couplings 150*a* and 150*b* ranges from about 101 to 112 mils in order to optimally minimize thermal stresses. The width $W_{150}$ of the resilient couplings 150*a* and 150*b* may range, for example, from about 20 to 35 mils. In a preferred embodiment, the width $W_{150}$ of the resilient couplings 150*a* and 150*b* ranges from about 25 to 30 mils in order to optimally minimize thermal stresses. The height $H_{150}$ of the resilient couplings 150*a* and 150*b* may range, for example, from about 2 to 4 mils. In a preferred embodiment, the height $H_{150}$ of the resilient couplings 150*a* and 150*b* ranges from about 2.5 to 3 mils in order to optimally minimize thermal stresses. In a preferred embodiment, the resilient couplings 150*a* and 150*b* are coupled to the bottom surface 126 of the cavity 116 of the package 102 using conventional solder equipment and processes.

The first resilient coupling 150*a* may be located a perpendicular distance ranging, for example, from about 5 to 25 mils from the first wall 118 of the cavity 116 of the package 102 and may be located a perpendicular distance ranging, for example, from about 5 to 25 mils from the second wall 120 of the cavity 116 of the package 102. In a preferred embodiment, the first resilient coupling 150*a* is located a perpendicular distance ranging from about 7 to 12 mils from the first wall 118 of the cavity 116 of the package 102 in order to optimally minimize thermal stresses and located a distance ranging from about 7 to 12 mils from the second wall 120 of the cavity 116 of the package 102 in order to optimally minimize thermal stresses.

The second resilient coupling 150*b* may be located a perpendicular distance ranging, for example, from about 5 to 25 mils from the first wall 118 of the cavity 116 of the package 102 and may be located a perpendicular distance ranging, for example, from about 105 to 145 mils from the second wall 120 of the cavity 116 of the package 102. In a preferred embodiment, the second resilient coupling 150*b* is located a perpendicular distance ranging from about 7 to 12 mils from the first wall 118 of the cavity 116 of the package 102 in order to optimally minimize thermal stresses and located a distance ranging from about 112 to 127 mils from the second wall 120 of the cavity 116 of the package 102 in order to optimally minimize thermal stresses.

In a preferred embodiment, the resilient couplings 150*a* and 150*b* further include one or more first bumpers 152 for slidingly supporting the mass 104. In a preferred embodiment, the first bumpers 152 are located on one side of the bond pads 106. In a preferred embodiment, the first bumpers 152 are proximate to the bond pads 106. The width $W_{152}$ of the first bumpers 152 may range, for example, from about 2 to 6 mils. In a preferred embodiment, the width $W_{152}$ of the first bumpers 152 ranges from about 3 to 5 mils in order to optimally minimize thermal stresses.

In a preferred embodiment, the resilient couplings 150*a* and 150*b* further include one or more second bumpers 154 for slidingly supporting the mass 104. In a preferred embodiment, the second bumpers 154 are located on another side of the bond pads 106 opposite the bumpers 152. In a preferred embodiment, the second bumpers 154 are proximate to the bond pads 106. The width $W_{154}$ of the second bumpers 154 may range, for example, from about 2 to 6 mils. In a preferred embodiment, the width $W_{152}$ of the second bumpers 154 range from about 3 to 5 mils in order to optimally minimize thermal stresses.

Referring to FIGS. 1S through 1W, in an alternate embodiment, the system 100 further includes one or more sliding supports 110*e*, 110*f*, 110*g* or 10*h* preferably slidingly supporting the mass 104. The number of sliding supports 110*e*, 110*f*, 110*g* or 110*h* preferably depends upon having a sufficient amount of sliding supports 110*e*, 110*f*, 110*g* or 110*h* in order to optimally slidingly support the mass 104. The sliding supports 110*e*, 110*f*, 110*g* or 110*h* are preferably coupled to the bottom surface 126 of the cavity 116 of the package 102.

The sliding supports 110*e* may have an approximately square cross-sectional shape. The sliding supports 110*f* may have an approximately rectangular cross-sectional shape. The sliding supports 110*g* may have an approximately triangular cross-sectional shape. The sliding supports 110*h* may have an approximately circular cross-sectional shape. The sliding supports 110*e*, 110*f*, 110*g* or 110*h* may have an approximate cross-sectional area ranging from about 400 to 1600 square mils, individually. In a preferred embodiment, the sliding supports 110*e*, 110*f*, 110*g* or 110*h* have an approximate cross-sectional area ranging from about 625 to 1225 square mils, individually, in order to optimally minimize thermal stresses. The height $H_{110}$ of the sliding supports 110*e*, 110*f*, 110*g* or 110*h* may range, for example, from about 0.5 to 3 mils. In a preferred embodiment, the height $H_{110}$ of the sliding supports 110*e*, 110*f*, 110*g* or 110*h* ranges from about 1 to 1.5 mils in order to optimally minimize thermal stresses.

The sliding supports 110*e*, 110*f*, 110*g* or 110*h* may be, for example, tungsten or ceramic. In a preferred embodiment, the sliding supports 110*e*, 110*f*, 110*g* or 110*h* are tungsten in order to optimally provide a standard packaging procedure. In a preferred embodiment, the sliding supports 110*c*, 110*f*, 110*g* or 110*h* are coupled to the bottom surface 126 of the cavity 116 of the package 102 using conventional means of integrating the sliding supports 110 into the package 102.

In a preferred embodiment, there is a first sliding support 110ea, a second sliding support 110eb, a third sliding support 110ec, and a fourth sliding support 110ed. In a preferred embodiment, the sliding supports 110ea, 110eb, 110ec, and 110ed have an approximately square cross-sectional shape. The first sliding support 110ea may be located a perpendicular distance ranging, for example, from about 45 to 75 mils from the first wall 118 of the cavity 116 of the package 102 and may be located a perpendicular distance ranging, for example, from about 85 to 115 mils from the second wall 120 of the cavity 116 of the package 102. In a preferred embodiment, the first sliding support 110ea is located a perpendicular distance ranging from about 52 to 62 mils from the first wall 118 of the cavity 116 of the package 102 in order to optimally minimize thermal stresses and located a perpendicular distance from about 90 to 105 mils from the second wall 120 of the cavity 116 of the package 102 in order to optimally minimize thermal stresses.

The second sliding support 110eb may be located a perpendicular distance ranging, for example, from about 45 to 75 mils from the first wall 118 of the cavity 116 of the package 102 and may be located a perpendicular distance ranging, for example, from about 15 to 30 mils from the second wall 120 of the cavity 116 of the package 102. In a preferred embodiment, the second sliding support 110eb is located a perpendicular distance ranging from about 52 to 62 mils from the first wall 118 of the cavity 116 of the package 102 in order to optimally minimize thermal stresses and located a perpendicular distance ranging from about 20 to 25 mils from the second wall 120 of the cavity 116 of the package 102 in order to optimally minimize thermal stresses.

The third sliding support 110ec may be located a perpendicular distance ranging, for example, from about 85 to 115 mils from the first wall 118 of the cavity 116 of the package 102 and may be located a perpendicular distance ranging, for example, from about 15 to 30 mils from the second wall 120 of the cavity 116 of the package 102. In a preferred embodiment, the third sliding support 110ec is located a perpendicular distance ranging from about 90 to 105 mils from the first wall 118 of the cavity 116 of the package 102 in order to optimally minimize thermal stresses and located a perpendicular distance ranging from about 20 to 25 mils from the second wall 120 of the cavity 116 of the package 102 in order to optimally minimize thermal stresses.

The fourth sliding support 110ed may be located a perpendicular distance ranging, for example, from about 85 to 115 mils from the first wall 118 of the cavity 116 of the package 102 and may be located a perpendicular distance ranging, for example, from about 85 to 115 mils from the second wall 120 of the cavity 116 of the package 102. In a preferred embodiment, the fourth sliding support 110ed is located a perpendicular distance ranging from about 90 to 105 mils from the first wall 118 of the cavity 116 of the package 102 in order to optimally minimize thermal stresses and located a perpendicular distance ranging from about 90 to 105 mils from the second wall 120 of the cavity 116 of the package 102 in order to optimally minimize thermal stresses.

In an alternate embodiment, the resilient couplings 108 may also electrically couple the mass 104 to the package 102.

In an alternate embodiment, the resilient couplings 150a and 150b may also electrically couple the mass 104 to the package 102.

Referring to FIGS. 2A through 2E, an embodiment of a system 200 for resiliently coupling a mass to a package preferably includes a package 202, a mass 204, one or more bond pads 206, one or more resilient couplings 208, and one or more electrical connections 212.

The package 202 is preferably coupled to the resilient couplings 208 and the electrical connections 212. The package 202 may be, for example, a housing or a substrate. In a preferred embodiment, the package 202 is a housing in order to optimally provide a surface mount component. The package 202 preferably includes a first parallel planar surface 214, a second parallel planar surface 216 and a cavity 218. The cavity 218 preferably includes a first wall 220, a second wall 222, a third wall 224 and a fourth wall 226. The first wall 220 and the third wall 224 are preferably approximately parallel to each other and the second wall 222 and the fourth wall 226 are preferably approximately parallel to each other. The second wall 222 and the fourth wall 226 are also preferably perpendicular to the first wall 220 and the third wall 224. The cavity 218 preferably includes a bottom surface 228. The package 202 may be any number of conventional commercially available housings of the type, for example, ceramic, metal or plastic. In a preferred embodiment, the package 202 is ceramic in order to optimally provide vacuum sealing of the mass 204 in the package 202.

The mass 204 is preferably resiliently attached to the package 202 by the resilient couplings 268 and electrically coupled to the package 202 by the electrical connections 212. The mass 204 preferably has an approximately rectangular cross-sectional shape. The mass 204 preferably has a passive region 250 on one end and an active region 256 at the opposite end. In a preferred embodiment, the mass 204 includes a first member 230, a second member 232, and a third member 234. The first member 230 is preferably on top of the second member 232 and the second member 232 is preferably on top of the third member 234. In a preferred embodiment, the first member 230, the second member 232, and the third member 234 are a micro machined sensor substantially as disclosed in copending U.S. patent application Ser. No. 09/936,640, filed on Sep 12, 2001, the disclosure of which is incorporated herein by reference. The first member 230 preferably includes one or more parallel planar surfaces. In a preferred embodiment, the first member includes a top parallel planar surface 236. The second member 232 preferably includes one or more parallel planar surfaces. In a preferred embodiment, the second member 232 includes a middle parallel planar surface 238. The third member 234 preferably includes one or more parallel planar surfaces. In a preferred embodiment, the third member 234 includes a bottom parallel planar surface 240. The bottom parallel planar surface 240 of the mass 204 preferably includes a first side 242, a second side 244, a third side 246, and a fourth side 248. The first side 242 and the third side 246 are preferably approximately parallel to each other and the second side 244 and the fourth side 248 are preferably approximately parallel to each other and preferably approximately perpendicular to the first side 242 and the third side 246.

In a preferred embodiment, the bottom parallel planar surface 240 of the mass 204 includes the bond pads 206. In a preferred embodiment, the bond pads 206 are located in the passive region 250 of the bottom parallel planar surface 240 of the mass 204. The bond pads 206 may be located a perpendicular distance ranging, for example, from about 5 to 25 mils from the first side 242 of the bottom parallel planar surface 240 of the mass 204 and may be located a perpendicular distance ranging, for example, from about 5 to 25 mils from the second side 244 of the bottom parallel planar surface 240 of the mass 204. In a preferred embodiment, the bond pads 206 are located a perpendicular distance ranging from about 7 to 12 mils from the first side 242 of the bottom parallel planar surface 240 of the mass 204 in order to optimally minimize thermal stresses and located a perpendicular distance ranging from about 7 to 12 mils from the second side 244 of the bottom parallel planar surface 240 of the mass 204 in order to optimally minimize thermal stresses. The bond pads 206 may be used for, for example, solder, glass frit, conductive epoxy, or non-conductive epoxy bonding. In a preferred embodiment, the bond pads 206 are used for solder bonding in order to optimally provide good manufacturability. In a preferred embodiment, the bond pads 206 contact area is maximized in order to optimize the shock tolerance of the mass 204. In a preferred embodiment, the bond pads 206 have minimal discontinuities in order to optimize the distribution of thermal stresses in the mass 204. In several alternate embodiments, there is a plurality of bond pads 206 in order to optimize the relief of thermal stresses in the mass 204. In a preferred embodiment, there is a single bond pad 206a. The bond pad 206a preferably has an approximately rectangular cross-sectional shape. The length $L_{206a}$ of the bond pad 206a may range, for example, from about 180 to 240 mils. In a preferred embodiment, the length $L_{206a}$ of the bond pad 206a ranges from about 200 to 220 mils in order to optimally minimize thermal stresses. The width $W_{206a}$ of the bond pad 206a may range, for example, from about 15 to 25 mils. In a preferred embodiment, the width $W_{206a}$ of the bond pad 206a ranges from about 18 to 22 mils in order to optimally minimize thermal stresses. The height $H_{206a}$ of the bond pad 206a may range, for example, from about 0.1 to 1 micron. In a preferred embodiment, the height $H_{206a}$ of the bond pad 206a ranges from about 0.24 to 0.72 microns in order to optimally minimize thermal stresses.

The resilient couplings 208 preferably resiliently attach the bond pads 206 to the package 202. The resilient couplings 208 are preferably coupled to the bottom surface 228 of the cavity 218 of the package 202. In a preferred embodiment, the resilient couplings 208 are solder preforms. In a preferred embodiment, the resilient couplings 208 have an approximate cross-sectional rectangular shape. In a preferred embodiment, the resilient couplings 208 have minimal discontinuities in order to optimize the distribution of thermal stresses. In several alternate embodiments, there is a plurality of resilient couplings 208 in order to optimize the relief of thermal stresses in the mass 204. The resilient couplings 208 may be any number of conventional commercially available solder preforms of the type, for example, eutectic or non-eutectic. In a preferred embodiment, the resilient couplings 208 are a eutectic type in order to optimally provide good yield strength with a reasonable melt temperature. The resilient couplings 208 may be located a perpendicular distance ranging, for example, from about 5 to 25 mils from the first wall 220 of the cavity 218 of the package 202 and may be located a perpendicular distance ranging, for example, from about 5 to 25 mils from the second wall 222 of the cavity 218 of the package 202. In a preferred embodiment, the resilient couplings 208 are located a perpendicular distance ranging from about 7 to 12 mils from the first wall 220 of the cavity 218 of the package 202 in order to optimally minimize thermal stresses and located a distance ranging from about 7 to 12 mils from the second wall 222 of the cavity 218 of the package 202 in order to optimally minimize thermal stresses. In a preferred embodiment, there is a single resilient coupling 208. The length $L_{208}$ of the resilient coupling 208 may range, for example, from about 200 to 250 mils. In a preferred embodiment, the length $L_{208}$ of the resilient coupling 208 ranges from about 225 to 235 mils in order to optimally minimize thermal stresses. The width $W_{208}$ of the resilient coupling 208 may range, for example, from about 20 to mils. In a preferred embodiment, the width $W_{208}$ of the resilient coupling 208 ranges from about 25 to 30 mils in order to optimally minimize thermal stresses. The height $H_{208}$ of the resilient coupling 208 may range, for example, from about 2 to 4 mils. In a preferred embodiment, the height $H_{208}$ of the resilient coupling 208 ranges from about 2.5 to 3 mils in order to optimally minimize thermal stresses.

In a preferred embodiment, the resilient couplings 208 further include one or more first bumpers 252 and one or more second bumpers 254 for slidingly supporting the mass 204. In a preferred embodiment, the first bumpers 252 are located on one side of the bond pads 206 and the second bumpers 254 are located on another side of the bond pads 206. In a preferred embodiment, the first bumpers 252 and the second bumpers 254 are proximate to the bond pads 206. The width $W_{252}$ of the first bumpers 252 may range, for example, from about 2 to 6 mils. In a preferred embodiment, the width $W_{252}$ of the first bumpers 252 ranges from about 3 to 5 mils in order to optimally minimize thermal stresses. The width $W_{254}$ of the second bumpers 254 may range, for example, from about 2 to 6 mils. In a preferred embodiment, the width $W_{254}$ of the second bumpers 254 ranges from about 3 to 5 mils in order to optimally minimize thermal stresses. In a preferred embodiment, the resilient couplings 208 are coupled to the bond pads 206 using conventional solder equipment and processes. In a preferred embodiment, the resilient couplings 208 are coupled to the bottom surface 228 of the cavity 218 of the package 202 using conventional solder equipment and processes. In a preferred embodiment, there is a single first bumper 252 and a single second bumper 254.

The electrical connections 212 preferably electrically couple the mass 204 to the package 202. In a preferred embodiment, the electrical connections 212 are wire bonds. The electrical connections 212 may be any number of conventional commercially available wire bonds of the type, for example, gold or aluminum. In a preferred embodiment, the electrical connections 212 are gold in order to optimally provide compatibility with the package 202 and the mass 204 metallization. In a preferred embodiment, there is a first electrical connection 212a and a second electrical connection 212b. The first electrical connection 212a preferably electrically couples the first parallel planar surface 214 of the package 202 to the top parallel planar surface 236 of the mass 204. The second electrical connection 212b preferably electrically couples the second parallel planar surface 216 of the package 202 to the middle parallel planar surface 238 of the mass 204. In a preferred embodiment, the electrical connections 212 are coupled to the package 202 using conventional wire-bonding equipment and processes. In a preferred embodiment, the electrical connections 212 are coupled to the mass 204 using conventional wire-bonding equipment and processes.

Figure 2A:
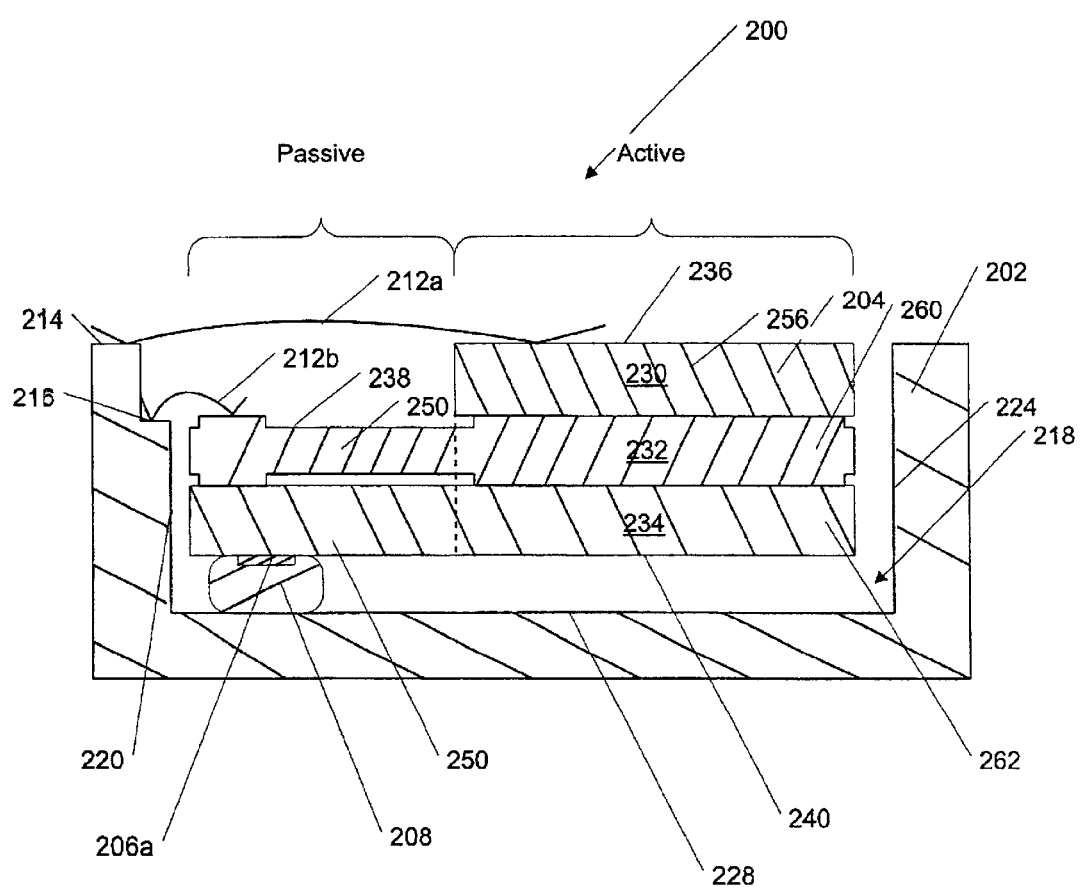
FIG. 2A is a cross-sectional view illustrating an embodiment of an apparatus for resiliently attaching a mass to a package.
Figure 2B:
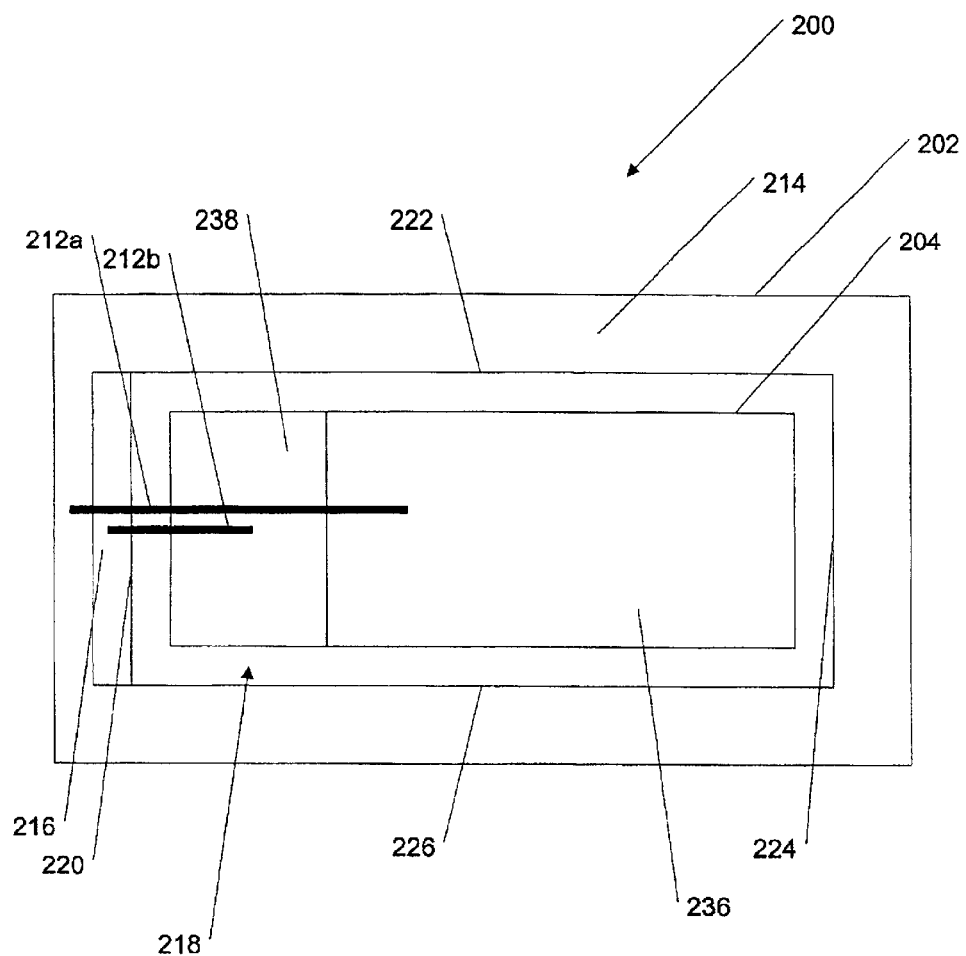
FIG. 2B is a top view of an embodiment of the apparatus of FIG. 2A.
Figure 2C:
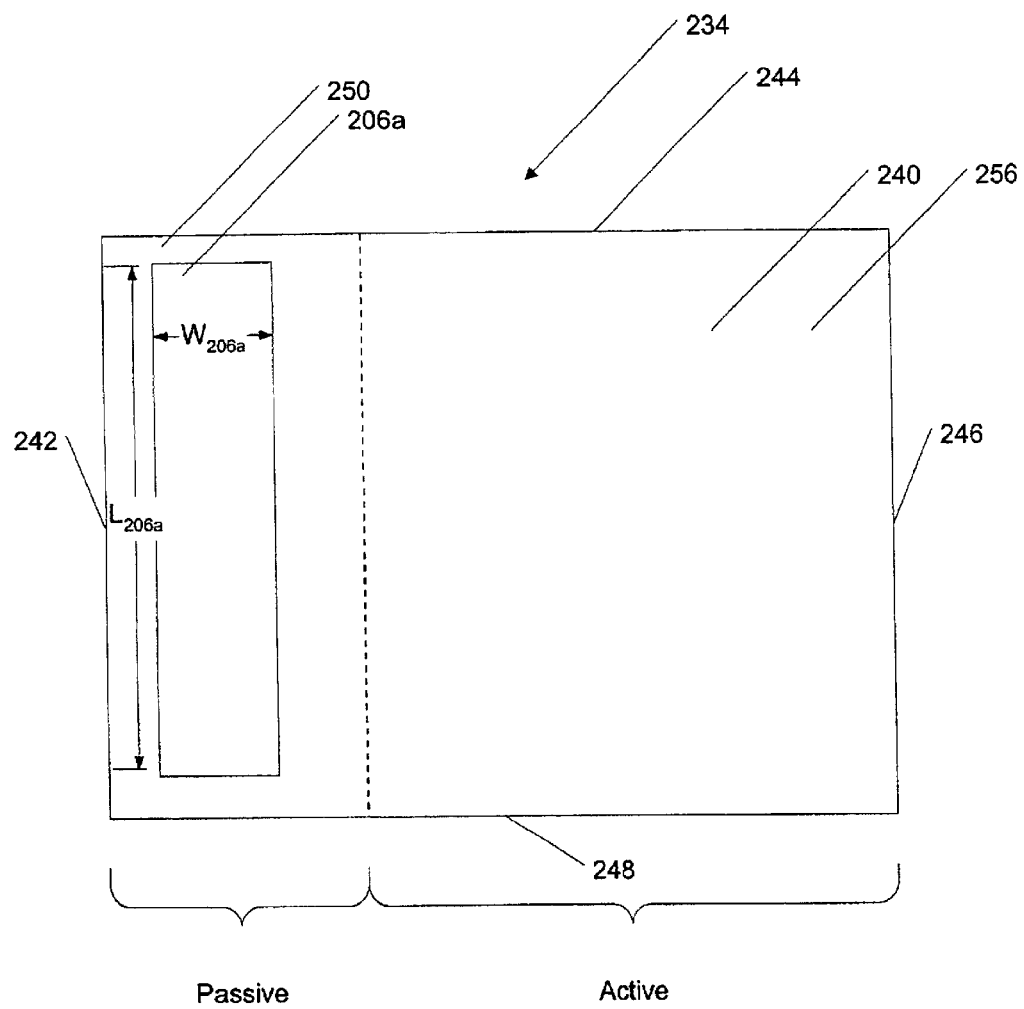
FIG. 2C is a bottom view of al embodiment of the mass of the apparatus of FIG. 2A.
Figure 2D:
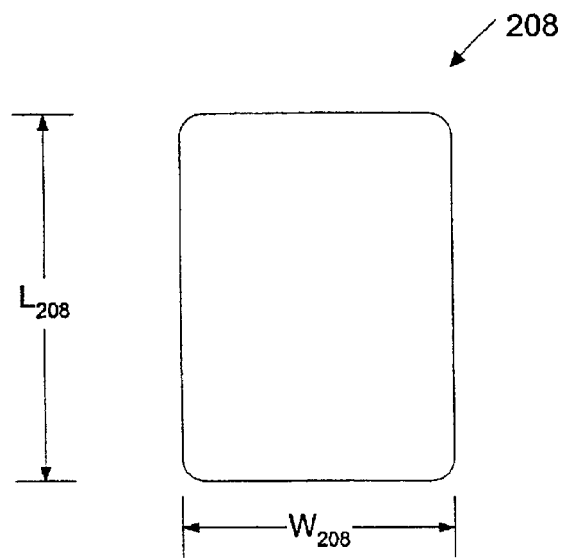
FIG. 2D is a top view of an embodiment of the resilient coupling of the apparatus of FIG. 2A.
Figure 2E:
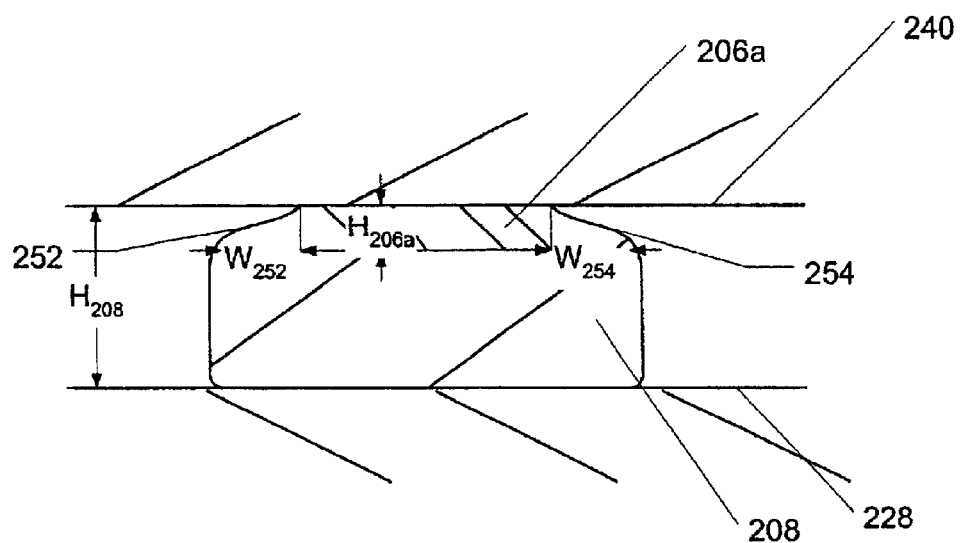
FIG. 2E is a detailed view of the embodiment of the resilient coupling of FIG. 2D.
Figure 2F:
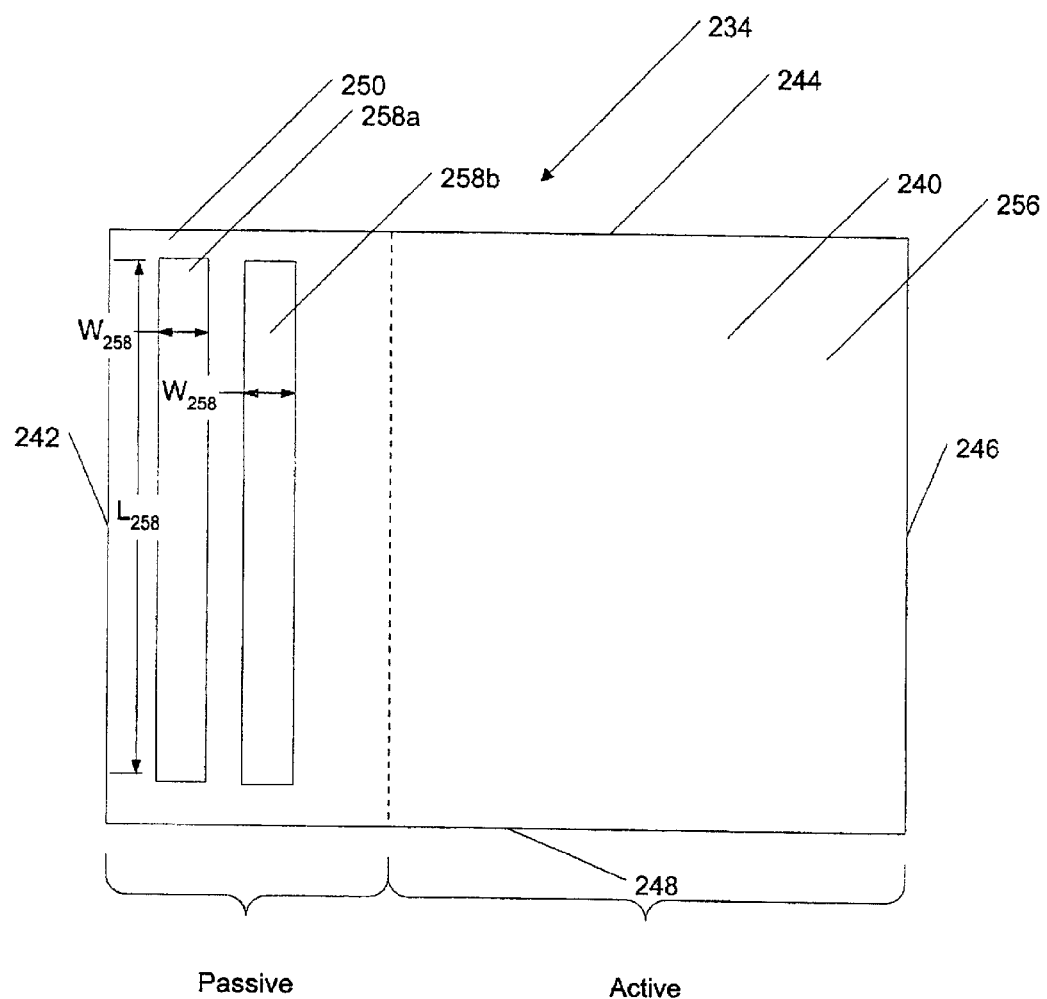
FIG. 2F is a bottom view of an alternate embodiment of the mass of the apparatus of FIG. 2A.

Referring to FIG. 2F, in an alternate embodiment, there is a bond pad 258a and a bond pad 258b that are substantially equal in size and horizontally proximate to each other. The bond pads 258a and 258b may be used for, for example, solder, glass frit, conductive epoxy, or non-conductive epoxy bonding. In a preferred embodiment, the bond pads 258a and 258b are used for solder bonding in order to optimally provide good manufacturability. The bond pads 258*a* and 258*b* preferably have an approximately rectangular cross-sectional shape. The length $L_{258}$ of the bond pads 258*a* and 258*b* may range, for example, from about 180 to 240 mils. In a preferred embodiment, the length $L_{258}$ of the bond pads 258*a* and 258*b* range from about 200 to 220 mils in order to optimally minimize thermal stresses. The width $W_{258}$ of the bond pads 258*a* and 258*b* may range, for example, from about 10 to 20 mils. In a preferred embodiment, the width $W_{258}$ of the bond pads 258*a* and 258*b* range from about 13 to 18 mils in order to optimally minimize thermal stresses. The height $H_{258}$ of the bond pads 258*a* and 258*b* may range, for example, from about 0.1 to 1 mils. In a preferred embodiment, the height $H_{258}$ of the bond pads 258*a* and 258*b* range from about 0.24 to 0.72 mils in order to optimally minimize thermal stresses.

The first bond pad 258*a* is preferably located in the passive region 250 of the bottom parallel planar surface 240 of the mass 204. The first bond pad 258*a* may be located a perpendicular distance ranging, for example, from about 5 to 25 mils from the first side 242 of the bottom parallel planar surface 240 of the mass 204 and may be located a perpendicular distance ranging, for example, from about 5 to 25 mils from the second side 244 of the bottom parallel planar surface 240 of the mass 204. The first bond pad 258*a* is preferably located a perpendicular distance ranging from about 7 to 12 mils from the first side 242 of the bottom parallel planar surface 240 of the mass 204 in order to optimally minimize thermal stresses and located a perpendicular distance ranging from about 7 to 12 mils from the second side 244 of the bottom parallel planar surface 240 of the mass 204 in order to optimally minimize thermal stresses.

The second bond pad 258*b* is preferably located in the passive region 250 of the bottom parallel planar surface 240 of the mass 204. The second bond pad 258*b* may be located a perpendicular distance ranging, for example, from about 15 to 45 mils from the first side 242 of the bottom parallel planar surface 240 of the mass 204 and may be located a perpendicular distance ranging, for example, from about 5 to 25 mils from the second side 244 of the bottom parallel planar surface 240 of the mass 204. The second bond pad 258*b* is preferably located a perpendicular distance ranging from about 20 to 30 mils from the first side 242 of the bottom parallel planar surface 240 of the mass 204 in order to optimally minimize thermal stresses and located a perpendicular distance ranging from about 7 to 12 mils from the second side 244 of the bottom parallel planar surface 240 of the mass 204 in order to optimally minimize thermal stresses.

Figure 2G:
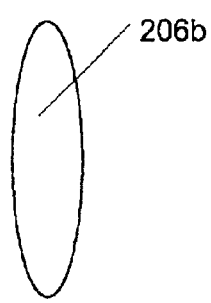
FIG. 2G is a top view of an alternate embodiment of the bond pad of the apparatus of FIG. 2A.

Referring to FIG. 2G, in an alternate embodiment, there is a single bond pad 206*b*. The bond pad 206*b* may have an approximately oval cross-sectional shape. The bond pad 206*b* may have an approximate cross-sectional area ranging from about 4000 to 8750 square mils. In a preferred embodiment, the bond pad 206*b* has an approximate cross-sectional area ranging from about 5625 to 7050 square mils in order to optimally minimize thermal stresses. The height $H_{206}$ of the bond pad 206*b* may range, for example, from about 0.1 to 1 micron. In a preferred embodiment, the height $H_{206}$, of the bond pad 206*b* ranges from about 0.24 to 0.72 microns in order to optimally minimize thermal stresses.

Figure 2H:
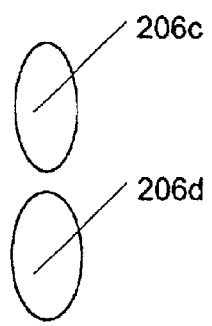
FIG. 2H is a top view of an alternate embodiment of the bond pad of the apparatus of FIG. 2A.

Referring to FIG. 2H, in an alternate embodiment, there is a first bond pad 206*c* and a second bond pad 206*d*. The bond pads 206*c* and 206*d* are substantially equal in size, vertically proximate to each other, and have an approximately oval cross-sectional shape. The bond pads 206*c* and 206*d* may have an approximate total cross-sectional area ranging from about 4000 to 8750 square mils. In a preferred embodiment, the bond pads 206*c* and 206*d* have an approximate total cross-sectional area ranging from about 5625 to 7050 square mils in order to optimally minimize thermal stresses. The height $H_{206}$, of the bond pads 206*c* and 206*d* may range, for example, from about 0.1 to 1 micron. In a preferred embodiment, the height $H_{206}$ of the bond pads 206*c* and 206*d* range from about 0.24 to 0.72 microns in order to optimally minimize thermal stresses.

Figure 2J:
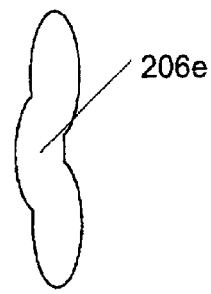
FIG. 2J is a top view of an alternate embodiment of the bond pad of the apparatus of FIG. 2A.

Referring to FIG. 2J, in an alternate embodiment, there is a single bond pad 206*e*. The bond pad 206*e* has an approximately tri-oval cross-sectional shape. The bond pad 206*e* may have approximate cross-sectional area ranging from about 4000 to 8750 square mils. In a preferred embodiment, the bond pad 206*e* has an approximate cross-sectional area ranging from about 5625 to 7050 square mils in order to optimally minimize thermal stresses. The height $H_{206}$ of the bond pad 206*e* may range, for example, from about 0.1 to 1 micron. In a preferred embodiment, the height $H_{206}$ of the bond pad 206*e* ranges from about 0.24 to 0.72 microns in order to optimally minimize thermal stresses.

Figure 2K:
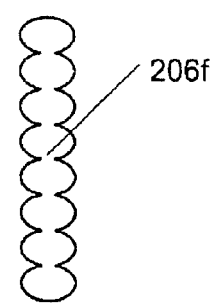
FIG. 2K is a top view of an alternate embodiment of the bond pad of the apparatus of FIG. 2A.

Referring to FIG. 2K, in an alternate embodiment, there is a single bond pad 206*f*. The bond pad 206*f* has an approximately oct-oval cross-sectional shape. The bond pad 206*f* may have an approximate cross-sectional area ranging from about 4000 to 8750 square mils. In a preferred embodiment, the bond pad 206*f* has an approximate cross-sectional area ranging from about 5625 to 7050 square mils in order to optimally minimize thermal stresses. The height $H_{206}$ of the bond pad 206*f* may range, for example, from about 0.1 to 1 micron. In a preferred embodiment, the height $H_{206}$ of the bond pad 206*f* ranges from about 0.24 to 0.72 microns in order to optimally minimize thermal stresses.

Figure 2L:
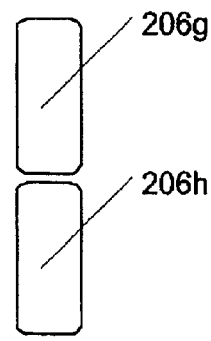
FIG. 2L is a top view of an alternate embodiment of the bond pad of the apparatus of FIG. 2A.

Referring to FIG. 2L, in an alternate embodiment, there is a bond pad 206*g* and a bond pad 206*h*. The bond pads 206*g* and 206*h* are substantially equal in size, vertically proximate to each other, and have an approximately rectangular cross-sectional shape. The bond pads 206*g* and 206*h* may have an approximate total cross-sectional area ranging from about 4000 to 8750 square mils. In a preferred embodiment, the bond pads 206*g* and 206*h* have an approximate total cross-sectional area ranging from about 5625 to 7050 square mils in order to optimally provide minimize thermal stresses. The height $H_{206}$ of the bond pads 206*g* and 206*h* may range, for example, from about 0.1 to 1 micron. In a preferred embodiment, the height $H_{211}$ of the bond pads 206*g* and 206*h* ranges from about 0.24 to 0.72 microns in order to optimally minimize thermal stresses.

Figure 2M:
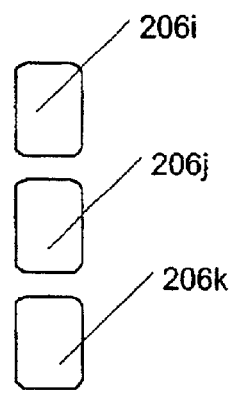
FIG. 2M is a top view of an alternate embodiment of the bond pad of the apparatus of FIG. 2A.

Referring to FIG. 2M, in an alternate embodiment, there is a bond pad 206*i*, a bond pad 206*j*, and a bond pad 206*k*. The bond pads 206*i*, 206*j*, and 206*k* are substantially equal in size, vertically proximate to each other, and have an approximately rectangular cross-sectional shape. The bond pads 206*i*, 206*j*, and 206*k* may have an approximate total cross-sectional area ranging from about 4000 to 8750 square mils. In a preferred embodiment, the bond pads 206*i*, 206*j*, and 206*k* have an approximate total cross-sectional area ranging from about 5625 to 7050 square mils in order to optimally minimize thermal stresses. The height $H_{206}$ of the bond pads 206*i*, 206*j*, and 206*k* may range, for example, from about 0.1 to 1 micron. In a preferred embodiment, the height $H_{206}$ of the bond pads 206*i*, 206*j*, and 206*k* range from about 0.24 to 0.72 microns in order to optimally minimize thermal stresses.

Figure 2N:
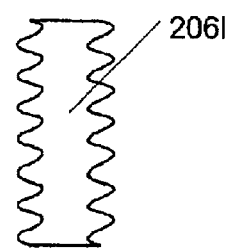
FIG. 2N is a top view of an alternate embodiment of the bond pad of the apparatus of FIG. 2A.

Referring to FIG. 2N in an alternate embodiment, there is a single bond pad 206*l*. The bond pad 206*l* may have an approximately wavy sided rectangular cross-sectional shape. The bond pad 206l may have an approximate cross-sectional area ranging from about 4000 to 8750 square mils. In a preferred embodiment, the bond pad 206l has an approximate cross-sectional area ranging from about 5625 to 7050 square mils in order to optimally minimize thermal stresses. The height $H_{206}$ of the bond pad 206l may range, for example, from about 0.1 to 1 microns. In a preferred embodiment, the height $H_{206}$ of the bond pad 206l ranges from about 0.24 to 0.72 microns in order to optimally minimize thermal stresses.

Figure 2P:
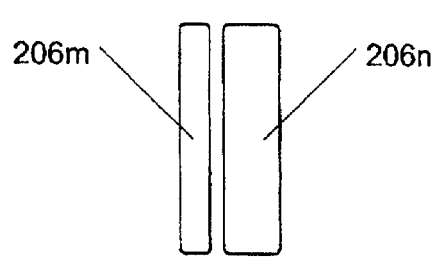
FIG. 2P is a top view of an alternate embodiment of the bond pad of the apparatus of FIG. 2A.

Referring to FIG. 2P, in an alternate embodiment, there is a bond pad 206m and a bond pad 206n. The bond pads 206m and 206n are horizontally proximate to each other and have an approximately rectangular cross-sectional shape. The bond pad 206m is approximately smaller in size than the bond pad 206n. The bond pads 206m and 206n may have an approximate total cross-sectional area ranging from about 4000 to 8750 square mils. In a preferred embodiment, the bond pads 206m and 206n have an approximate total cross-sectional area ranging from about 5625 to 7050 square mils in order to optimally minimize thermal stresses. The height $H_{206}$ of the bond pads 206m and 206n may range, for example, from about 0.1 to 1 micron. In a preferred embodiment, the height $H_{206}$ of the bond pads 206m and 206n range from about 0.24 to 0.72 microns in order to optimally minimize thermal stresses.

Figure 2Q:
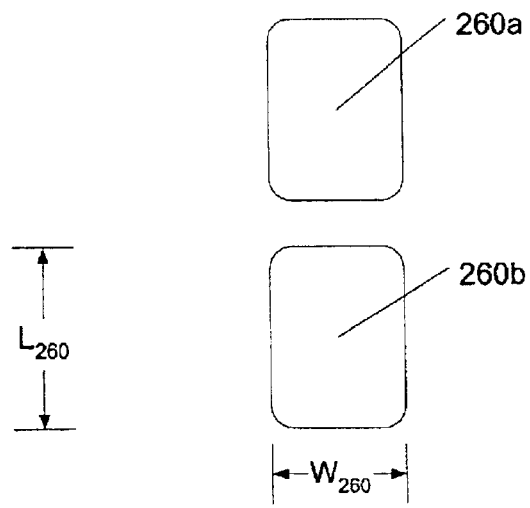
FIG. 2Q is a top view of an alternate embodiment of the resilient coupling of the apparatus of FIG. 2A.
Figure 2R:
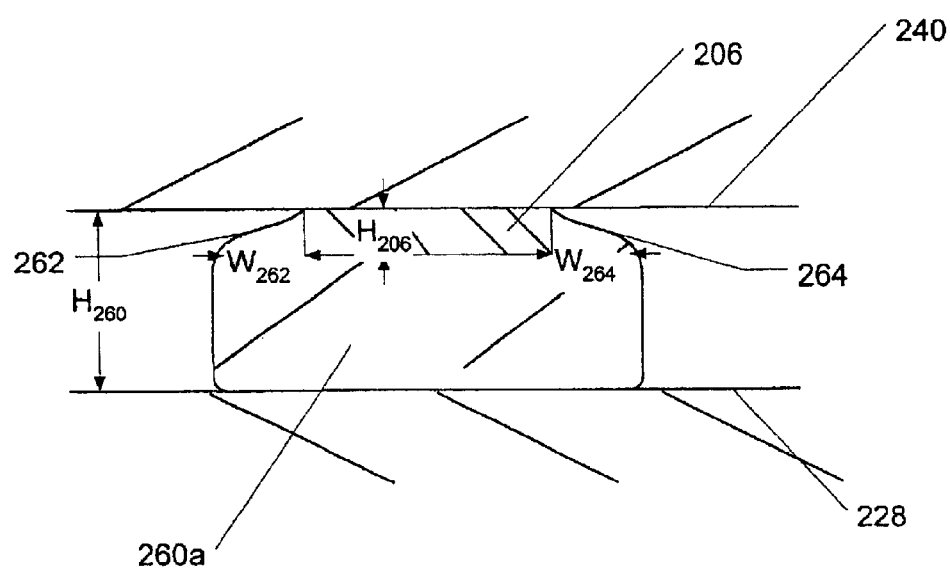
FIG. 2R is a detailed view of the alternate embodiment of the resilient coupling of FIG. 2Q.
Figure 2S:
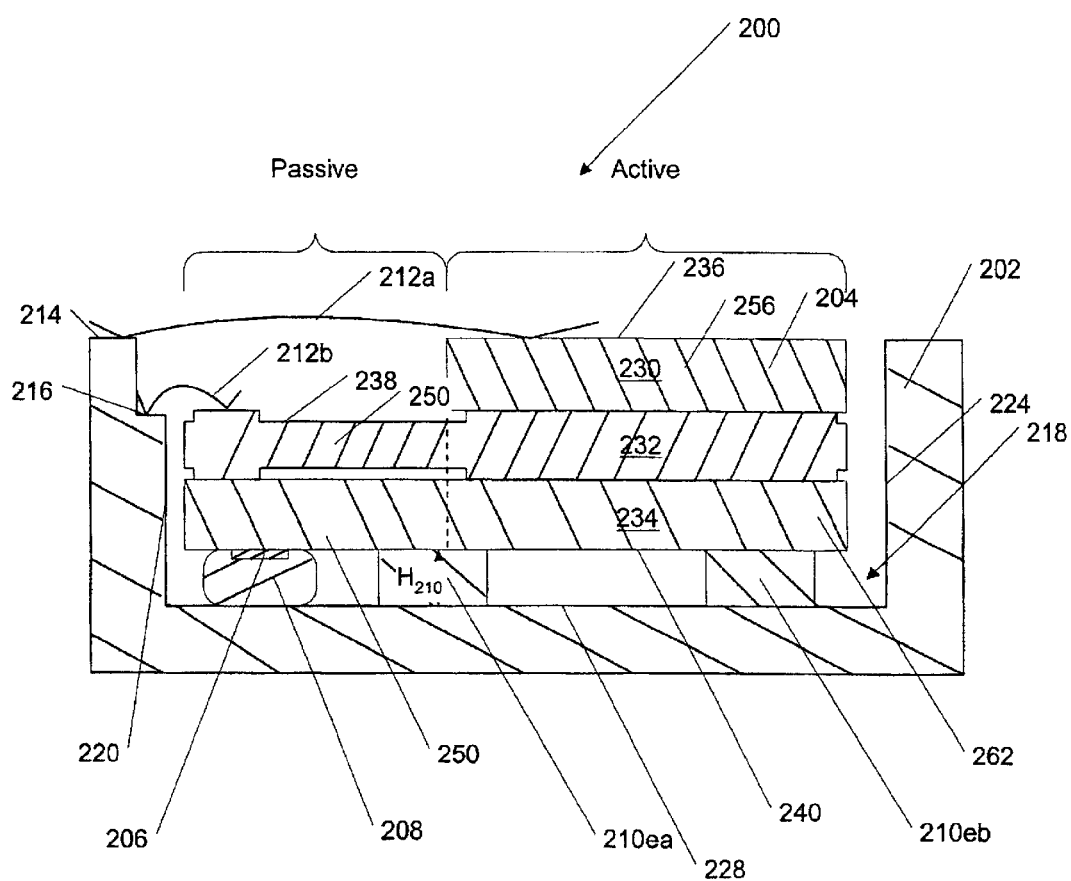
FIG. 2S is a cross-sectional view illustrating an alternate embodiment of an apparatus for resiliently attaching a mass to a package.
Figure 2T:
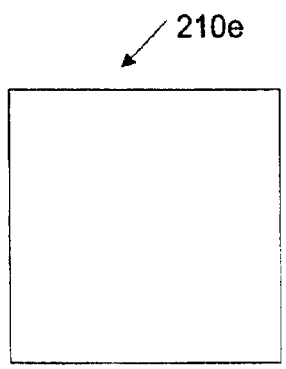
FIG. 2T is a top view of an embodiment of the sliding supports of the apparatus of FIG. 2S.
Figure 2U:
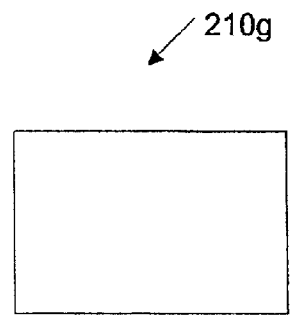
FIG. 2U is a top view of an alternate embodiment of the sliding supports of the apparatus of FIG. 2S.
Figure 2V:
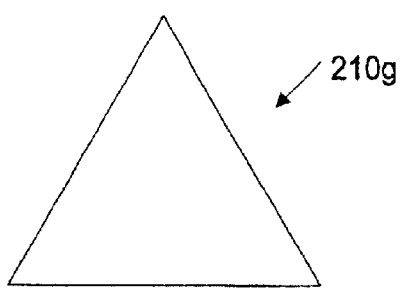
FIG. 2V is a top view of an alternate embodiment of the sliding supports of the apparatus of FIG. 2S.
Figure 2W:
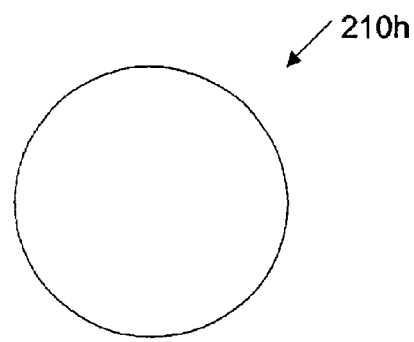
FIG. 2W is a top view of an alternate embodiment of the sliding supports of the apparatus of FIG. 2S.

Referring to FIGS. 2Q and 2R, in an alternate embodiment, there is a first resilient coupling 260a and a second resilient coupling 260b. In a preferred embodiment, the resilient couplings 260a and 260b are solder preforms preferably having an approximately rectangular cross-sectional shape. The resilient couplings 260a and 260b are vertically proximate to each other and substantially equal in size. The resilient couplings 260a and 260b may be any number of conventional commercially available solder preforms of the type, for example, eutectic or non-eutectic. In a preferred embodiment, the resilient couplings 260a and 260b are a eutectic type in order to optimally provide good yield strength with a reasonable melt temperature. The length $L_{260}$ of the resilient couplings 260a and 260b may range, for example, from about 90 to 120 mils. In a preferred embodiment, the length $L_{260}$ of the resilient couplings 260a and 260b ranges from about 101 to 112 mils in order to optimally minimize thermal stresses. The width $W_{260}$ of the resilient couplings 260a and 260b may range, for example, from about 20 to 35 mils. In a preferred embodiment, the width $W_{260}$ of the resilient couplings 260a and 260b ranges from about 25 to 30 mils in order to optimally minimize thermal stresses. The height $H_{206}$ of the resilient couplings 260a and 260b may range, for example, from about 2 to 4 mils. In a preferred embodiment, the height $H_{260}$ of the resilient couplings 260a and 260b ranges from about 2.5 to 3 mils in order to optimally minimize thermal stresses. In a preferred embodiment, the resilient couplings 260a and 260b are coupled to the bottom surface 228 of the cavity 218 of the package 202 using conventional solder equipment and processes. In a preferred embodiment, the resilient couplings 260a and 260b are coupled to the bond pads 206 using conventional solder equipment and processes.

The first resilient coupling 260a may be located a perpendicular distance ranging, for example, from about 5 to 25 mils from the first wall 220 of the cavity 218 of the package 202 and may be located a perpendicular distance ranging, for example, from about 5 to 25 mils from the second wall 222 of the cavity 218 of the package 202. In a preferred embodiment, the first resilient coupling 260a is located a perpendicular distance ranging from about 7 to 12 mils from the first wall 220 of the cavity 218 of the package 202 in order to optimally minimize thermal stresses and located a distance ranging from about 7 to 12 mils from the second wall 222 of the cavity 218 of the package 202 in order to optimally minimize thermal stresses.

The second resilient coupling 260b may be located a perpendicular distance ranging, for example, from about 5 to 25 mils from the first wall 220 of the cavity 218 of the package 202 and may be located a perpendicular distance ranging, for example, from about 105 to 145 mils from the second wall 222 of the cavity 218 of the package 202. In a preferred embodiment, the second resilient coupling 260b is located a perpendicular distance ranging from about 7 to 12 mils from the first wall 228 of the cavity 218 of the package 202 in order to optimally minimize thermal stresses and located a distance ranging from about 112 to 127 mils from the second wall 222 of the cavity 218 of the package 202 in order to optimally minimize thermal stresses.

In a preferred embodiment, the resilient couplings 260a and 260b further include one or more first bumpers 262 for slidingly supporting the mass 204. In a preferred embodiment, the first bumpers 262 are located on one side of the bond pads 206. In a preferred embodiment, the first bumpers 262 are proximate to the bond pads 206. The width $W_{262}$ of the first bumpers 262 may range, for example, from about 2 to 6 mils. In a preferred embodiment, the width $W_{262}$ of the first bumpers 262 range from about 3 to 5 mils in order to optimally minimize thermal stresses. In a preferred embodiment, there is a single first bumper 262.

In a preferred embodiment, the resilient couplings 260a and 260b further include one or more second bumpers 264 for slidingly supporting the mass 204. In a preferred embodiment, the second bumpers 264 are located on another side of the bond pads 206 opposite the first bumpers 262. In a preferred embodiment, the second bumpers 264 are proximate to the bond pads 206. The width $W_{264}$ of the second bumpers 264 may range, for example, from about 2 to 6 mils. In a preferred embodiment, the width $W_{264}$ of the second bumpers 264 range from about 3 to 5 mils in order to optimally minimize thermal stresses. In a preferred embodiment, there is a single second bumper 264.

Referring to FIGS. 2S through 2W, in an alternate embodiment, the system 200 further includes one or more sliding supports 210e, 210f, 210g, or 210h. The sliding supports 210e, 210f, 210g, or 210h preferably slidingly support the mass 204. The number of sliding supports 210e, 210f, 210g, or 210h preferably depends upon having a sufficient amount of sliding supports in order to optimally slidingly support the mass 204. The sliding supports 210e, 210f, 210g, or 210h are preferably coupled to the bottom surface 228 of the cavity 218 of the package 202. The sliding supports 210e may have an approximately square cross sectional shape. The sliding supports 210f may have an approximately rectangular cross-sectional shape. The sliding supports 210g may have an approximately triangular croosectional shape. The sliding supports 210h may have an approximately circular shape. The sliding supports 210e, 210f, 210g, or 210h may, for example, be tungsten or ceramic. In a preferred embodiment, the sliding supports 210e, 210f, 210g, or 210h are tungsten in order to optimally provide a standard packaging process. In a preferred embodiment, the sliding supports 210e, 210f, 210g, or 210h are coupled to the bottom surface 228 of the cavity 218 of the package 202 using conventional means of integrating the sliding supports 210e, 210f, 210g, or 210h into the package 202.

The sliding supports 210e, 210f, 210g, or 210h may have an approximate cross-sectional area ranging from about 400 to 1600 square mils, individually. In a preferred embodiment, the sliding supports 210e, 210f, 210g, or 210h have an approximate cross-sectional area ranging from about 625 to 1225 square mils, individually, in order to optimally minimize thermal stresses. The height $H_{210}$ of the sliding supports 210e, 210f, 210g, or 210h may range, for example, from about 0.5 to 3 mils. In a preferred embodiment, the height $H_{210}$ of the sliding supports 210e, 210f, 210g, or 210h ranges from about 1 to 1.5 mils in order to optimally minimize thermal stresses.

In a preferred embodiment, there is a first sliding support 210ea, a second sliding support 210eb, a third sliding support 210ec, and a fourth sliding support 210ed. The first sliding support 210ea may be located a perpendicular distance ranging, for example, from about 45 to 75 mils from the first wall 220 of the cavity 218 of the package 202 and may be located a perpendicular distance ranging, for example, from about 85 to 115 mils from the second wall 222 of the cavity 218 of the package 202. In a preferred embodiment, the first sliding support 210ea is located a perpendicular distance ranging from about 52 to 62 mils from the first wall 220 of the cavity 218 of the package 202 in order to optimally minimize thermal stresses and located a perpendicular distance from about 90 to 105 mils from the second wall 222 of the cavity 218 of the package 202 in order to optimally minimize thermal stresses.

The second sliding support 210eb may be located a perpendicular distance ranging, for example, from about 45 to 75 mils from the first wall 220 of the cavity 218 of the package 202 and may be located a perpendicular distance ranging, for example, from about 15 to 30 mils from the second wall 222 of the cavity 218 of the package 202. In a preferred embodiment, the second sliding support 210eb is located a perpendicular distance ranging from about 52 to 62 mils from the first wall 220 of the cavity 218 of the package 202 in order to optimally minimize thermal stresses and located a perpendicular distance ranging from about 20 to 25 mils from the second wall 222 of the cavity 218 of the package 202 in order to optimally minimize thermal stresses.

The third sliding support 210ec may be located a perpendicular distance ranging, for example, from about 85 to 115 mils from the first wall 220 of the cavity 218 of the package 202 and may be located a perpendicular distance ranging, for example, from about 15 to 30 mils from the second wall 222 of the cavity 218 of the package 202. In a preferred embodiment, the third sliding support 210ec is located a perpendicular distance ranging from about 90 to 105 mils from the first wall 220 of the cavity 218 of the package 202 in order to optimally minimize thermal stresses and located a perpendicular distance ranging from about 20 to 25 mils from the second wall 222 of the cavity 218 of the package 202 in order to optimally minimize thermal stresses.

The fourth sliding support 210ed may be located a perpendicular distance ranging, for example, from about 85 to 115 mils from the first wall 220 of the cavity 218 of the package 202 and may be located a perpendicular distance ranging, for example, from about 85 to 115 mils from the second wall 222 of the cavity 218 of the package 202. In a preferred embodiment, the fourth sliding support 210ed is located a perpendicular distance ranging from about 90 to 105 mils from the first wall 220 of the cavity 218 of the package 202 in order to optimally minimize thermal stresses and located a perpendicular distance ranging from about 90 to 105 mils from the second wall 222 of the cavity 218 of the package 202 in order to optimally minimize thermal stresses.

In an alternate embodiment, the resilient couplings 208 may also electrically couple the mass 204 to the package 202.

In an alternate embodiment, the resilient couplings 260a and 260b may also electrically couple the mass 204 to the package 202.

Referring to FIGS. 3A through 3E, an embodiment of a system 300 for resiliently coupling a mass to a package preferably includes a package 302, a mass 304, one or more bond pads 306, one or more resilient couplings 308, and one or more electrical connections 310.

The package 302 is coupled to the resilient couplings 308 and the electrical connections 310. The package 302 may be, for example, a housing or a substrate. In a preferred embodiment, the package 302 is a housing in order to optimally provide a surface mount component. The package 302 preferably includes a top parallel planar surface 312 and a cavity 314. The cavity 314 preferably includes a first wall 316, a second wall 318, a third wall 320 and a fourth wall 322. The first wall 316 and the third wall 320 are preferably approximately parallel to each other and the second wall 318 and the fourth wall 322 are preferably approximately parallel to each other. The second wall 318 and the fourth 322 wall are also preferably perpendicular to the first wall 316 and the third wall 320. The cavity 314 preferably includes a bottom surface 324. The package 302 may be any number of conventional commercially available housings of the type, for example, ceramic, metal or plastic. In a preferred embodiment, the package 302 is ceramic in order to optimally provide vacuum sealing of the mass 304 within the package 302.

The mass 304 is preferably resiliently attached to the package 302 by the resilient couplings 308 and electrically coupled to the package 302 by the electrical connections 310. The mass 304 preferably has an approximately rectangular cross-sectional shape. The mass 304 preferably includes all active regions. In a preferred embodiment, the mass 304 is a micro machined sensor substantially as disclosed in copending U.S. patent application Ser. No. 09/936,640, filed on Sep. 12, 2001, the disclosure of which is incorporated herein by reference.

In a preferred embodiment, the mass 304 includes a top parallel planar surface 338 and a bottom parallel planar surface 340. The bottom parallel planar surface 340 of the mass 304 preferably includes a first side 342, a second side 344, a third side 346, and a fourth side 348. The first side 342 and the third side 346 are preferably approximately parallel to each other and the second side 344 and the fourth side 348 are preferably approximately parallel to each other and preferably approximately perpendicular to the first side 342 and the third side 346.

In a preferred embodiment, the bottom parallel planar surface 340 of the mass 304 includes the bond pads 306. In a preferred embodiment, the bond pads 306 are located substantially in the center of the bottom parallel planar surface 340 of the mass 304. The bond pads 306 may be located a perpendicular distance ranging, for example, from about 80 to 100 mils from the first side 342 of the bottom parallel planar surface 340 of the mass 304 and may be located a perpendicular distance ranging, for example, from about 80 to 100 mils from the second side 344 of the bottom parallel planar surface 340 of the mass 304. In a preferred embodiment, the bond pads 306 are located a perpendicular distance ranging from about 85 to 95 mils from the first side 342 of the bottom parallel planar surface 340 of the mass 304 in order to optimally minimize thermal stresses and located a perpendicular distance ranging from about 85 to 95 mils from the second side 344 of the bottom parallel planar surface 340 of the mass 304 in order to optimally minimize thermal stresses. The bond pads 306 may be, for example, used for solder, glass frit, conductive epoxy, or non-conductive epoxy bonding. In a preferred embodiment, the bond pads 306 are used for solder bonding in order to optimally provide good manufacturability. In a preferred embodiment, the bond pads 306 contact area is maximized in order to optimize the shock tolerance of the mass 304. In a preferred embodiment, the bond pads 306 have minimal discontinuities in order to optimize the distribution of thermal stresses in the mass 304. In several alternate embodiments, there is a plurality of bond pads 306 in order to optimize the relief of thermal stresses in the mass 304. In a preferred embodiment, there is a single bond pad 306a. The bond pad 306a preferably has an approximately circular cross-sectional shape. The diameter $D_{306a}$ of the bond pad 306a may range, for example, from about 50 to 100 mils. In a preferred embodiment, the diameter $D_{306a}$ of the bond pad 306a ranges from about 70 to 80 mils in order to optimally minimize thermal stresses. The height 306 of the bond pad 306 may range, for example, from about 0.1 to 1 micron. In a preferred embodiment, the height $H_{306}$ of the bond pad 306 ranges from about 0.24 to 0.72 microns in order to optimally minimize thermal stresses.

The resilient couplings 308 preferably resiliently attach the bond pads 306 to the package 302. The resilient couplings 308 are preferably coupled to the bottom surface 324 of the cavity 314. In a preferred embodiment, the resilient couplings 308 are solder preforms. In a preferred embodiment, the resilient couplings 308 have an approximate cross-sectional circular shape. In a preferred embodiment, the resilient couplings 308 have minimal discontinuities in order to optimize the distribution of thermal stresses. In several alternate embodiments, there is a plurality of resilient couplings 308 in order to optimize the relief of thermal stresses in the mass 304. The resilient couplings 308 may be any number of conventional commercially available solder preforms of the type, for example, eutectic or non-eutectic. In a preferred embodiment, the resilient couplings 308 are a eutectic type in order to optimally provide good yield strength with a reasonable melt temperature. The resilient couplings 308 may be located a perpendicular distance ranging, for example, from about 80 to 100 mils from the first wall 316 of the cavity 314 of the package 302 and may be located a perpendicular distance ranging, for example, from about 80 to 100 mils from the second wall 318 of the cavity 314 of the package 302. In a preferred embodiment, the resilient couplings 308 are located a perpendicular distance ranging from about 85 to 95 mils from the first wall 316 of the cavity 314 of the package 302 in order to optimally minimize thermal stresses and located a distance ranging from about 85 to 95 mils from the second wall 318 of the cavity 314 of the package 302 in order to optimally minimize thermal stresses. In a more preferred embodiment, there is a single resilient coupling 308. The diameter $D_{308}$ of the resilient coupling 308 may range, for example, from about 50 to 100 mils. In a preferred embodiment, the diameter $D_{308}$ of the resilient coupling 308 ranges from about 70 to 80 mils in order to optimally minimize thermal stresses. The height $H_{308}$, of the resilient coupling 308 may range, for example, from about 2 to 4 mils. In a preferred embodiment, the height $H_{308}$ of the resilient coupling 308 ranges from about 2.5 to 3 mils in order to optimally minimize thermal stresses.

In a preferred embodiment, the resilient coupling 308 further includes one or more bumpers 350 for slidingly supporting the mass 304. In a preferred embodiment, there is a single bumper 350. In a preferred embodiment, the bumper 350 has an approximately annular cross-sectional shape. In a preferred embodiment, the bumper 350 surrounds the bond pads 306. In a preferred embodiment, the bumper 350 is proximate to the bond pads 306. The width $W_{350}$ of the bumper 350 may range, for example, from about 2 to 6 mils. In a preferred embodiment, the width $W_{350}$ of the bumper 350 ranges from about 3 to 5 mils in order to optimally minimize thermal stresses. In a preferred embodiment, the resilient couplings 308 are coupled to the bond pad 306 using conventional solder equipment and processes. In a preferred embodiment, the resilient couplings 308 are coupled to the bottom surface 324 of the cavity 314 of the package 302 using conventional solder equipment and processes.

The electrical connections 310 preferably electrically couple the mass 304 to the package 302. In a preferred embodiment, there is a single electrical connection 310. The electrical connection 310 preferably electrically couples the top parallel planar surface 312 of the package 302 to the top parallel planar surface 338 of the mass 304. In a preferred embodiment, the electrical connection 310 is a wire bond. The electrical connection 310 may be any number of conventional commercially available wire bonds of the type, for example, gold or aluminum. In a preferred embodiment, the electrical connection 310 is gold in order to optimally provide compatibility with the package 302 and the mass 304 metallization. In a preferred embodiment, the electrical connection 310 is coupled to the package 302 using conventional wire-bonding equipment and processes. In a preferred embodiment, the electrical connection 310 is coupled to the mass 304 using conventional wire-bonding equipment and processes.

Figure 3A:
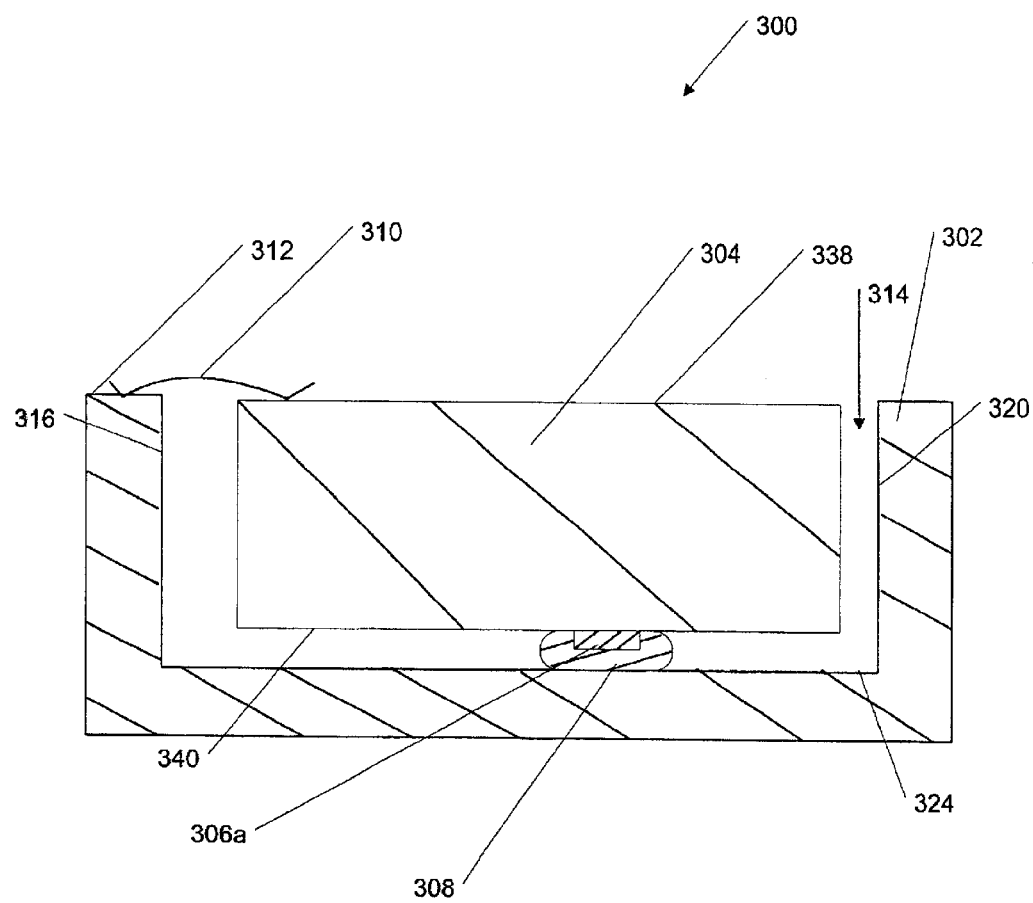
FIG. 3A is a cross-sectional view illustrating an embodiment of an apparatus for resiliently attaching a mass to a package.
Figure 3B:
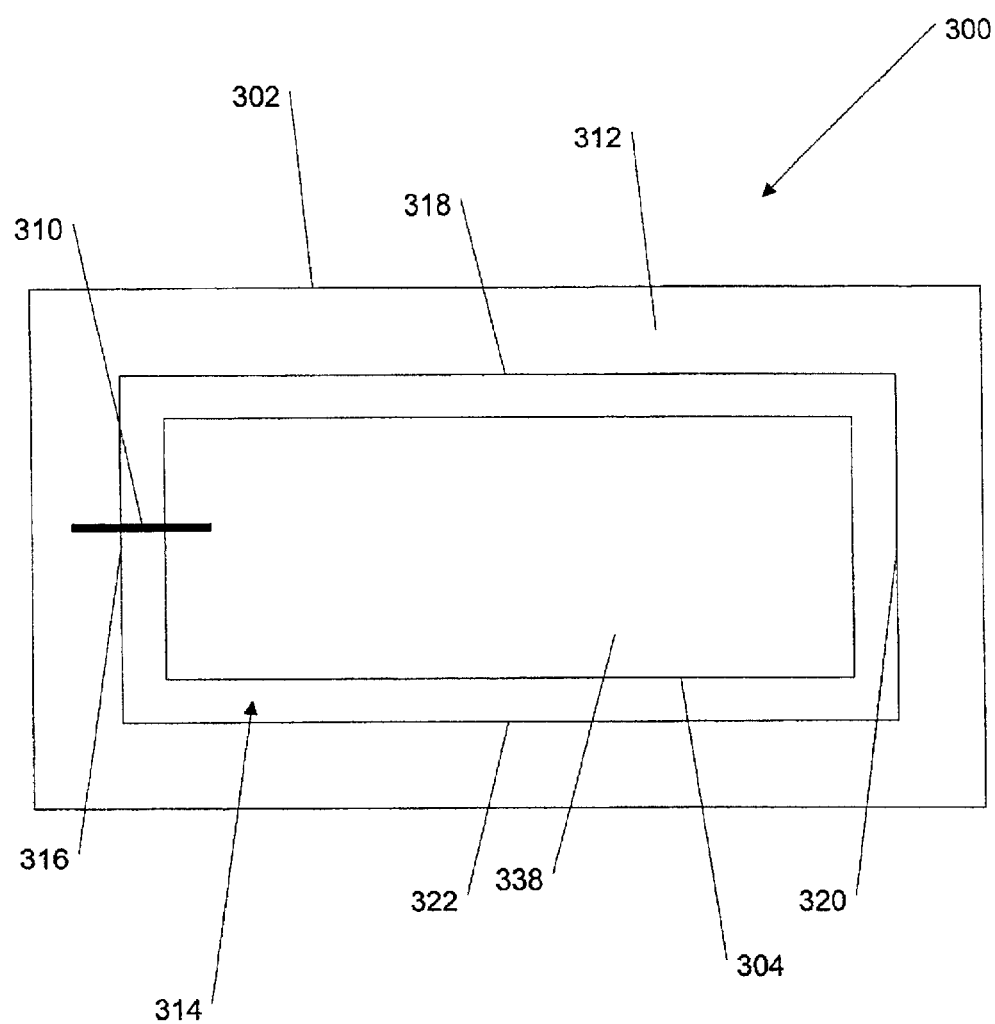
FIG. 3B is a top view of an embodiment of the apparatus of FIG. 3A.
Figure 3C:
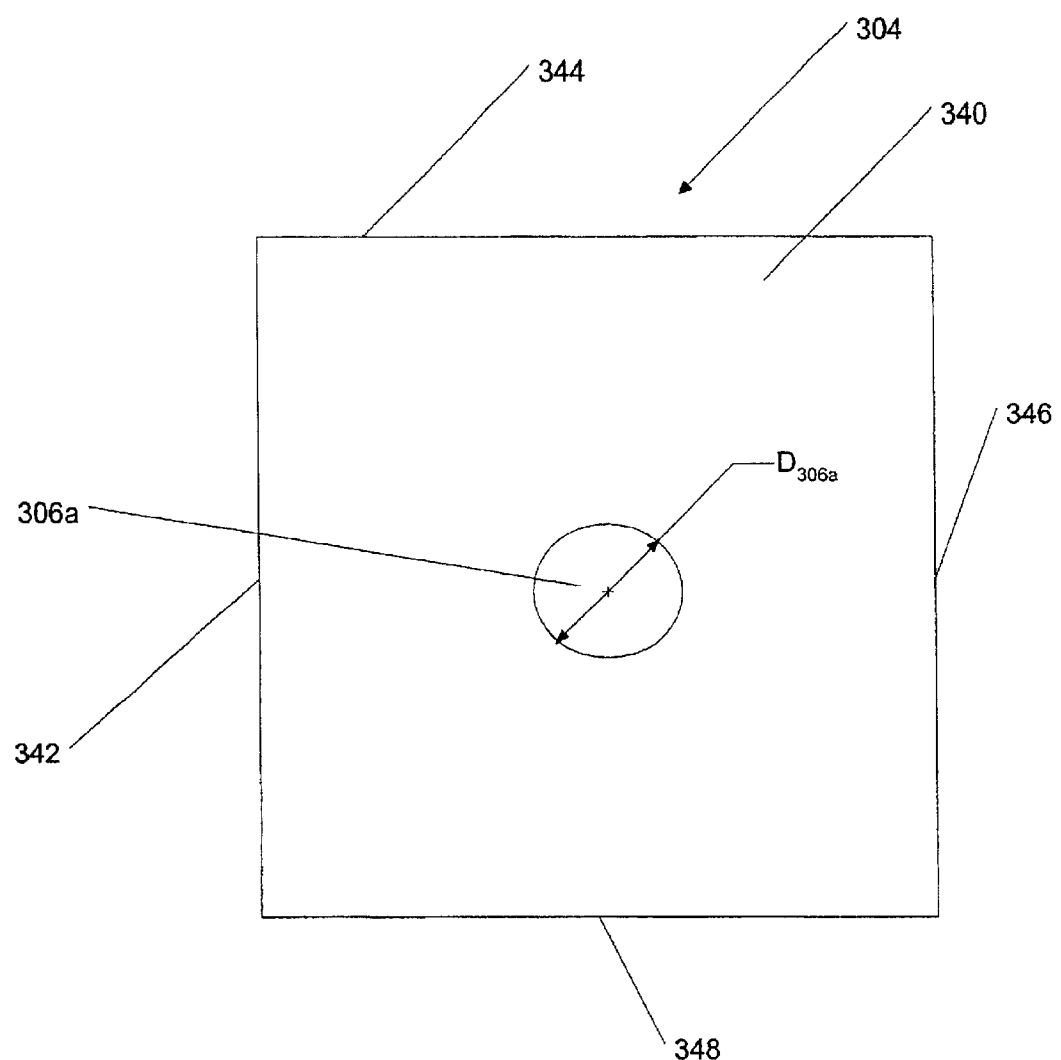
FIG. 3C is a bottom view of an embodiment of the mass of the apparatus of FIG. 3A.
Figure 3D:
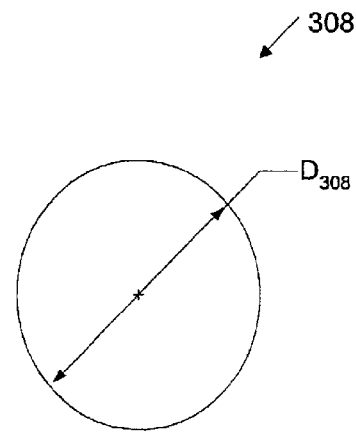
FIG. 3D is a top view of an embodiment of the resilient coupling of the apparatus of FIG. 3A.
Figure 3E:
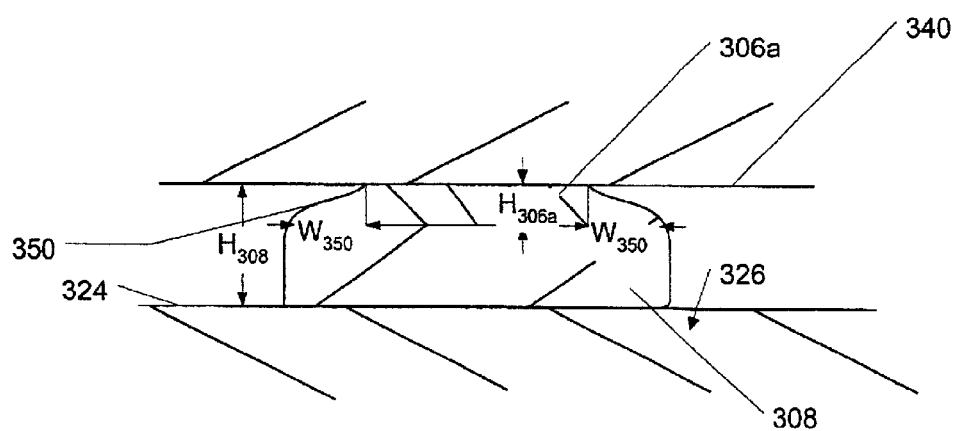
FIG. 3E is a detailed view of the embodiment of the resilient coupling of FIG. 3D.
Figure 3F:
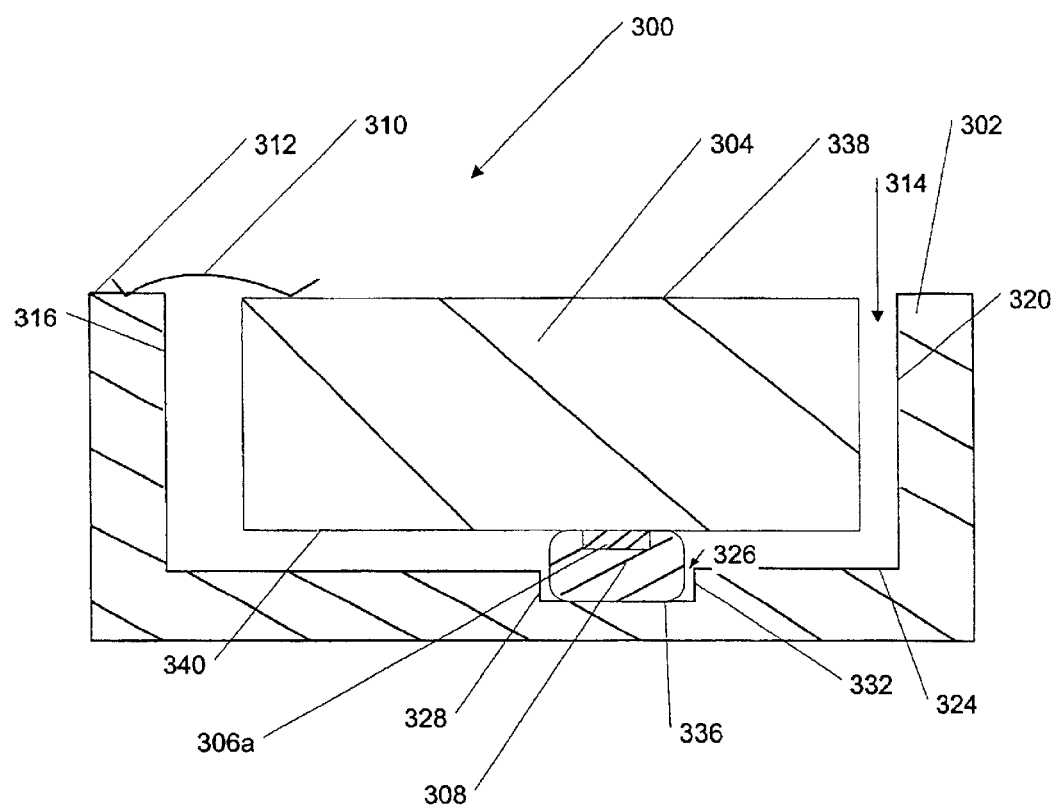
FIG. 3F is a cross-sectional view illustrating an alternate embodiment of an apparatus for resiliently attaching a mass to a package.

Referring to FIG. 3F, in an alternate embodiment, the bottom surface 324 of the package 302 further includes a recess 326 for receiving the resilient coupling 308. The recess 326 may be circular or square in shape. The recess 326 preferably includes a first wall 328, a second wall 330, a third wall 332 and a fourth wall 334. The first wall 328 and the third wall 332 are preferably approximately parallel to each other and the second wall 330 and the fourth wall 334 are preferably approximately parallel to each other. The second wall 330 and the fourth wall 334 are also preferably perpendicular to the first wall 328 and the third wall 332. The recess 326 preferably includes a bottom surface 336. The length $L_{326}$ of the recess 326 may range, for example, from about 110 to 130 mils. In a preferred embodiment the length $L_{326}$ of the recess 326 ranges from about 115 to 125 mils in order to optimally minimize thermal stresses. The width $W_{326}$ of the recess 326 may range, for example, from about 110 to 130 mils. In a preferred embodiment the width $W_{326}$ of the recess 326 ranges from about 115 to 125 mils in order to optimally minimize thermal stresses. The height $H_{326}$ of the recess 326 may range, for example, from about 1 to 2 mils. In a preferred embodiment the height $H_{326}$ of the recess 326 ranges from about 1.25 to 1.75 mils in order to optimally minimize thermal stresses. In a preferred embodiment, the recess 326 is located substantially in the center of the bottom surface 324 of the package 302. The first wall 328 of the recess 326 may be located a perpendicular distance ranging, for example, from 80 to 100 mils from the first wall 316 of the cavity 314. In a preferred embodiment, the first wall 328 of the recess 326 is located a perpendicular distance ranging from 85 to 95 mils from the first wall 316 of the cavity 314 in order to optimally minimize thermal stresses. The second wall 330 of the recess 326 may be located a perpendicular distance ranging, for example, from 80 to 100 mils from the second wall 318 of the cavity 314. In a preferred embodiment, the second wall 330 of the recess 326 is located a perpendicular distance ranging from 85 to 95 mils from the second wall 318 of the cavity 314 in order to optimally minimize thermal stresses.

In a preferred embodiment, the resilient coupling 308 is located in the recess 326. The resilient coupling 308 may be located a perpendicular distance ranging, for example, from about 2 to 7 mils from the first wall 328 of the recess 326 of the cavity 314 of the package 302 and may be located a perpendicular distance ranging, for example, from about 2 to 7 mils from the second wall 330 of the recess 326 of the cavity 314 of the package 302. In a preferred embodiment, the resilient coupling 308 is located a perpendicular distance ranging from about 3 to 5 mils from the first wall 328 of the recess 326 of the cavity 314 of the package 302 in order to optimally minimize thermal stresses and located a distance ranging from about 3 to 5 mils from the second wall 330 of the recess 326 of the cavity 314 of the package 302 in order to optimally minimize thermal stresses. In a preferred embodiment, the resilient coupling 308 is coupled to the bottom surface 324 of the recess 326 using conventional solder equipment and processes.

Figure 3G:
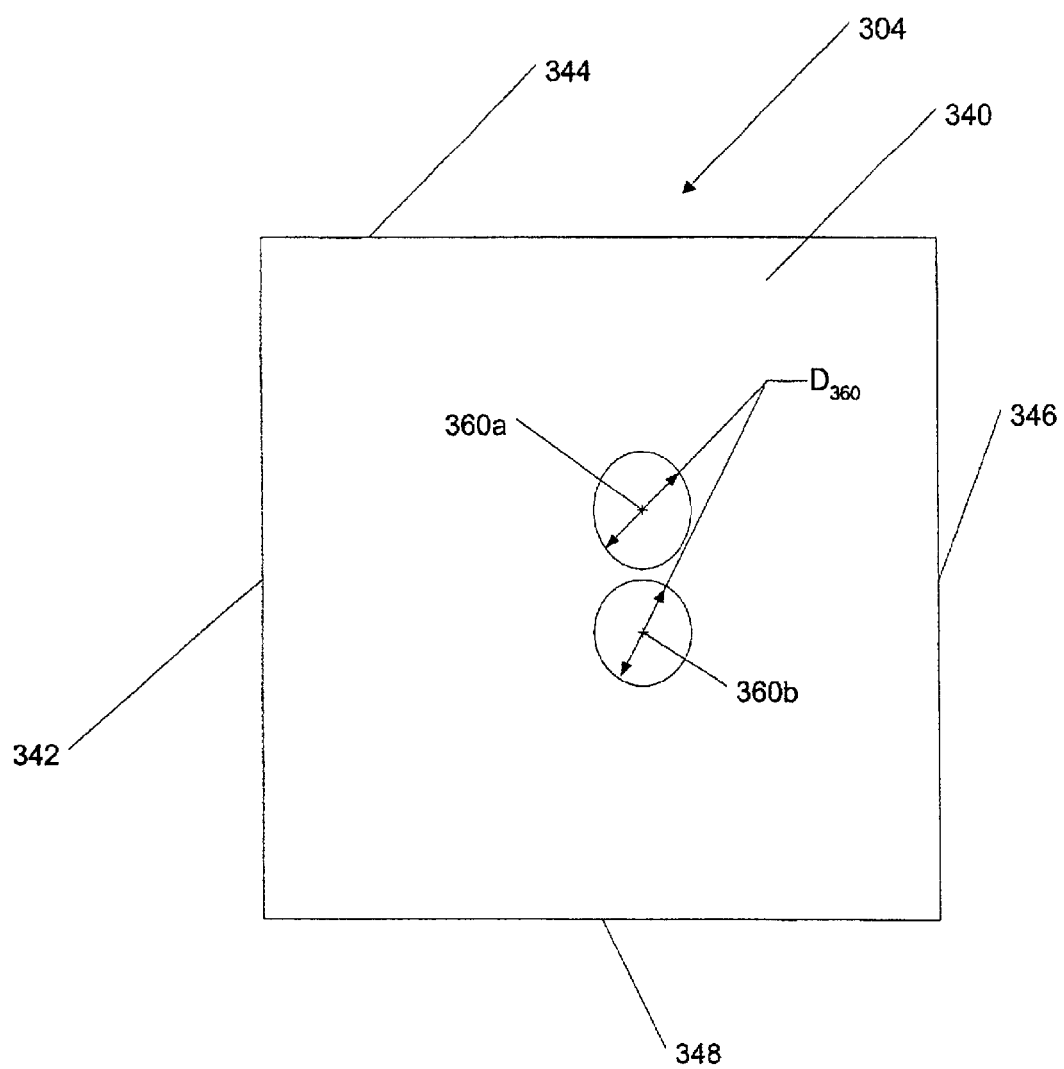
FIG. 3G is a bottom view of an alternate embodiment of the mass of the apparatus of FIG. 3A.

Referring to FIG. 3G, in an alternate embodiment, there is a first bond pad 360a and a second bond pad 360b that are substantially equal in size and vertically proximate to each other. The bond pads 360a and 360b may be used for, for example, solder, glass frit, conductive epoxy, or non-conductive epoxy bonding. In a preferred embodiment, the bond pads 360a and 360b are used for solder bonding in order to optimally provide good manufacturability. The bond pads 360a and 360b preferably have an approximately circular cross-sectional shape. The total diameter $D_{360}$ of the bond pads 360a and 360b may range, for example, from about 50 to 100 mils. In a preferred embodiment, the total diameter $D_{360}$ of the bond pads 360a and 360b ranges from about 70 to 80 mils in order to optimally minimize thermal stresses. The height $H_{360}$ of the bond pads 360a and 360b may range, for example, from about 0.1 to 1 micron. In a preferred embodiment, the height $H_{360}$ of the bond pads 360a and 360b ranges from about 0.24 to 0.72 microns in order to optimally minimize thermal stresses.

The first bond pad 360a is preferably located substantially in the center of the bottom parallel planar surface 340 of the mass 304. The first bond pad 360a may be located a perpendicular distance ranging, for example, from about 80 to 100 mils from the first side 342 of the bottom parallel planar surface 340 of the mass 304 and may be located a perpendicular distance ranging, for example, from about 40 to 50 mils from the second side 344 of the bottom parallel planar surface 340 of the mass 304. The first bond pad 360a is preferably located a perpendicular distance ranging from about 85 to 95 mils from the first side 342 of the bottom parallel planar surface 340 of the mass 304 in order to optimally minimize thermal stresses and located a perpendicular distance ranging from about 43 to 47 mils from the second side 344 of the bottom parallel planar surface 340 of the mass 304 in order to optimally minimize thermal stresses.

The second bond pad 360b is preferably located substantially in the center of the bottom parallel planar surface 340 of the mass 304. The second bond pad 360b may be located a perpendicular distance ranging, for example, from about 80 to 100 mils from the first side 342 of the bottom parallel planar surface 340 of the mass 304 and may be located a perpendicular distance ranging, for example, from about 135 to 165 mils from the second side 344 of the bottom parallel planar surface 340 of the mass 304. The second bond pad 360b is preferably located a perpendicular distance ranging from about 85 to 95 mils from the first side 342 of the bottom parallel planar surface 340 of the mass 304 in order to optimally minimize thermal stresses and located a perpendicular distance ranging from about 143 to 157 mils from the second side 344 of the bottom parallel planar surface 340 of the mass 304 in order to optimally minimize thermal stresses.

Figure 3H:
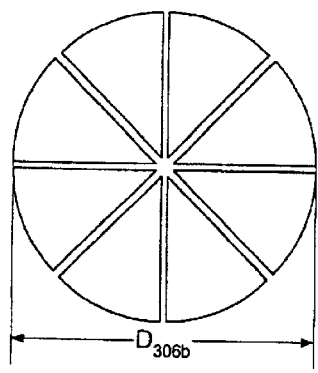
FIG. 3H is a top view of an alternate embodiment of the bond pad of the apparatus of FIG. 3A.

Referring to FIG. 3H, in an alternate embodiment, there is a bond pad 306b. The bond pad 306b may have an approximately oct-pie-wedge cross-sectional shape. The overall diameter $D_{306b}$ of the bond pad 306b may range, for example, from about 50 to 100 mils. In a preferred embodiment, the overall diameter $D_{306b}$ of the bond pad 306b ranges from about 70 to 80 mils in order to optimally minimize thermal stresses. The height $H_{306}$ of the bond pad 306b may range, for example, from about 0.1 to 1 micron. In a preferred embodiment, the height $H_{306}$ of the bond pad 306b ranges from about 0.24 to 0.72 microns in order to optimally minimize thermal stresses.

Figure 3J:
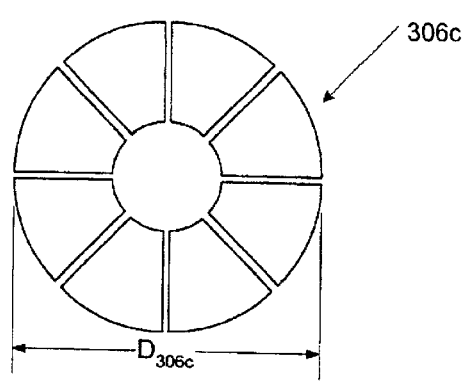
FIG. 3J is a top view of an alternate embodiment of the bond pad of the apparatus of FIG. 3A.

Referring to FIG. 3J, in an alternate embodiment, there is bond pad 306c. The bond pad 306c may have an approximately hollow oct-pie-wedge cross-sectional shape. The overall diameter $D_{306c}$ of the bond pad 306c may range, for example, from about 50 to 100 mils. In a preferred embodiment, the overall diameter $D_{306c}$ of the bond pad 306c ranges from about 70 to 80 mils in order to optimally minimize thermal stresses. The height $H_{306}$ of the bond pad 306c may range, for example, from about 0.1 to 1 micron. In a preferred embodiment, the height $H_{306}$ of the bond pad 306c ranges from about 0.24 to 0.72 microns in order to optimally minimize thermal stresses.

Figure 3K:
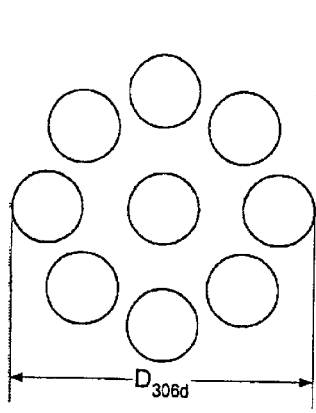
FIG. 3K is a top view of an alternate embodiment of the bond pad of the apparatus of FIG. 3A.

Referring to FIG. 3K, in an alternate embodiment, there is a bond pad 306d. The bond pad 306d has an approximately nine-circular cross-sectional shape. The overall diameter $D_{306d}$ of the bond pad 306d may range, for example, from about 50 to 100 mils. In a preferred embodiment, the overall diameter $D_{306d}$ of the bond pad 306d ranges from about 70 to 80 mils in order to optimally minimize thermal stresses. The height $H_{306}$ of the bond pad 306d may range, for example, from about 0.1 to 1 micron. In a preferred embodiment, the height $H_{306}$ of the bond pad 306d ranges from about 0.24 to 0.72 microns in order to optimally minimize thermal stresses.

Figure 3L:
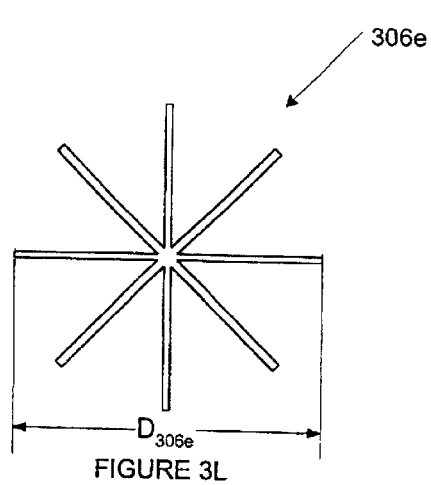
FIG. 3L is a top view of an alternate embodiment of the bond pad of the apparatus of FIG. 3A.

Referring to FIG. 3L, in an alternate embodiment, there is a single bond pad 306e. The bond pad 306e has an approximately starburst cross-sectional shape. The overall diameter $D_{306e}$ of the bond pad 306e may range, for example, from about 50 to 100 mils. In a preferred embodiment, the overall diameter $D_{306e}$ of the bond pad 306e ranges from about 70 to 80 mils in order to optimally minimize thermal stresses. The height $H_{306}$ of the bond pad 306e may range, for example, from about 0.1 to 1 micron. In a preferred embodiment, the height $H_{306}$ of the bond pad 306e ranges from about 0.24 to 0.72 microns in order to optimally minimize thermal stresses.

Figure 3M:
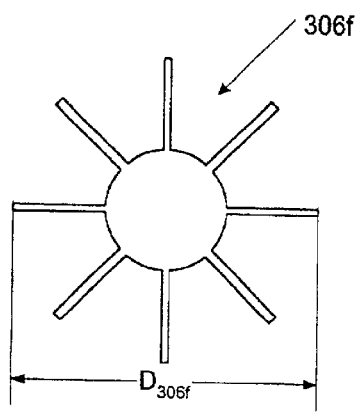
FIG. 3M is a top view of an alternate embodiment of the bond pad of the apparatus of FIG. 3A.

Referring to FIG. 3M in an alternate embodiment, there is a single bond pad 306f. The bond pad 306f has an approximately sunburst cross-sectional shape. The overall diameter $D_{306f}$ of the bond pad 306f may range, for example, from about 50 to 100 mils. In a preferred embodiment, the overall diameter $D_{306f}$ of the bond pad 306f ranges from about 70 to 80 mils in order to optimally minimize thermal stresses. The height $H_{306}$ of the bond pad 306f may range, for example, from about 0.1 to 1 micron. In a preferred embodiment, the height $H_{306}$ of the bond pad 306f ranges from about 0.24 to 0.72 microns in order to optimally minimize thermal stresses.

Figure 3R:
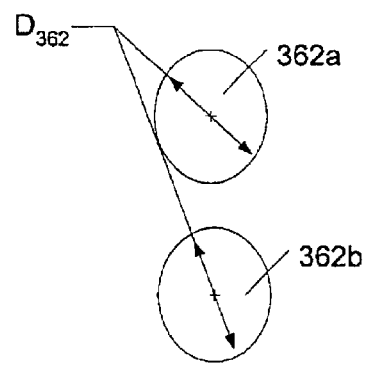
FIG. 3R is a top view of an alternate embodiment of the resilient coupling of the apparatus of FIG. 3A.
Figure 3S:
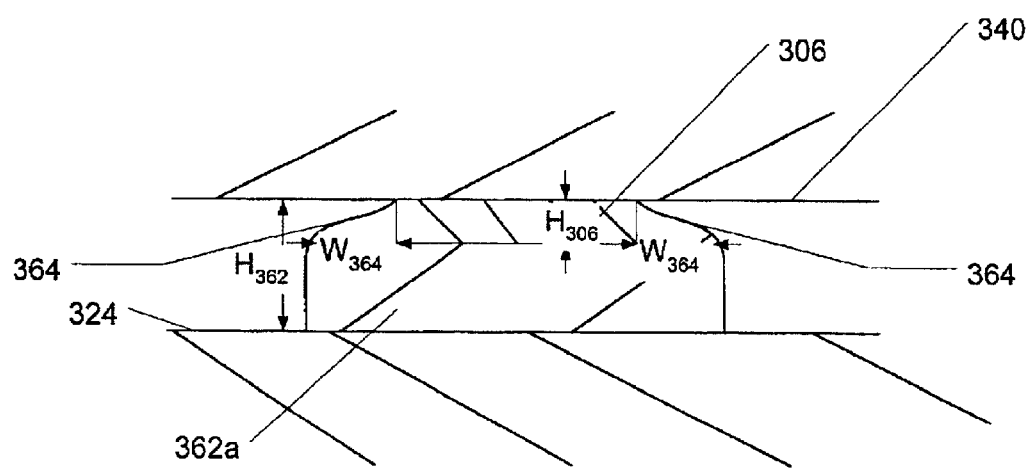
FIG. 3S is a detailed view of the alternate embodiment of the resilient coupling of FIG. 3S.
Figure 3T:
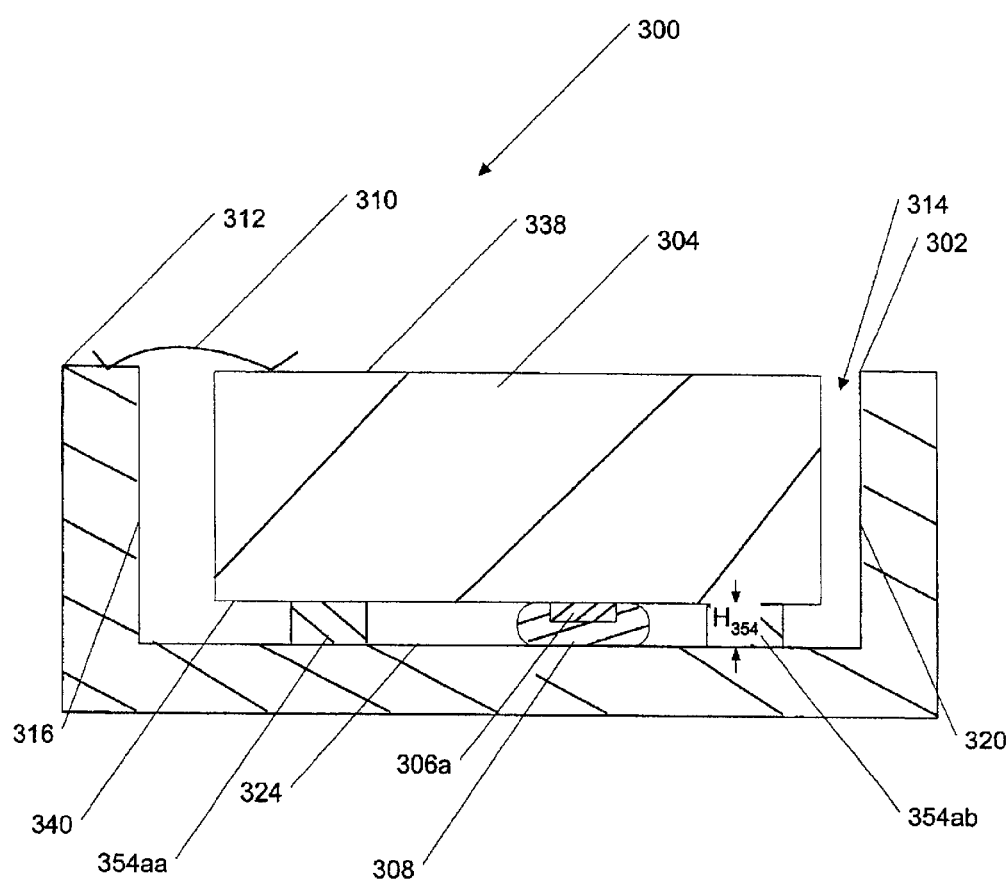
FIG. 3T is a cross-sectional view illustrating an alternate embodiment of an apparatus for resiliently attaching a mass to a package.
Figures 3U, 3V:
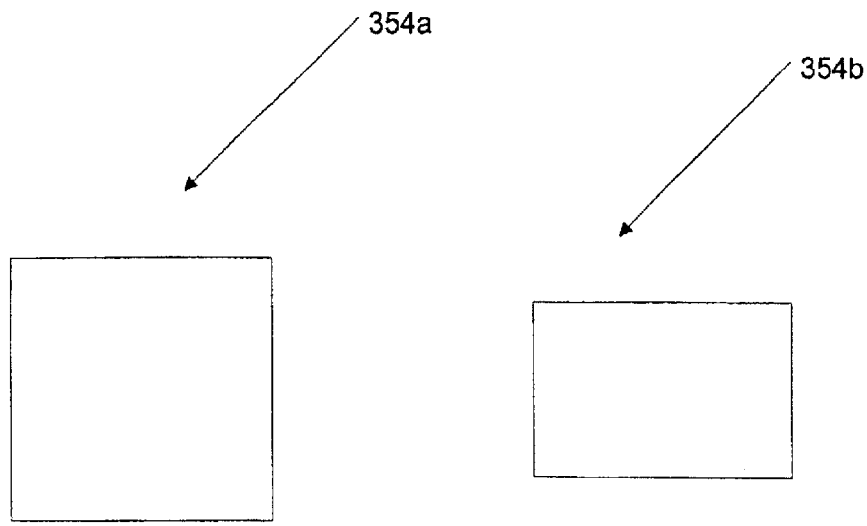
FIG. 3U is a top view of an embodiment of the sliding supports of the apparatus of FIG. 3T.
FIG. 3V is a top view of an alternate embodiment of the sliding supports of the apparatus of FIG. 3T.
Figures 3W, 3X:
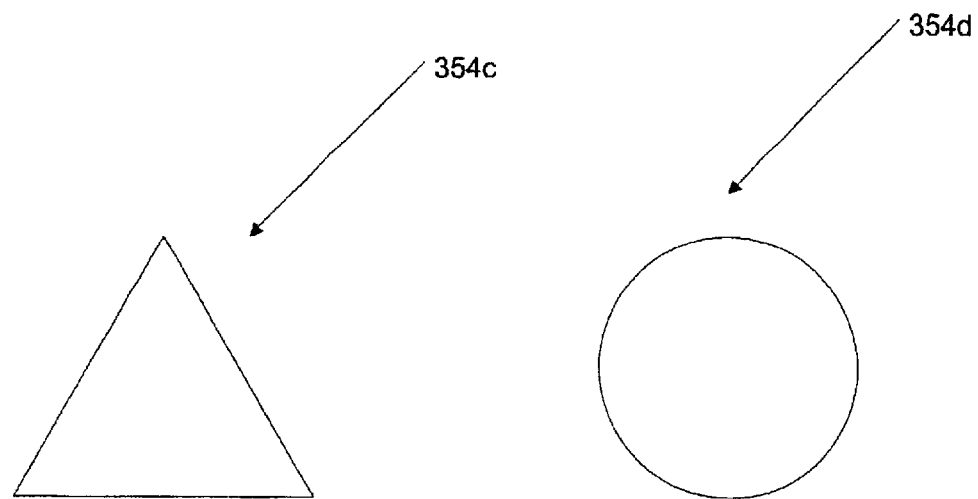
FIG. 3W is a top view of an alternate embodiment of the sliding supports of the apparatus of FIG. 3T.
FIG. 3X is a top view of an alternate embodiment of the sliding supports of the apparatus of FIG. 3T.

Referring to FIGS. 3R and 3S, in an alternate embodiment, there is a first resilient coupling 362a and a second resilient coupling 362b. In a preferred embodiment, the resilient couplings 362a and 362b are solder preforms preferably having an approximately circular cross-sectional shape. The resilient couplings 362a and 362b are vertically proximate to each other and substantially equal in size. The resilient couplings 362a and 362b may be any number of conventional commercially available solder preforms of the type, for example, eutectic or non-eutectic. In a preferred embodiment, the resilient couplings 362a and 362b are a eutectic type in order to optimally provide good yield strength with a reasonable melt temperature. The total diameter $D_{362}$ of the resilient couplings 362a and 362b may range, for example, from about 50 to 100 mils. In a preferred embodiment, the overall diameter $D_{362}$ of the resilient couplings 362a and 362b ranges from about 70 to 80 mils in order to optimally minimize thermal stresses. The height $H_{362}$ of the resilient couplings 362a and 362b may range, for example, from about 2 to 4 mils. In a preferred embodiment, the height $H_{362}$ of the resilient couplings 362a and 362b ranges from about 2.5 to 3 mils in order to optimally minimize thermal stresses. In a preferred embodiment, the resilient couplings 362a and 362b are coupled to the bottom surface 324 of the cavity 314 the package 302 using conventional solder equipment and processes. In a preferred embodiment, the resilient couplings 362a and 362b are coupled to the bond pads 306 using conventional solder equipment and processes.

The first resilient coupling 362a may be located a perpendicular distance ranging, for example, from about 80 to 100 mils from the first wall 316 the cavity 314 of the package 302 and may be located a perpendicular distance ranging, for example, from about 40 to 50 from the second wall 318 of the cavity 314 of the package 302. In a preferred embodiment, the first resilient coupling 362a is located a perpendicular distance ranging from about 85 to 95 mils from the first wall 316 of the cavity 314 of the package 302 in order to optimally minimize thermal stresses and located a distance ranging from about 43 to 47 mils from the second wall 318 of the cavity 314 of the package 302 in order to optimally minimize thermal stresses.

The first resilient coupling 362a further includes one or more bumpers 364 for slidingly supporting the mass 304. In a preferred embodiment, there is a single bumper 364. In a preferred embodiment, the bumper 364 has an approximately annular cross-sectional shape. In a preferred embodiment, the bumper 364 is proximate to the bond pads 306. The width $W_{364}$ of the bumper 364 may range, for example, from about 2 to 6 mils. In a preferred embodiment, the width $W_{364}$ of the bumper 364 ranges from about 3 to 5 mils in order to optimally minimize thermal stresses.

The second resilient coupling 362b may be located a perpendicular distance ranging, for example, from about 80 to 100 mils from the first wall 316 the cavity 314 of the package 302 and may be located a perpendicular distance ranging, for example, from about 135 to 165 mils from the second wall 318 of the cavity 314 of the package 302. In a preferred embodiment, the second resilient coupling 362b is located a perpendicular distance ranging from about 85 to 95 mils from the first wall 316 of the cavity 314 of the package 302 in order to optimally minimize thermal stresses and located a distance ranging from about 147 to 157 mils from the second wall 318 of the cavity 314 of the package 302 in order to optimally minimize thermal stresses.

The second resilient coupling 362b further includes one or more bumpers 366 for slidingly supporting the mass 304. In a preferred embodiment, there is a single bumper 366. In a preferred embodiment, the bumper 366 has an approximately annular cross-sectional shape. In a preferred embodiment, the bumper 366 is proximate to the bond pads 306. The width $W_{350}$ of the bumper 366 may range, for example, from about 2 to 6 mils. In a preferred embodiment, the width $W_{366}$ of the bumper 366 ranges from about 3 to 5 mils in order to optimally minimize thermal stresses.

Referring to FIGS. 3T through 3X, in an alternate embodiment, the system 300 further includes one or more sliding supports 354a, 354b, 354c, or 354d. The sliding supports 354a, 354b, 354c, or 354d preferably slidingly support the mass 304. The number of sliding supports 354a, 354b, 354c, or 354d preferably depends upon having a sufficient amount of sliding supports in order to optimally slidingly support the mass 304. The sliding supports 354a, 354b, 354c, or 354d are preferably coupled to the bottom surface 324 of the cavity 314 of the package 302. The sliding supports 354a may have an approximately square cross sectional shape. The sliding supports 354b may have an approximately rectangular cross sectional shape. The sliding supports 354c may have an approximately triangular cross sectional shape. The sliding supports 354d may have an approximately circular cross sectional shape. The sliding supports 354a, 354b, 354c, or 354d may be, for example, tungsten or ceramic. In a preferred embodiment, the sliding supports 354a, 354b, 354c, or 354d are tungsten in order to optimally provides standard packaging process. In a preferred embodiment, the sliding supports 354 are coupled to the bottom surface 324 of the cavity 314 of the package 302 using conventional means of integrating the sliding supports 310 into the package 302.

The sliding supports 354a, 354b, 354c, or 354d may have an approximate cross-sectional area ranging from about 400 to 1600 square mils, individually. In a preferred embodiment, the sliding supports 354a, 354b, 354c, or 354d have an approximate cross-sectional area ranging from about 625 to 1225 square mils, individually, in order to optimally minimize thermal stresses. The height $H_{354}$ of the sliding supports 354a, 354b, 354c, or 354d may range, for example, from about 0.5 to 3 mils. In a preferred embodiment, the height $H_{354}$ of the sliding supports 354a, 354b, 354c, or 354d ranges from about 1 to 1.5 mils in order to optimally minimize thermal stresses.

In a preferred embodiment, there is a first sliding support 354aa, a second sliding support 354ab, a third sliding support 354ac, and a fourth sliding support 354ad. The first sliding support 354aa may be located a perpendicular distance ranging, for example, from about 45 to 75 mils from the first wall 316 of the cavity 314 of the package 302 and may be located a perpendicular distance ranging, for example, from about 85 to 115 mils from the second wall 318 of the cavity 314 of the package 302. In a preferred embodiment, the first sliding support 354aa is located a perpendicular distance ranging from about 52 to 62 mils from the first wall 316 of the cavity 314 of the package 302 in order to optimally minimize thermal stresses and located a perpendicular distance from about 90 to 105 mils from the second wall 318 of the cavity 314 of the package 302 in order to optimally minimize thermal stresses.

The second sliding support 354ab may be located a perpendicular distance ranging, for example, from about 45 to 75 mils from the first wall 316 of the cavity 314 of the package 302 and may be located a perpendicular distance ranging, for example, from about 15 to 30 mils from the second wall 318 of the cavity 314 of the package 362. In a preferred embodiment, the second sliding support 354*ab* is located a perpendicular distance ranging from about 52 to 62 mils from the first wall 316 of the cavity 314 of the package 302 in order to optimally minimize thermal stresses and located a perpendicular distance ranging from about 20 to 25 mils from the second wall 318 of the cavity 314 of the package 302 in order to optimally minimize thermal stresses.

The third sliding support 354*ac* may be located a perpendicular distance ranging, for example, from about 85 to 115 mils from the first wall 316 of the cavity 314 of the package 302 and may be located a perpendicular distance ranging, for example, from about 15 to 30 mils from the second wall 318 of the cavity 314 of the package 302. In a preferred embodiment, the third sliding support 354*ac* is located a perpendicular distance ranging from about 90 to 105 mils from the first wall 316 of the cavity 314 of the package 302 in order to optimally minimize thermal stresses and located a perpendicular distance ranging from about 20 to 25 mils from the second wall 318 of the cavity 314 of the package 302 in order to optimally minimize thermal stresses.

The fourth sliding support 354*ad* may be located a perpendicular distance ranging, for example, from about 85 to 115 mils from the first wall 316 of the cavity 314 of the package 302 and may be located a perpendicular distance ranging, for example, from about 85 to 115 mils from the second wall 318 of the cavity 314 of the package 302. In a preferred embodiment, the fourth sliding support 354*ad* is located a perpendicular distance ranging from about 90 to 105 mils from the first wall 316 of the cavity 314 of the package 302 in order to optimally minimize thermal stresses and located a perpendicular distance ranging from about 90 to 105 mils from the second wall 318 of the cavity 314 of the package 302 in order to optimally minimize thermal stresses.

In an alternate embodiment, the resilient couplings 308 may also electrically couple the mass 304 to the package 302.

In an alternate embodiment, the resilient couplings 362*a* and 362*b* may also electrically couple the mass 304 to the package 302.

Referring to FIGS. 4A through 4E, an embodiment of a system 400 for resiliently coupling a mass to a package preferably includes a package 402, a mass 404, one or more bond pads 406, one or more resilient couplings 408, and one or more electrical connections 410.

The package 402 is coupled to the resilient couplings 408 and the electrical connections 410. The package 402 may be, for example, a housing or a substrate. In a preferred embodiment, the package 402 is a housing in order to optimally provide a surface mount component. The package 402 preferably includes a first parallel planar surface 412, a second parallel planar surface 414, and a cavity 416. The cavity 416 preferably includes a first wall 418, a second wall 420, a third wall 422 and a fourth wall 424. The first wall 418 and the third wall 422 are preferably approximately parallel to each other and the second wall 420 and the fourth wall 424 are preferably approximately parallel to each other. The second wall 422 and the fourth wall 424 are also preferably perpendicular to the first wall 418 and the third wall 422. The cavity 416 preferably includes a bottom surface 426. The package 402 may be any number of conventional commercially available housings of the type, for example, ceramic, metal, or plastic. In a preferred embodiment, the package 402 is ceramic in order to optimally provide vacuum sealing of the mass 404 within the package 402.

The mass 404 is preferably resiliently attached to the package 402 by the resilient couplings 408 and electrically coupled to the housing by the electrical connections 410. The mass 404 preferably has an approximately rectangular cross-sectional shape. The mass 404 preferably includes all active regions.

In a preferred embodiment, the mass 404 includes a first member 440, a second member 442, and a third member 444. The first member 440 is preferably on top of the second member 442 and the second member 442 is preferably on top of the third member 444. In a preferred embodiment, the first member 440, the second member 442, and the third member 444 are a micro machined sensor substantially as disclosed in copending U.S. patent application Ser. No. 09/936,640, filed on Sep. 12, 2001, the disclosure of which is incorporated herein by reference. The first member 440 preferably includes one or more parallel planar surfaces. In a preferred embodiment, the first member 440 includes a top parallel planar surface 446. The second member 442 preferably includes one or more parallel planar surfaces. In a preferred embodiment, the second member 442 includes a middle parallel planar surface 448. The third member 444 preferably includes one or more parallel planar surfaces. In a preferred embodiment, the third member 444 includes a bottom parallel planar surface 450. The bottom parallel planar surface 450 of the mass 404 preferably includes a first side 452, a second side 454, a third side 456, and a fourth side 458. The first side 452 and the third side 456 are preferably approximately parallel to each other and the second side 454 and the fourth side 458 are preferably approximately parallel to each other and preferably approximately perpendicular to the first side 452 and the third side 456.

In a preferred embodiment, the bottom parallel planar surface 450 of the mass 404 includes the bond pads 406. In a preferred embodiment, the bond pads 406 are substantially located in the center of the bottom parallel planar surface 450 of the mass 404. The bond pads 406 may be located a perpendicular distance ranging, for example, from about 80 to 100 mils from the first side 452 of the bottom parallel planar surface 450 of the mass 404 and may be located a perpendicular distance ranging, for example, from about 80 to 100 mils from the second side 454 of the bottom parallel planar surface 450 of the mass 404. In a preferred embodiment, the bond pads 406 are located a perpendicular distance a ranging from about 85 to 95 mils from the first side 452 of the bottom parallel planar surface 450 of the mass 404 in order to optimally minimize thermal stresses and located a perpendicular distance ranging from about 85 to 95 mils from the second side 454 of the bottom parallel planar surface 450 of the mass 404 in order to optimally minimize thermal stresses. The bond pads 406 may be used for, for example, solder, glass frit, conductive epoxy, or non-conductive epoxy bonding. In a preferred embodiment, the bond pads 406 are used for solder bonding in order to optimally provide good manufacturability. In a preferred embodiment, the bond pads 406 contact area is maximized in order to optimize the shock tolerance of the mass 404. In a preferred embodiment, the bond pads 406 have minimal discontinuities in order to optimize the distribution of thermal stresses in the mass 404. In several alternate embodiments, there is a plurality of bond pads 406 in order to optimize the relief of thermal stresses in the mass 404. In a preferred embodiment, there is a single bond pad 406a. The bond pad 406a preferably has an approximately circular cross-sectional shape. The diameter $D_{406a}$ may range, for example, from about 50 to 100 mils. In a preferred embodiment, the diameter $D_{406a}$ of the bond pad 406a ranges from about 70 to 80 mils in order to optimally minimize thermal stresses. The height $H_{406}$ of the bond pad 406a may range, for example, from about 0.1 to 1 micron. In a preferred embodiment, the height $H_{411}$, of the bond pad 406a ranges from about 0.24 to 0.72 microns in order to optimally minimize thermal stresses.

The resilient couplings 408 preferably resiliently attaches the bond pads 406 to the package 402. The resilient couplings 408 are preferably coupled to the bottom surface 426 of the cavity 416. In a preferred embodiment, the resilient couplings 408 are solder preforms. In a preferred embodiment, the resilient couplings 408 have an approximate cross-sectional circular shape. In a preferred embodiment, the resilient couplings 408 have minimal discontinuities in order to optimize the distribution of thermal stresses. In several alternate embodiments, there is a plurality of resilient couplings 408 in order to optimize the relief of thermal stresses in the mass 404. The resilient couplings 408 may be any number of conventional commercially available solder preforms of the type, for example, eutectic or non-eutectic. In a preferred embodiment, the resilient couplings 408 are a eutectic type in order to optimally provide good yield strength with a reasonable melt temperature. The resilient couplings 408 may be located a perpendicular distance ranging, for example, from about 80 to 100 mils from the first wall 418 of the cavity 416 of the package 402 and may be located a perpendicular distance ranging, for example, from about 80 to 100 mils from the second wall 420 of the cavity 416 of the package 402. In a preferred embodiment, the resilient couplings 408 are located a perpendicular distance ranging from about 85 to 95 mils from the first wall 418 of the cavity 416 of the package 402 in order to optimally minimize thermal stresses and located a distance ranging from about 85 to 95 mils from the second wall 420 of the cavity 416 of the package 402 in order to optimally minimize thermal stresses. In a preferred embodiment, there is a single resilient coupling 408. The diameter $D_{408}$ of the resilient coupling 408 may range, for example, from about 50 to 100 mils. In a preferred embodiment, the diameter $D_{408}$ of the resilient coupling 408 ranges from about 70 to 80 mils in order to optimally minimize thermal stresses. The height $H_{408}$ of the resilient coupling 408 may range, for example, from about 2 to 4 mils. In a preferred embodiment, the height $H_{408}$ of the resilient coupling 408 ranges from about 2.5 to 3 mils in order to optimally minimize thermal stresses.

In a preferred embodiment, the resilient coupling 408 further includes one or more bumpers 460 for slidingly supporting the mass 404. In a preferred embodiment, there is a single bumper 460. In a preferred embodiment the bumper 460 has an approximately annular cross-sectional shape. In a preferred embodiment, the bumper 460 surrounds the bond pads 406. In a preferred embodiment, the bumper 460 is proximate to the bond pads 406. The width $W_{460}$ of the bumper 460 may range, for example, from about 2 to 6 mils. In a preferred embodiment, the width $W_{460}$ of the bumper 460 ranges from about 3 to 5 mils in order to optimally minimize thermal stresses. In a preferred embodiment, the resilient couplings 408 are coupled to the bond pad 406 using conventional solder equipment and processes. In a preferred embodiment, the resilient couplings 408 are coupled to the bottom surface 426 of the cavity 416 of the package 402 using conventional solder equipment and processes.

The electrical connections 410 preferably electrically couple the mass 404 to the package 402. In a preferred embodiment, the electrical connections 410 are wire bonds. The electrical connections 410 may be any number of conventional commercially available wire bonds of the type, for example, gold or aluminum. In a preferred embodiment, the electrical connections 410 are gold in order to optimally provide compatibility with the package and the mass 404 metallization. In a preferred embodiment, there is a first electrical connection 410a and a second electrical connection 410b. The first electrical connection 410a preferably electrically couples the first parallel planar surface 412 of the package 402 to the top parallel planar surface 446 of the mass 404. The second electrical connection 410b preferably electrically couples the second parallel planar surface 414 of the package 402 to the middle parallel planar surface 448 of the mass 404. In a preferred embodiment, the electrical connections 410 are coupled to the package 402 using conventional wire-bonding equipment and processes. In a preferred embodiment, the electrical connections 410 are coupled to the mass 404 using conventional wire-bonding equipment and processes.

Figure 4A:
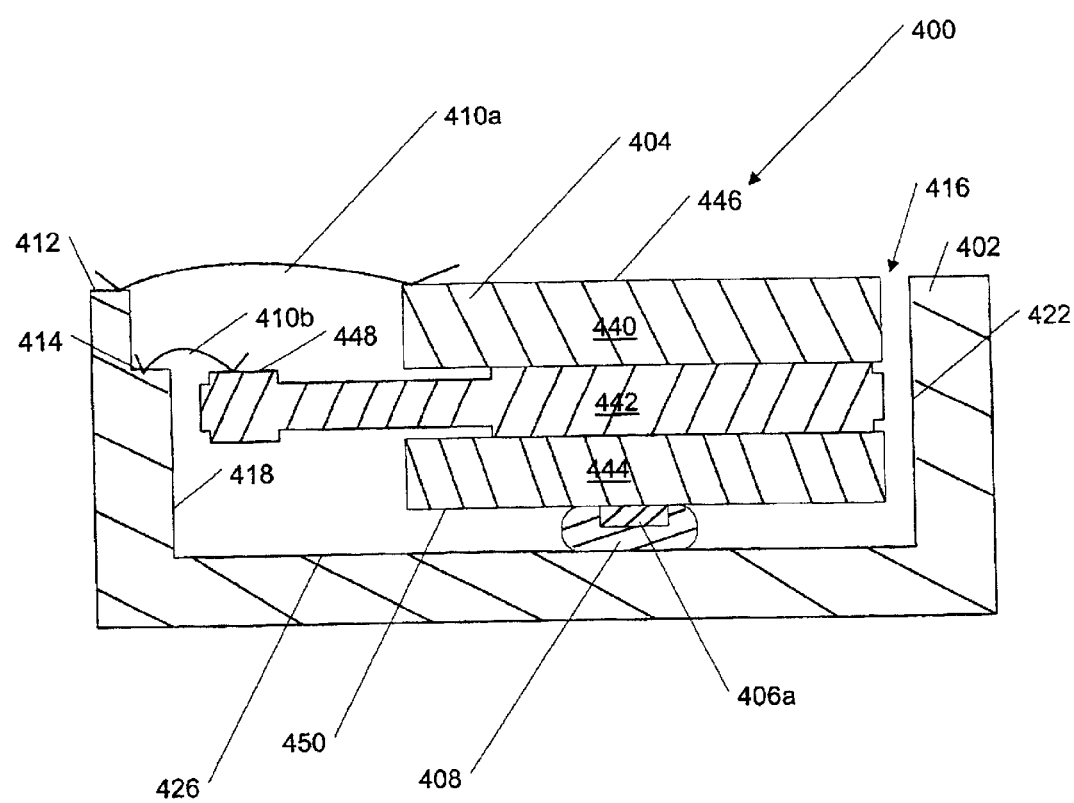
FIG. 4A is a cross-sectional view illustrating an embodiment of an apparatus for resiliently attaching a mass to a package.
Figure 4B:
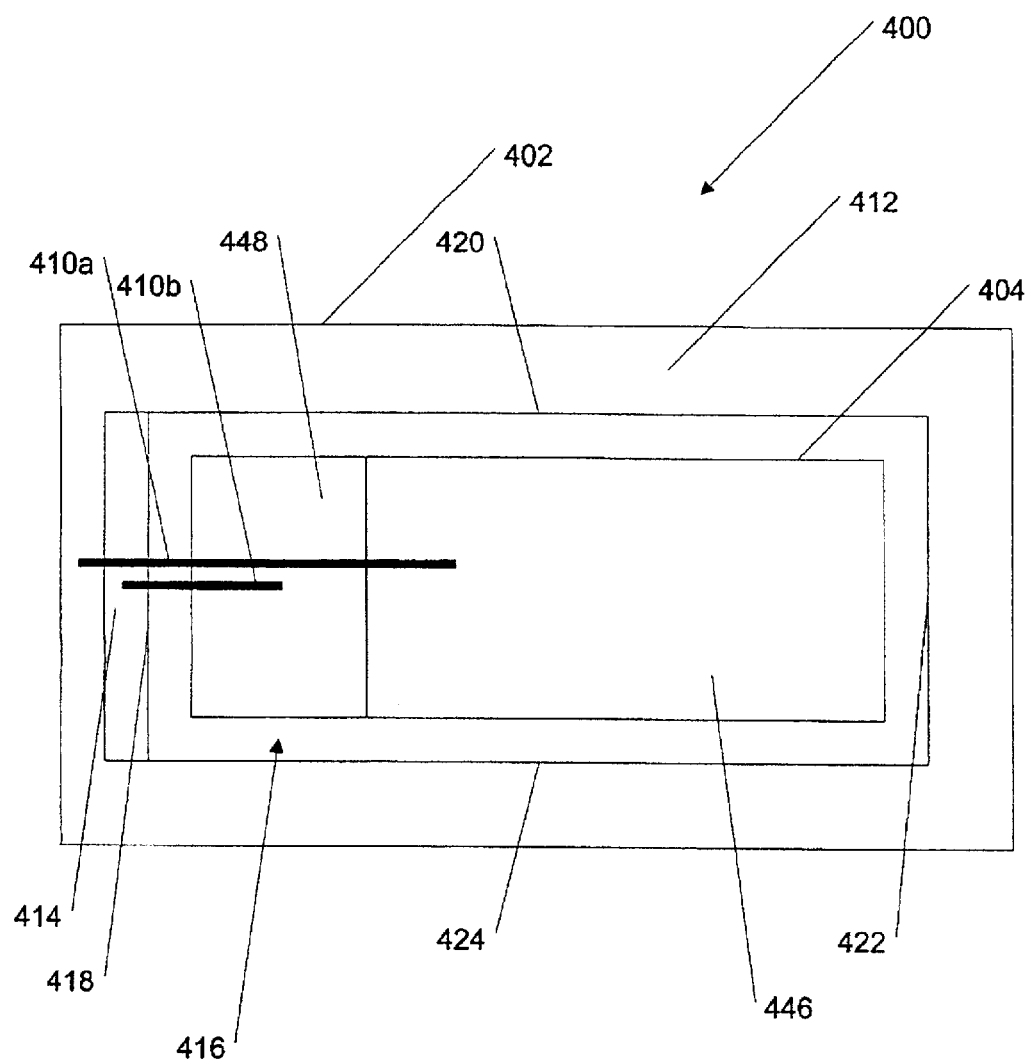
FIG. 4B is a top view of an embodiment of the apparatus of FIG. 4A.
Figure 4C:
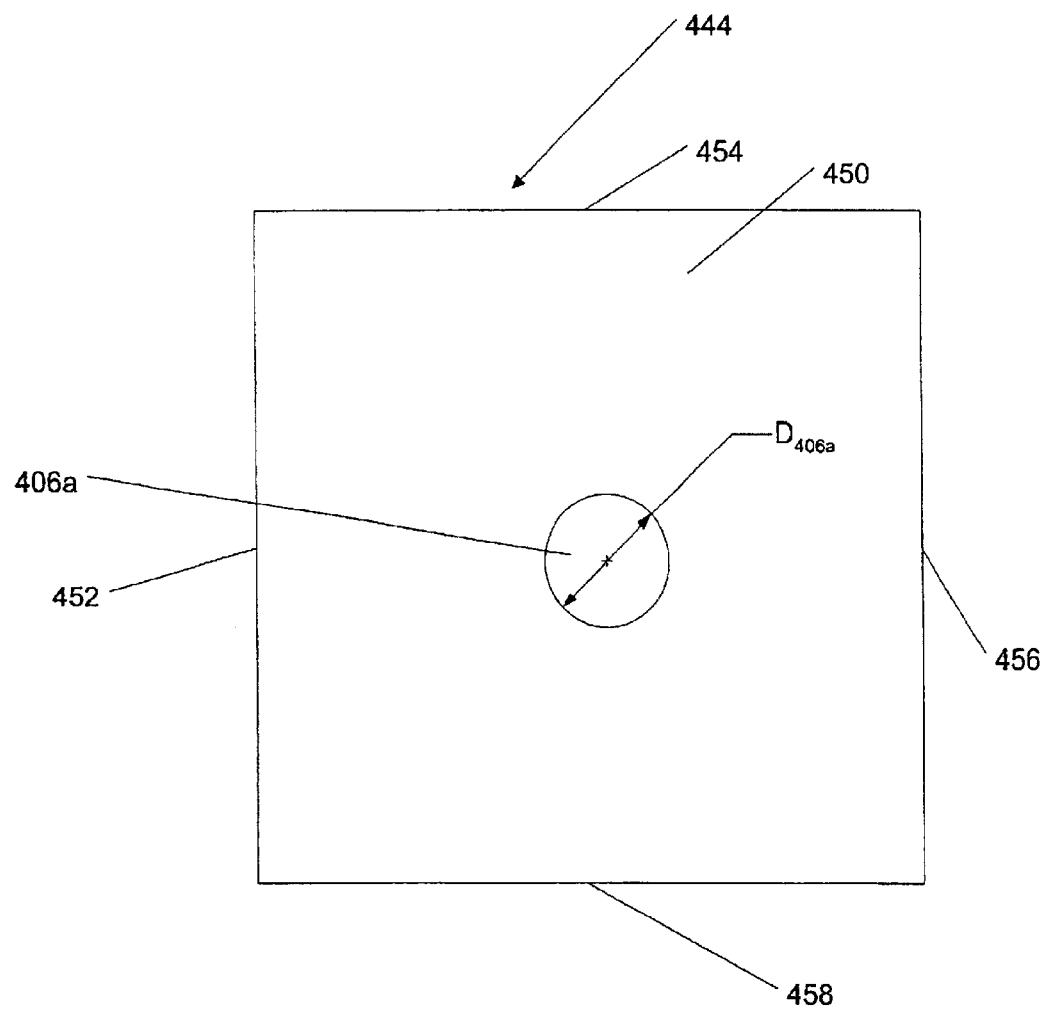
FIG. 4C is a bottom view of an embodiment of the mass of the apparatus of FIG. 4A.
Figure 4D:
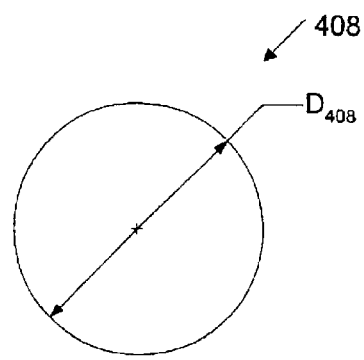
FIG. 4D is a top view of an embodiment of the resilient coupling of the apparatus of FIG. 4A.
Figure 4E:
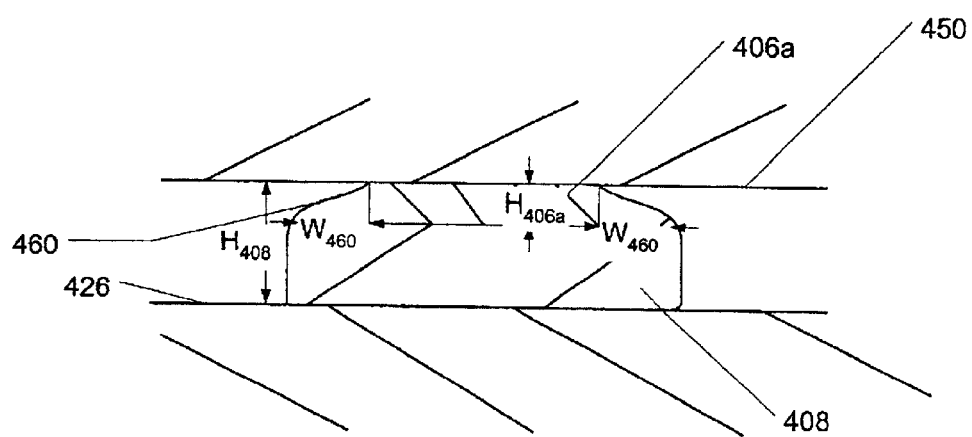
FIG. 4E is a detailed view of the embodiment of the resilient coupling of FIG. 4D.
Figure 4F:
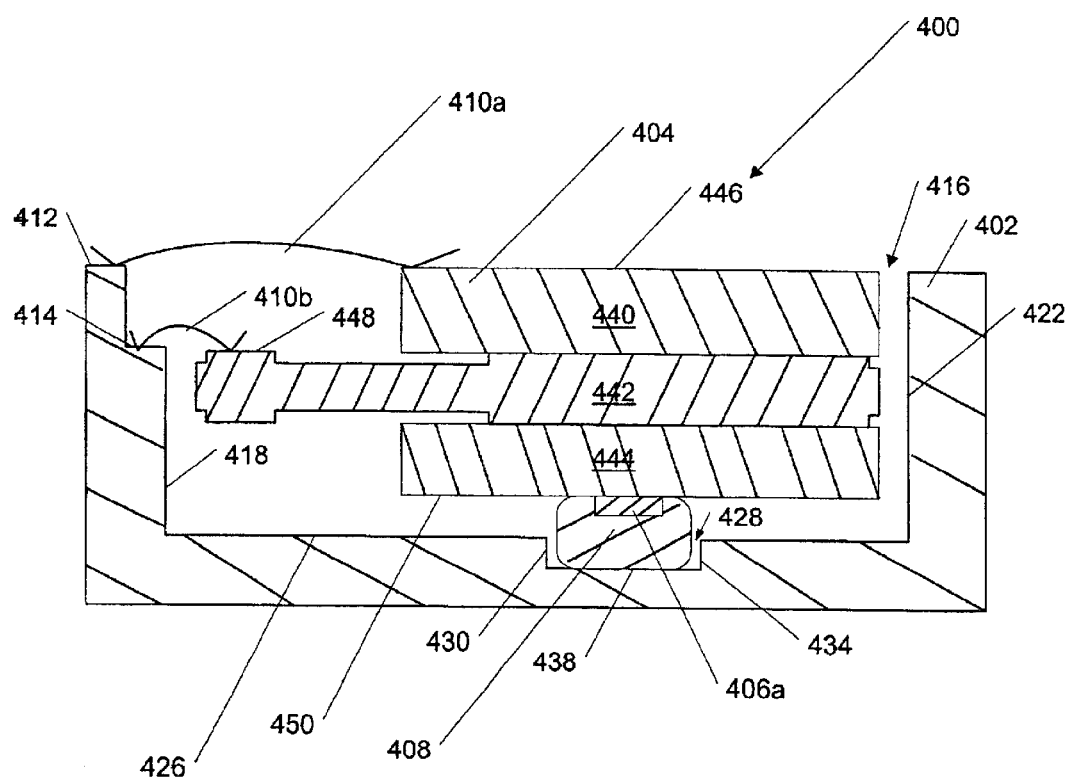
FIG. 4F is a cross-sectional view illustrating an alternate embodiment of an apparatus for resiliently attaching a mass to a package.

Referring to FIG. 4F, in an alternate embodiment, the bottom surface 426 of the package 402 preferably further includes a recess 428. The recess 428 may be circular or rectangular in shape. The recess 428 preferably includes a first wall 430, a second wall 432, a third wall 434 and a fourth wall 436. The first wall 430 and the third wall 434 are preferably approximately parallel to each other and the second wall 432 and the fourth wall 436 are preferably approximately parallel to each other. The second wall 432 and the fourth wall 436 are also preferably perpendicular to the first wall 430 and the third wall 434. The recess 428 preferably includes a bottom surface 438. The length $L_{428}$ of the recess 428 may range, for example, from about 110 to 130 mils. In a preferred embodiment the length $L_{428}$ of the recess 428 ranges from about 115 to 125 mils in order to optimally minimize thermal stresses. The width $W_{428}$ of the recess 428 may range, for example, from about 110 to 130 mils. In a preferred embodiment the width $W_{428}$ of the recess 428 ranges from about 115 to 125 mils in order to optimally minimize thermal stresses. The height $H_{428}$ of the recess 428 may range, for example, from about 1 to 2 mils. In a preferred embodiment the height $H_{428}$ of the recess 428 ranges from about 1.25 to 1.75 mils in order to optimally minimize thermal stresses. In a preferred embodiment, the recess 428 is substantially located in the center of the bottom surface 426 of the package 402. The first wall 430 of the recess 428 may be located a perpendicular distance ranging, for example, from 80 to 100 mils from the first wall 418 of the cavity 416. In a preferred embodiment, the first wall 430 of the recess 428 is located a perpendicular distance ranging from 85 to 95 mils from the first wall 418 of the cavity 416 in order to optimally minimize thermal stresses. The second wall 432 of the recess 428 may be located a perpendicular distance ranging, for example, from 80 to 100 mils from the second wall 420 of the cavity 416. In a preferred embodiment, the second wall 432 of the recess 428 is located a perpendicular distance ranging from 85 to 95 mils from the second wall 420 of the cavity 416 in order to optimally minimize thermal stresses.

In a preferred embodiment, the resilient coupling 408 is located in the recess 428. The resilient coupling 408 may be located a perpendicular distance ranging, for example, from about 2 to 7 mils from the first wall 430 of the recess 428 of the cavity 416 of the package 402 and may be located a perpendicular distance ranging, for example, from about 2 to 7 mils from the second wall 432 of the recess 428 of the cavity 416 of the package 402. In a preferred embodiment, the resilient coupling 408 is located a perpendicular distance ranging from about 3 to 5 mils from the first wall 430 of the recess 428 of the cavity 416 of the package 402 in order to optimally minimize thermal stresses and located a distance ranging from about 3 to 5 mils from the second wall 432 of the recess 428 of the cavity 416 of the package 402 in order to optimally minimize thermal stresses. In a preferred embodiment, the resilient coupling 408 is coupled to the bottom surface 438 of the recess 428 using conventional solder equipment and processes.

Figure 4G:
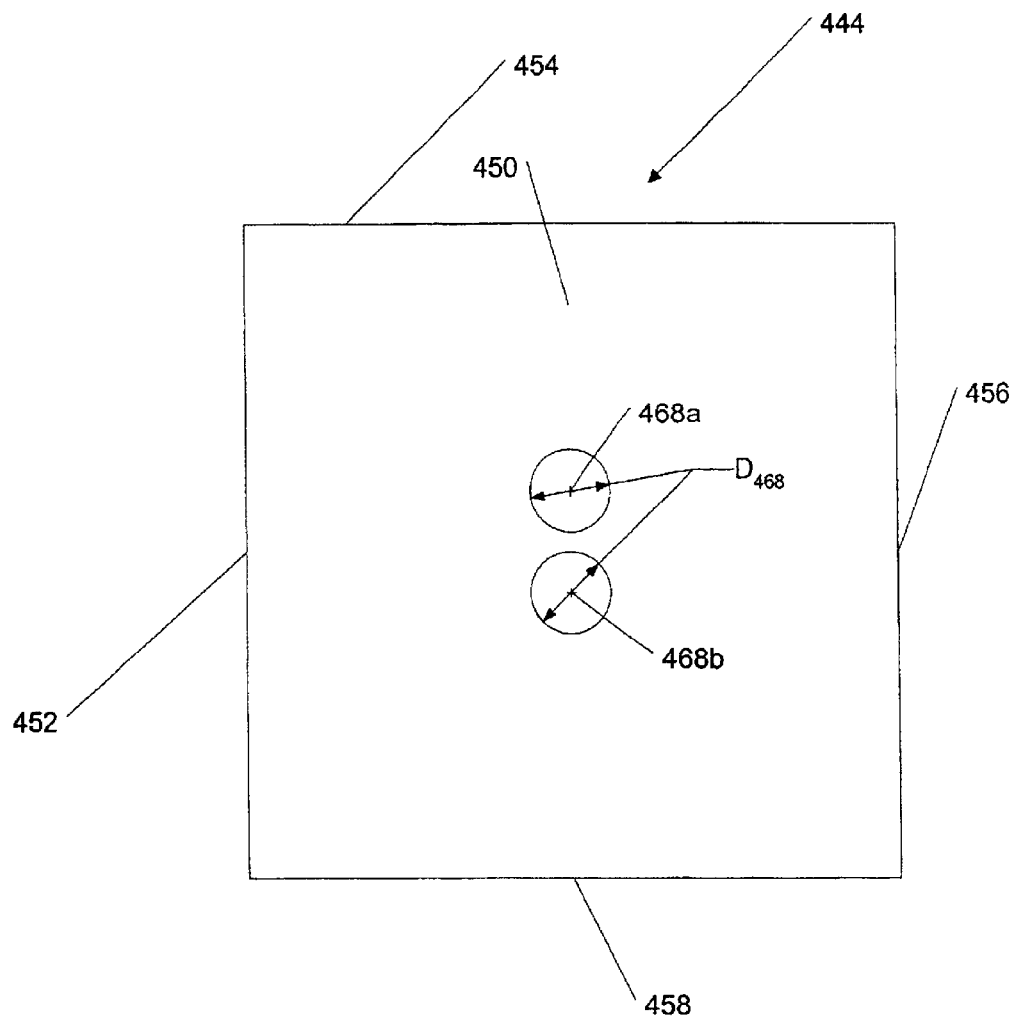
FIG. 4G is a bottom view of an alternate embodiment of the mass of the apparatus of FIG. 4A.

Referring to FIG. 4G, in an alternate embodiment, there is a first bond pad 468a and a second bond pad 468b that are substantially equal in size and vertically proximate to each other. The bond pads 468a and 468b may be used for, for example, solder, glass frit, conductive epoxy, or non-conductive epoxy bonding. In a preferred embodiment, the bond pads 468 are used for solder bonding in order to optimally provide good manufacturability. The bond pads 468 preferably have an approximately circular cross-sectional shape. The total diameter $D_{468}$ of the bond pads 468a and 468b may range, for example, from about 50 to 100 mils. In a preferred embodiment, the total diameter $D_{468}$ of the bond pads 468a and 468b range from about 70 to 80 mils in order to optimally minimize thermal stresses. The height $H_{468}$ of the bond pads 468a and 468b may range, for example, from about 0.1 to 1 micron. In a preferred embodiment, the height $H_{468}$ of the bond pads 468a and 468b range from about 0.24 to 0.72 microns in order to optimally minimize thermal stresses.

The first bond pad 468a is preferably substantially located in the center of the bottom parallel planar surface 450 of the mass 404. The first bond pad 468a may be located a perpendicular distance ranging, for example, from about 80 to 100 mils from the first side 452 of the bottom parallel planar surface 450 of the mass 404 and may be located a perpendicular distance ranging, for example, from about 40 to 50 mils from the second side 454 of the bottom parallel planar surface 450 of the mass 404. The first bond pad 468a is preferably located a perpendicular distance ranging from about 85 to 95 mils from the first side 452 of the bottom parallel planar surface 450 of the mass 404 in order to optimally minimize thermal stresses and located a perpendicular distance ranging from about 43 to 47 mils from the second side 454 of the bottom parallel planar surface 450 of the mass 404 in order to optimally minimize thermal stresses.

The second bond pad 468b is preferably located substantially in the center of the bottom parallel planar surface 450 of the mass 404. The second bond pad 468b may be located a perpendicular distance ranging, for example, from about 80 to 100 mils from the first side 452 of the bottom parallel planar surface 450 of the mass 404 and may be located a perpendicular distance ranging, for example, from about 135 to 165 mils from the second side 454 of the bottom parallel planar surface 450 of the mass 404. The second bond pad 468b is preferably located a perpendicular distance ranging from about 85 to 95 mils from the first side 452 of the bottom parallel planar surface 450 of the mass 404 in order to optimally minimize thermal stresses and located a perpendicular distance ranging from about 147 to 157 mils from the second side 454 of the bottom parallel planar surface 450 of the mass 404 in order to optimally minimize thermal stresses.

Figure 4H:
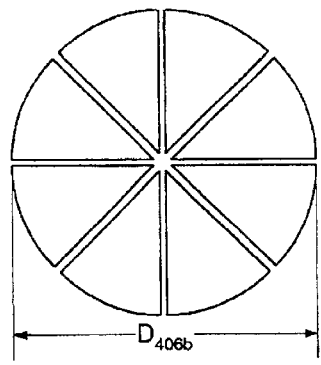
FIG. 4H is a top view of an alternate embodiment of the bond pad of the apparatus of FIG. 4A.

Referring to FIG. 4H, in an alternate embodiment, there is a bond pad 406b. The bond pad 406b may have an approximately oct-pie-wedge cross-sectional shape. The diameter $D_{4406b}$ of the bond pad 406b may range, for example, from about 50 to 100 mils. In a preferred embodiment, the diameter $D_{406b}$ of the bond pad 406b ranges from about 70 to 80 mils in order to optimally minimize thermal stresses. The height $H_4$, of the bond pad 406b may range, for example, from about 0.1 to 1 micron. In a preferred embodiment, the height $H_{406}$ of the bond pad 406b ranges from about 0.24 to 0.72 microns in order to optimally minimize thermal stresses.

Figure 4J:
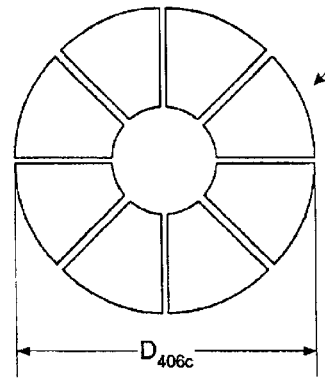
FIG. 4J is a top view of an alternate embodiment of the bond pad of the apparatus of FIG. 4A.

Referring to FIG. 4J, in an alternate embodiment, there is bond pad 406c. The bond pad 406c may have an approximately hollow oct-pie-wedge cross-sectional shape. The diameter $D_{406c}$ of the bond pad 406c may range, for example, from about 50 to 100 mils. In a preferred embodiment, the diameter $D_{406c}$ of the bond pad 406c ranges from about 70 to 80 mils in order to optimally minimize thermal stresses. The height $H_{406}$ of the bond pad 406c may range, for example, from about 0.1 to 1 micron. In a preferred embodiment, the height $H_{406}$ of the bond pad 406c ranges from about 0.24 to 0.72 microns in order to optimally minimize thermal stresses.

Figure 4K:
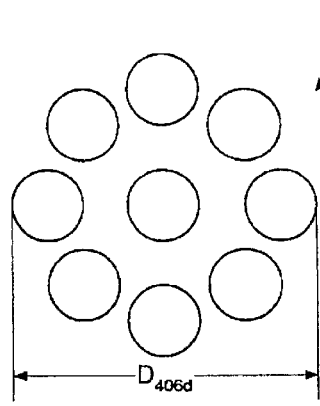
FIG. 4K is a top view of an alternate embodiment of the bond pad of the apparatus of FIG. 4A.

Referring to FIG. 4K, in an alternate embodiment, there is a bond pad 406d. The bond pad 406d has an approximately nine-circular cross-sectional shape. The overall diameter $D_{406d}$ of the bond pad 406d may range, for example, from about 50 to 100 mils. In a preferred embodiment, the overall diameter $D_{406d}$ of the bond pad 406d ranges from about 70 to 80 mils in order to optimally minimize thermal stresses. The height $H_{406}$, of the bond pad 406d may range, for example, from about 0.1 to 1 micron. In a preferred embodiment, the height $H_{406}$ of the bond pad 406d ranges from about 0.24 to 0.72 microns in order to optimally minimize thermal stresses.

Figure 4L:
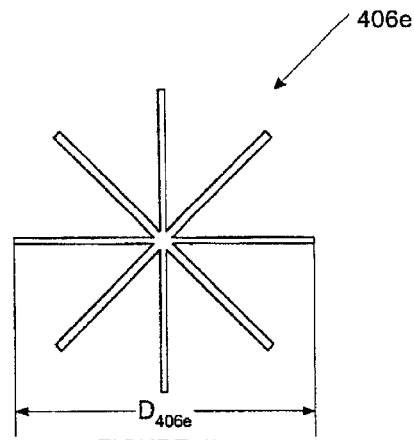
FIG. 4L is a top view of an alternate embodiment of the bond pad of the apparatus of FIG. 4A.

Referring to FIG. 4L, in an alternate embodiment, there is a single bond pad 406e. The bond pad 406e has an approximately starburst cross-sectional shape. The overall diameter $D_{406e}$ of the bond pad 406e may range, for example, from about 50 to 100 mils. In a preferred embodiment, the overall diameter $D_{406e}$, of the bond pad 406e ranges from about 70 to 80 mils in order to optimally minimize thermal stresses. The height $H_{406}$ of the bond pad 406e may range, for example, from about 0.1 to 1 micron. In a preferred embodiment, the height $H_{406}$ of the bond pad 406e ranges from about 0.24 to 0.72 microns in order to optimally minimize thermal stresses.

Figure 4M:
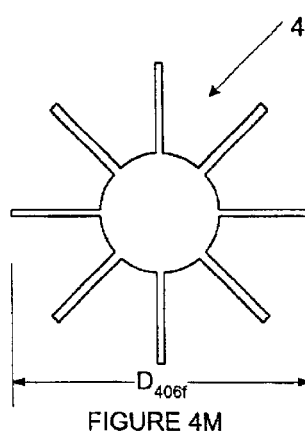
FIG. 4M is a top view of an alternate embodiment of the bond pad of the apparatus of FIG. 4A.

Referring to FIG. 4M, in an alternate embodiment, there is a single bond pad 406f. The bond pad 406f has an approximately sunburst cross-sectional shape. The overall diameter $D_{406f}$ of the bond pad 406f may range, for example, from about 50 to 100 mils. In a preferred embodiment, the overall diameter $D_{406f}$ of the bond pad 406f ranges from about 70 to 80 mils in order to optimally minimize thermal stresses. The height $H_{406}$ of the bond pad 406f may range, for example, from about 0.1 to 1 micron. In a preferred embodiment, the height $H_{406e}$ of the bond pad 406f ranges from about 0.24 to 0.72 microns in order to optimally minimize thermal stresses.

Figure 4R:
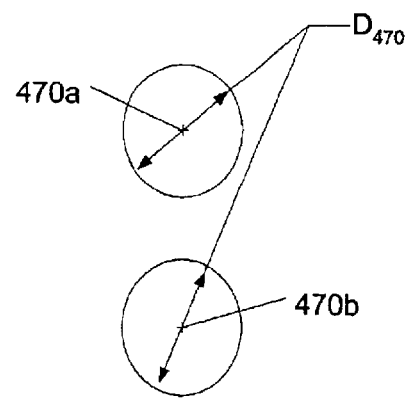
FIG. 4R is a top view of an alternate embodiment of the resilient coupling of the apparatus of FIG. 4A.
Figure 4S:
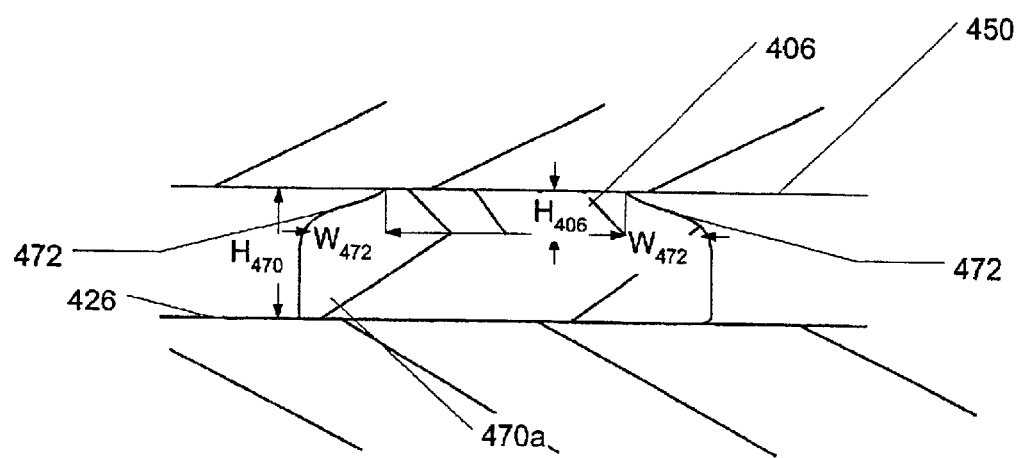
FIG. 4S is a detailed view of the alternate embodiment of the resilient coupling of FIG. 4R.
Figure 4T:
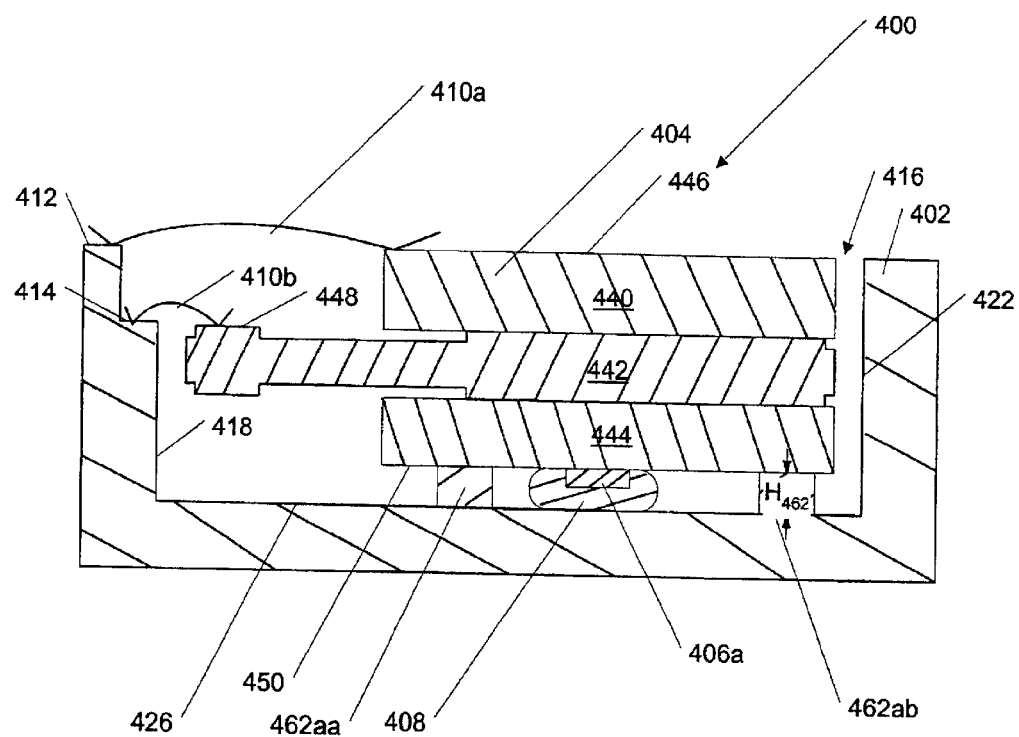
FIG. 4T is a cross-sectional view illustrating an alternate embodiment of an apparatus for resiliently attaching a mass to a package.
Figures 4U, 4V:
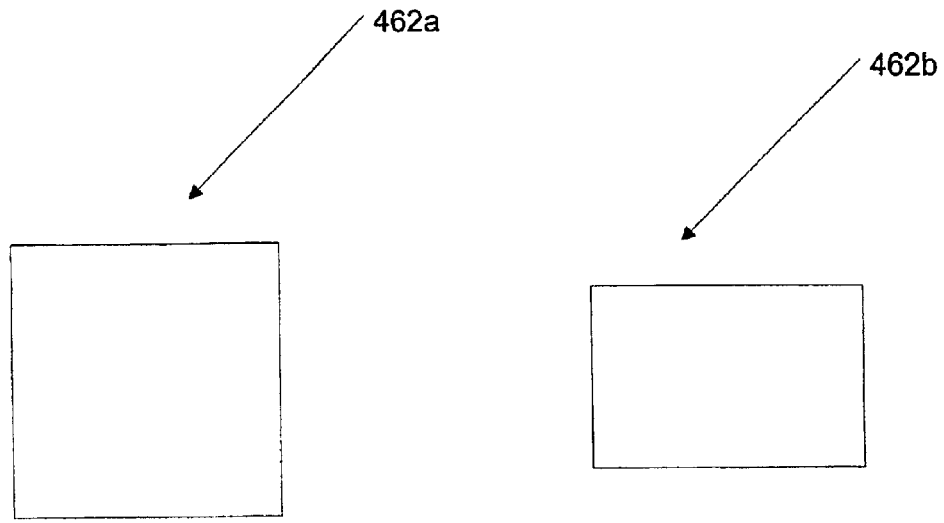
FIG. 4U is a top view of an embodiment of the sliding supports of the apparatus of FIG. 4T.
FIG. 4V is a top view of an alternate embodiment of the sliding supports of the apparatus of FIG. 4T.
Figures 4W, 4X:
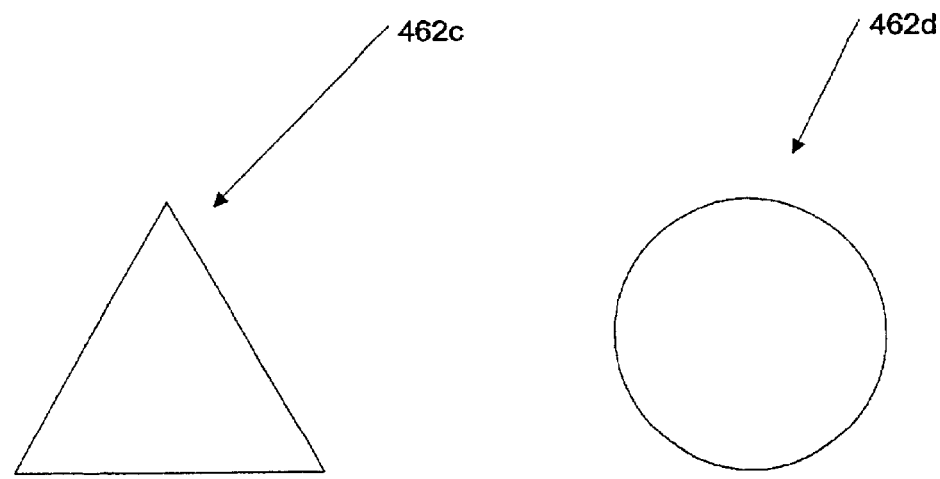
FIG. 4W is a top view of an alternate embodiment of the sliding supports of the apparatus of FIG. 4T.
FIG. 4X is a top view of an alternate embodiment of the sliding supports of the apparatus of FIG. 4T.

Referring to FIGS. 4R and 4S, in an alternate embodiment, there is a first resilient coupling 470a and a second resilient coupling 470b. In a preferred embodiment, the resilient couplings 470a and 470b are solder preforms preferably having an approximately circular cross-sectional shape. The resilient couplings 470a and 470b may be any number of conventional commercially available solder preforms of the type, for example, eutectic or non-eutectic. In a preferred embodiment, the resilient couplings 470a and 470b are a eutectic type in order to optimally provide good yield strength with a reasonable melt temperature. The total diameter $D_{470}$ of the resilient couplings 470a and 470b may range, for example, from about 50 to 100 mils. In a preferred embodiment, the total diameter $D_{470}$ of the resilient couplings 470a and 470b ranges from about 70 to 80 mils in order to optimally minimize thermal stresses. The height $H_{470}$ of the resilient couplings 470a and 470b may range, for example, from about 2 to 4 mils. In a preferred embodiment, the height $H_{470}$ of the resilient couplings 470a and 470b ranges from about 2.5 to 3 mils in order to optimally minimize thermal stresses. In a preferred embodiment, the resilient couplings 470a and 470b are coupled to the bottom surface 426 of the cavity 416 the package 402 using conventional solder equipment and processes. In a preferred embodiment, the resilient couplings 470a and 470b are coupled to the bond pad 406 using conventional solder equipment and processes.

The first resilient coupling 470a may be located a perpendicular distance ranging, for example, from about 80 to 100 mils from the first wall 418 the cavity 416 of the package 402 and may be located a perpendicular distance ranging, for example, from about 40 to 50 mils from the second wall 420 of the cavity 416 of the package 402. In a preferred embodiment, the first resilient coupling 470a is located a perpendicular distance ranging from about 85 to 95 mils from the first wall 418 of the cavity 416 of the package 402 in order to optimally minimize thermal stresses and located a distance ranging from about 43 to 47 mils from the second wall 420 of the cavity 416 of the package 402 in order to optimally minimize thermal stresses.

The first resilient coupling 470a further includes one or more bumpers 472 for slidingly supporting the mass 404. In a preferred embodiment, there is a single bumper 472. In a preferred embodiment the bumper 472 has an approximately annular cross-sectional shape. In a preferred embodiment, the bumper 472 is proximate to the bond pads 406. The width $W_{472}$ of the bumper 472 may range, for example, from about 2 to 6 mils. In a preferred embodiment, the width $W_{472}$ of the bumper 472 ranges from about 3 to 5 mils in order to optimally minimize thermal stresses.

The second resilient coupling 470b may be located a perpendicular distance ranging, for example, from about 80 to 100 mils from the first wall 418 the cavity 416 of the package 402 and may be located a perpendicular distance ranging, for example, from about 135 to 165 mils from the second wall 420 of the cavity 416 of the package 402. In a preferred embodiment, the second resilient coupling 470b is located a perpendicular distance ranging from about 85 to 95 mils from the first wall 418 of the cavity 416 of the package 402 in order to optimally minimize thermal stresses and located a distance ranging from about 147 to 157 mils from the second wall 420 of the cavity 416 of the package 402 in order to optimally minimize thermal stresses.

The second resilient coupling 470b further includes one or more bumpers 474 for slidingly supporting the mass 404. In a preferred embodiment, there is a single bumper 474. In a preferred embodiment the bumper 474 has an approximately annular cross-sectional shape. In a preferred embodiment, the bumper 474 is proximate to the bond pads 406. The width $W_{414}$ of the bumper 474 may range, for example, from about 2 to 6 mils. In a preferred embodiment, the width $W_{474}$ of the bumper 474 ranges from about 3 to 5 mils in order to optimally minimize thermal stresses.

Referring to FIGS. 4T through 4X, in an alternate embodiment, the system 400 further includes one or more sliding supports 462a, 462b, 462c, or 462d. The sliding supports 462a, 462b, 462c, or 462d preferably slidingly support the mass 404. The number of sliding supports 462a, 462b, 462c, or 462d preferably depends upon having a sufficient amount of sliding supports 462a, 462b, 462c, or 462d in order to optimally slidingly support the mass 404. The sliding supports 462a, 462b, 462c, or 462d are preferably coupled to the bottom surface 426 of the cavity 416 of the package 402. The sliding supports 462a may have an approximately square cross sectional shape. The sliding supports 462b may have an approximately rectangular cross sectional shape. The sliding supports 462c may have an approximately triangular cross-sectional shape. The sliding supports 462d may have an approximately circular cross-sectional shape. The sliding supports 462a, 462b, 462c, or 462d may be, for example, tungsten or ceramic. In a preferred embodiment, the sliding supports 462a, 462b, 462c, or 462d are tungsten in order to optimally provide a standard packaging process. The total cross-sectional area of the sliding supports 462a, 462b, 462c, or 462d may range, for example, from about 400 to 1600 square mils, individually. In a preferred embodiment, the total cross-sectional area of the sliding supports 462a, 462b, 462c, or 462d ranges from about 625 to 1225 square mils, individually, in order to optimally minimize thermal stresses. The height $H_{462}$ of the sliding supports 462a, 462b, 462c, or 462d may range, for example, from about 0.5 to 3 mils. In a preferred embodiment, the height $H_{462}$ of the sliding supports 462a, 462b, 462c, or 462d ranges from about 1 to 1.5 mils in order to optimally minimize thermal stresses.

In a preferred embodiment, there is a first sliding support 462aa, a second sliding support 462ab, a third sliding support 462ac, and a fourth sliding support 462ad. The first sliding support 462aa may be located a perpendicular distance ranging, for example, from about 45 to 75 mils from the first wall 418 of the cavity 416 of the package 402 and may be located a perpendicular distance ranging, for example, from about 85 to 115 mils from the second wall 420 of the cavity 416 of the package 402. In a preferred embodiment, the first sliding support 462aa is located a perpendicular distance ranging from about 52 to 62 mils from the first wall 418 of the cavity 416 of the package 402 in order to optimally minimize thermal stresses and located a perpendicular distance from about 90 to 105 mils from the second wall 420 of the cavity 416 of the package 402 in order to optimally minimize thermal stresses.

The second sliding support 462ab may be located a perpendicular distance ranging, for example, from about 45 to 75 mils from the first wall 418 of the cavity 416 of the package 402 and may be located a perpendicular distance ranging, for example, from about 15 to 30 mils from the second wall 420 of the cavity 416 of the package 402. In a preferred embodiment, the second sliding support 462ab is located a perpendicular distance ranging from about 52 to 62 mils from the first wall 418 of the cavity 416 of the package 402 in order to optimally minimize thermal stresses and located a perpendicular distance ranging from about 20 to 25 mils from the second wall 420 of the cavity 416 of the package 402 in order to optimally minimize thermal stresses.

The third sliding support 462ac may be located a perpendicular distance ranging, for example, from about 85 to 115 mils from the first wall 418 of the cavity 416 of the package 402 and may be located a perpendicular distance ranging, for example, from about 15 to 30 mils from the second wall 420 of the cavity 416 of the package 402. In a preferred embodiment, the third sliding support 462*ac* is located a perpendicular distance ranging from about 90 to 105 mils from the first wall 418 of the cavity 416 of the package 402 in order to optimally minimize thermal stresses and located a perpendicular distance ranging from about 20 to 25 mils from the second wall 420 of the cavity 416 of the package 402 in order to optimally minimize thermal stresses.

The fourth sliding support 462*ad* may be located a perpendicular distance ranging, for example, from about 85 to 115 mils from the first wall 418 of the cavity 416 of the package 402 and may be located a perpendicular distance ranging, for example, from about 85 to 115 mils from the second wall 420 of the cavity 416 of the package 402. In a preferred embodiment, the fourth sliding support 462*ad* is located a perpendicular distance ranging from about 90 to 105 mils from the first wall 418 of the cavity 416 of the package 402 in order to optimally minimize thermal stresses and located a perpendicular distance ranging from about 90 to 105 mils from the second wall 420 of the cavity 416 of the package 402 in order to optimally minimize thermal stresses.

In an alternate embodiment, the resilient couplings 408 may also electrically couple the mass 404 to the package 402.

In an alternate embodiment, the resilient couplings 470*a* and 470*b* may also electrically couple the mass 404 to the package 402.

Referring to FIGS. 5A through 5G, an alternate embodiment of a system 500 for resiliently coupling a mass to a package preferably includes a package 502, a mass 504, one or more bond pads 506, one or more resilient couplings 508, and one or more electrical connections 510.

The package 502 is coupled to the resilient couplings 508 and the electrical connections 510. The package 502 may be, for example, a housing or a substrate. In a preferred embodiment, the package 502 is a housing in order to optimally provide a surface mount component. The package 502 preferably includes a top parallel planar surface 512 and a cavity 514. The cavity 514 preferably includes a first wall 516, a second wall 518, a third wall 520 and a fourth wall 522. The first wall 516 and the third wall 520 are preferably approximately parallel to each other and the second wall 518 and the fourth wall 522 are preferably approximately parallel to each other. The second wall 518 and the fourth wall 522 are also preferably perpendicular to the first wall 516 and the third wall 520. The cavity 514 preferably includes a bottom surface 524. The package 502 may be any number of conventional commercially available housings of the type, for example, metal, plastic or ceramic. In a preferred embodiment, the package 502 is ceramic in order to optimally provide vacuum sealing of the mass 504 in the package 502.

The mass 504 is preferably resiliently attached to the package 502 by the resilient couplings 508 and electrically coupled to the package 502 by the electrical connections 510. The mass 504 preferably has an approximately rectangular cross-sectional shape. The mass 504 preferably has a passive region 538 on one end and an-active region 540 on the opposite end. In a preferred embodiment, the mass 504 is a micro machined sensor substantially as disclosed in copending U.S. patent application Ser. No. 09/936,640, filed on Sep. 12, 2001, the disclosure of which is incorporated herein by reference.

In a preferred embodiment, the mass 504 includes a top parallel planar surface 526 and a bottom parallel planar surface 528. The bottom parallel planar surface 528 of the mass 504 preferably includes a first side 530, a second side 532, a third side 534, and a fourth side 536. The first side 530 and the third side 534 are preferably approximately parallel to each other and the second side 532 and the fourth side 536 are preferably approximately parallel to each other and preferably approximately perpendicular to the first side 530 and the third side 534.

In a preferred embodiment, the bottom parallel planar surface 528 of the mass 504 includes the bond pads 506. In a preferred embodiment, the bond pads 506 contact area is maximized in order to optimize the shock tolerance of the mass 504. In a preferred embodiment, the bond pads 506 have minimal discontinuities in order to optimize the distribution of thermal stresses in the mass 504. In several alternate embodiments, there is a plurality of bond pads 506 in order to optimize the relief of thermal stresses in the mass 504. In a preferred embodiment, there is a first bond pad 506*a* and a second bond pad 506*b*. In a preferred embodiment, the first bond pad 506*a* is located in the passive region 538 of the bottom parallel planar surface 528 of the mass 504. The first bond pad 506*a* may be located a perpendicular distance ranging, for example, from about 5 to 25 mils from the first side 530 of the bottom parallel planar surface 528 of the mass 504 and may be located a perpendicular distance ranging, for example, from about 5 to 25 mils from the second side 532 of the bottom parallel planar surface 528 of the mass 504. In a preferred embodiment, the first bond pad 506*a* is located a perpendicular distance ranging from about 7 to 12 mils from the first side 530 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

In a preferred embodiment, the second bond pad 506*b* is located in the active region 540 of the bottom parallel planar surface 528 of the mass 504. The second bond pad 506*b* may be located a perpendicular distance ranging, for example, from about 5 to 25 mils from the third side 534 of the bottom parallel planar surface 528 of the mass 504 and may be located a perpendicular distance ranging, for example, from about 5 to 25 mils from the second side 532 of the bottom parallel planar surface 528 of the mass 504. In a preferred embodiment, the second bond pad 506*b* is located a perpendicular distance ranging from about 7 to 12 mils from the third side 534 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

The first bond pad 506*a* may be used for, for example, solder, glass frit, conductive epoxy, or non-conductive epoxy bonding. In a preferred embodiment, the first bond pad 506*a* is used for solder bonding in order to optimally provide good manufacturability. The first bond pad 506*a* preferably has an approximately rectangular cross-sectional shape. The length $L_{506a}$ of the first bond pad 506*a* may range, for example, from about 180 to 240 mils. In a preferred embodiment, the length $L_{506a}$ of the first bond pad 506*a* ranges from about 200 to 220 mils in order to optimally minimize thermal stresses. The width $W_{506a}$ of the first bond pad 506*a* may range, for example, from about 15 to 25 mils. In a preferred embodiment, the width $W_{506a}$ of the first bond pad 506*a* ranges from about 18 to 22 mils in order to optimally minimize thermal stresses. The height $H_{506a}$ of the first bond pad 506a may range, for example, from about 0.1 to 1 microns. In a preferred embodiment, the height $H_{506a}$ of the first bond pad 506a ranges from about 0.24 to 0.72 microns in order to optimally minimize thermal stresses.

The second bond pad 506b may be used for, for example, solder, glass frit, conductive epoxy, or non-conductive epoxy bonding. In a preferred embodiment, the second bond pad 506b is used for solder bonding in order to optimally provide good manufacturability. The second bond pad 506b preferably has an approximately rectangular cross-sectional shape. The length $L_{506b}$ of the second bond pad 506b may range, for example, from about 180 to 240 mils. In a preferred embodiment, the length $L_{506b}$ of the second bond pad 506b ranges from about 200 to 220 mils in order to optimally minimize thermal stresses. The width $W_{506b}$ of the second bond pad 506b may range, for example, from about 15 to 25 mils. In a preferred embodiment, the width $W_{506b}$ of the second bond pad 506b ranges from about 18 to 22 mils in order to optimally minimize thermal stresses. The height $H_{506b}$ of the second bond pad 506b may range, for example, from about 0.1 to 1 microns. In a preferred embodiment, the height $H_{506b}$ of the second bond pad 506b ranges from about 0.24 to 0.72 microns in order to optimally minimize thermal stresses.

The resilient couplings 508 preferably resiliently attach the bond pads 506 to the package 502. In a preferred embodiment, the resilient couplings 508 have minimal discontinuities in order to optimize the distribution of thermal stresses. In several alternate embodiments, there is a plurality of resilient couplings 508 in order to optimize the relief of thermal stresses in the mass 504. In a preferred embodiment, the resilient couplings 508 are solder preforms preferably having an approximately rectangular cross-sectional shape. The resilient couplings 508 may be any number of conventional commercially available solder preforms of the type, for example, eutectic or non-eutectic. In a preferred embodiment, the resilient couplings 508 are a eutectic type in order to optimally provide good yield strength with a reasonable melt temperature. The resilient couplings 508 are preferably coupled to the bottom surface 524 of the cavity 514.

In a preferred embodiment, there is a first resilient coupling 508a and a second resilient coupling 508b. The length $L_{508b}$ of the first resilient coupling 508a may range, for example, from about 200 to 250 mils. In a preferred embodiment, the length $L_{508a}$ of the first resilient coupling 508a ranges from about 225 to 235 mils in order to optimally minimize thermal stresses. The width $W_{508a}$ of the first resilient coupling, 508a may range, for example, from about 20 to 35 mils. In a preferred embodiment, the width $W_{508a}$ of the first resilient coupling 508a ranges from about 25 to 30 mils in order to optimally minimize thermal stresses. The height $H_{508a}$ of the first resilient coupling 508a may range, for example, from about 2 to 4 mils. In a preferred embodiment, the height $H_{508a}$, of the first resilient coupling 508a ranges from about 2.5 to 3 mils in order to optimally minimize thermal stresses.

The length $L_{508b}$ of the second resilient coupling 508b may range, for example, from about 200 to 250 mils. In a preferred embodiment, the length $L_{508b}$ of the second resilient coupling 508b ranges from about 225 to 235 mils in order to optimally minimize thermal stresses. The width $W_{508b}$ of the second resilient coupling 508b may range, for example, from about 20 to 35 mils. In a preferred embodiment, the width $W_{508b}$ of the second resilient coupling 508b ranges from about 25 to 30 mils in order to optimally minimize thermal stresses. The height $H_{508b}$ of the second resilient coupling 508b may range, for example, from about 2 to 4 mils. In a preferred embodiment, the height $H_{508b}$ of the second resilient coupling 508b ranges from about 2.5 to 3 mils in order to optimally minimize thermal stresses.

The first resilient coupling 508a may be located a perpendicular distance ranging, for example, from about 5 to 25 mils from the first wall 516 of the cavity 514 of the package 502 and may be located a perpendicular distance ranging, for example, from 5 to 25 mils from the second wall 518 of the cavity 514 of the package 502. In a preferred embodiment, the first resilient coupling 508a is located a perpendicular distance ranging from about 7 to 12 mils from the first wall 516 of the cavity 514 of the package 502 in order to optimally minimize thermal stresses and located a distance ranging from about 7 to 12 mils from the second wall 518 of the cavity 514 of the package 502 in order to optimally minimize thermal stresses.

The second resilient coupling 508b may be located a perpendicular distance ranging, for example, from about 5 to 25 mils from the third wall 520 of the cavity 514 of the package 502 and may be located a perpendicular distance ranging, for example, from about 5 to 25 mils from the second wall 518 of the cavity 514 of the package 502. In a preferred embodiment, the second resilient coupling 508b is located a perpendicular distance ranging from about 7 to 12 mils from the third wall 520 of the cavity 514 of the package 502 in order to optimally minimize thermal stresses and located a distance ranging from about 7 to 12 mils from the second wall 518 of the cavity 514 of the package 502 in order to optimally minimize thermal stresses.

In a preferred embodiment, the first resilient coupling 508a further includes a first bumper 542 and a second bumper 544 for slidingly supporting the mass 504. In a preferred embodiment, the first bumper 542 of the first resilient coupling 508a is located on one side of the first bond pad 506a and the second bumper 544 of the first resilient coupling 508a is located on another side of the first bond pad 506a. In a preferred embodiment, the first bumper 542 of the first resilient coupling 508a and the second bumper 544 of the first resilient coupling 508a are proximate to the first bond pad 506a. The width $W_{542}$ of the first bumper 542 of the first resilient coupling 508a may range, for example, from about 2 to 6 mils. In a preferred embodiment, the width $W_{542}$ of the first bumper 542 of the first resilient coupling 508a ranges from about 3 to 5 mils in order to optimally minimize thermal stresses. The width $W_{544}$ of the second bumper 544 of the first resilient coupling 508a may range, for example, from about 2 to 6 mils. In a preferred embodiment, the width $W_{544}$ of the second bumper 544 of the first resilient coupling 508a ranges from about 3 to 5 mils in order to optimally minimize thermal stresses.

In a preferred embodiment, the second resilient coupling 508b further includes a first bumper 546 and a second bumper 548 for slidingly supporting the mass 504. In a preferred embodiment, the first bumper 546 of the second resilient coupling 508b is located on one side of the second bond pad 506b and the second bumper 548 of the second resilient coupling 508b is located on another side of the second bond pad 506b. In a preferred embodiment, the first bumper 546 of the second resilient coupling 508b and the second bumper 548 of the second resilient coupling 508b are proximate to the second bond pad 506b. The width $W_{546}$ of the first bumper 546 of the second resilient coupling 508b may range, for example, from about 2 to 6 mils. In a preferred embodiment, the width $W_{546}$ of the first bumper 546 of the second resilient coupling 508b ranges from about 3 to 5 mils in order to optimally minimize thermal stresses. The width $W_{548}$ of the second bumper 548 of the second resilient coupling 508b may range, for example, from about 2 to 6 mils. In a preferred embodiment, the width $W_{548}$ of the second bumper 548 of the second resilient coupling 508b ranges from about 3 to 5 mils in order to optimally minimize thermal stresses. In a preferred embodiment, the resilient couplings 508a and 508b are coupled to the bond pads 506 using conventional solder equipment and processes. In a preferred embodiment, the resilient couplings 508a and 508b are coupled to the bottom surface 524 of the cavity 514 of the package 502 using conventional solder equipment and processes.

The electrical connections 510 preferably electrically couple the mass 504 to the package 502. In a preferred embodiment, there is a single electrical connection 510. The electrical connection 510 preferably electrically couples the top parallel planar surface 512 of the package 502 to the top parallel planar surface 526 of the mass 504. In a preferred embodiment, the electrical connection 512 is a wire bond. The electrical connection 512 may be any number of conventional commercially available wire bonds of the type, for example, gold or aluminum. In a preferred embodiment, the electrical connection 512 is gold in order to optimally provide compatibility to the package 502 and the mass 504 metallization. In a preferred embodiment, the electrical connection 512 is coupled to the package 502 using conventional wire-bonding equipment and processes. In a preferred embodiment, the electrical connection 512 is coupled to the mass 504 using conventional wire-bonding equipment and processes.

Figure 5A:
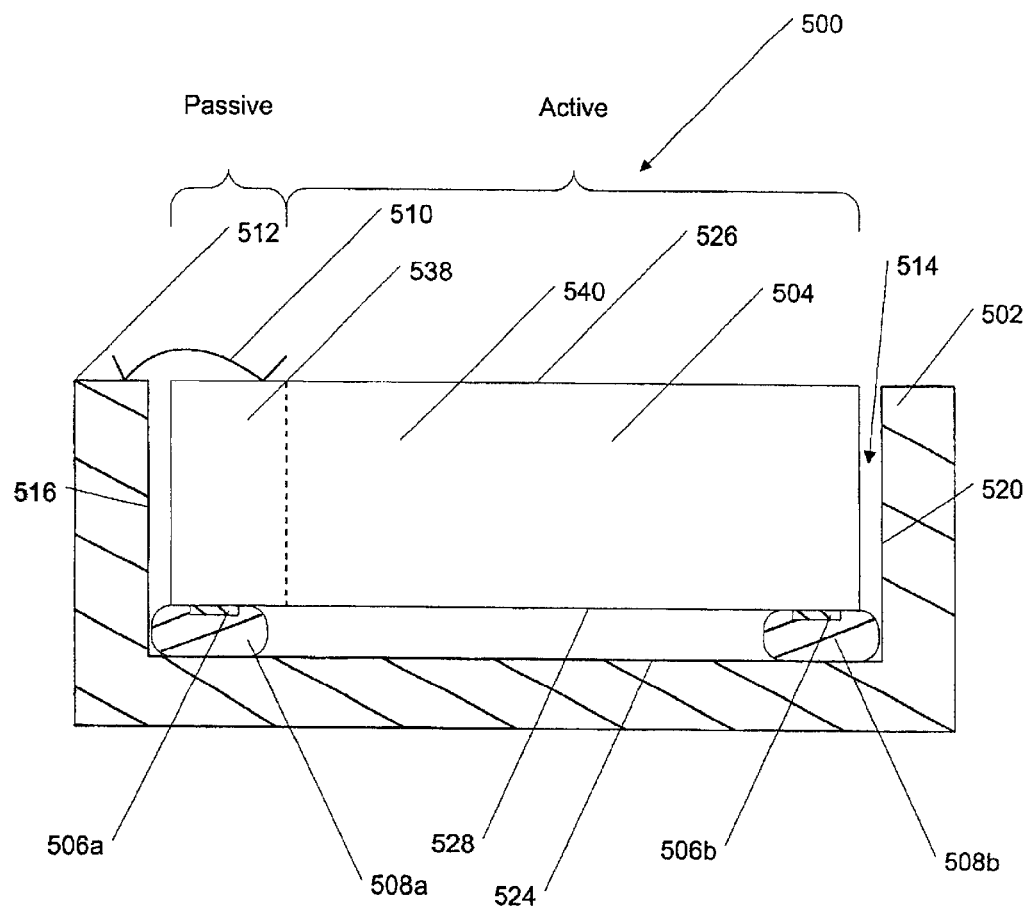
FIG. 5A is a cross-sectional view illustrating an embodiment of an apparatus for resiliently attaching a mass to a package.
Figure 5B:
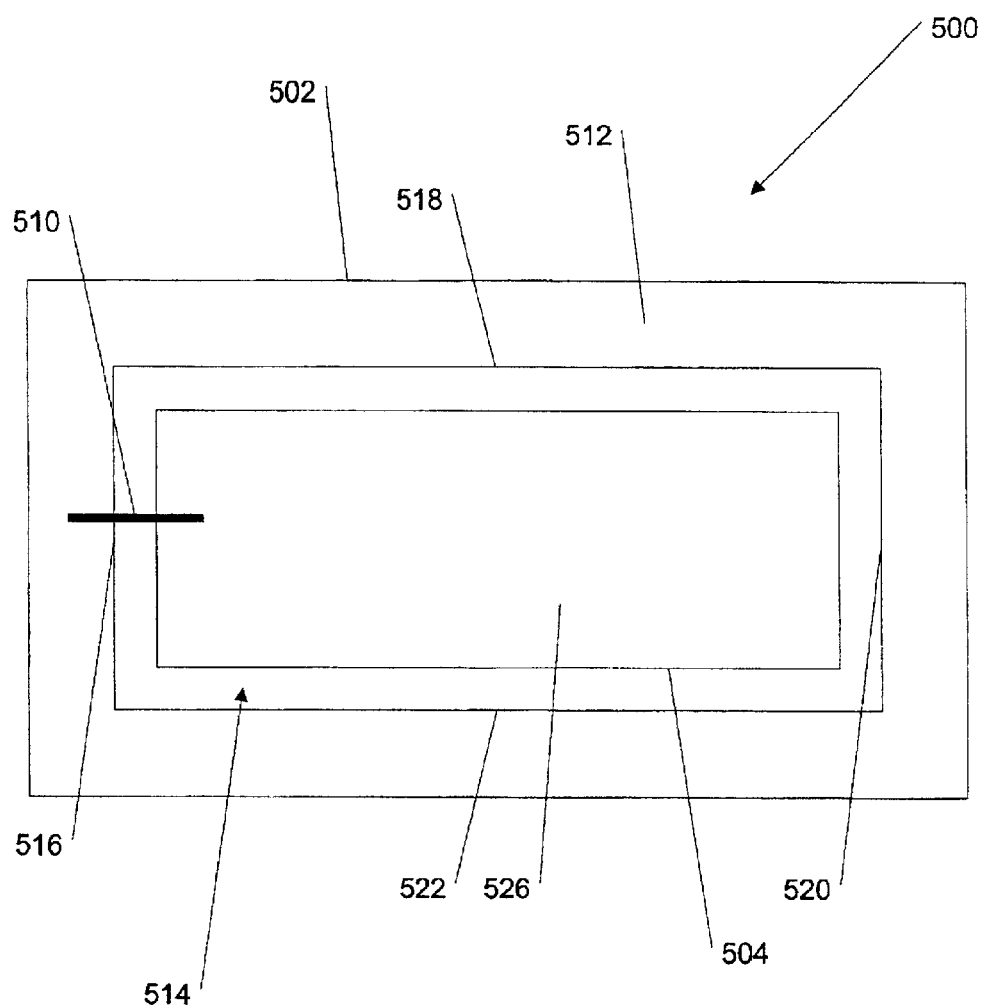
FIG. 5B is a top view of an embodiment of the apparatus of FIG. 5A.
Figure 5C:
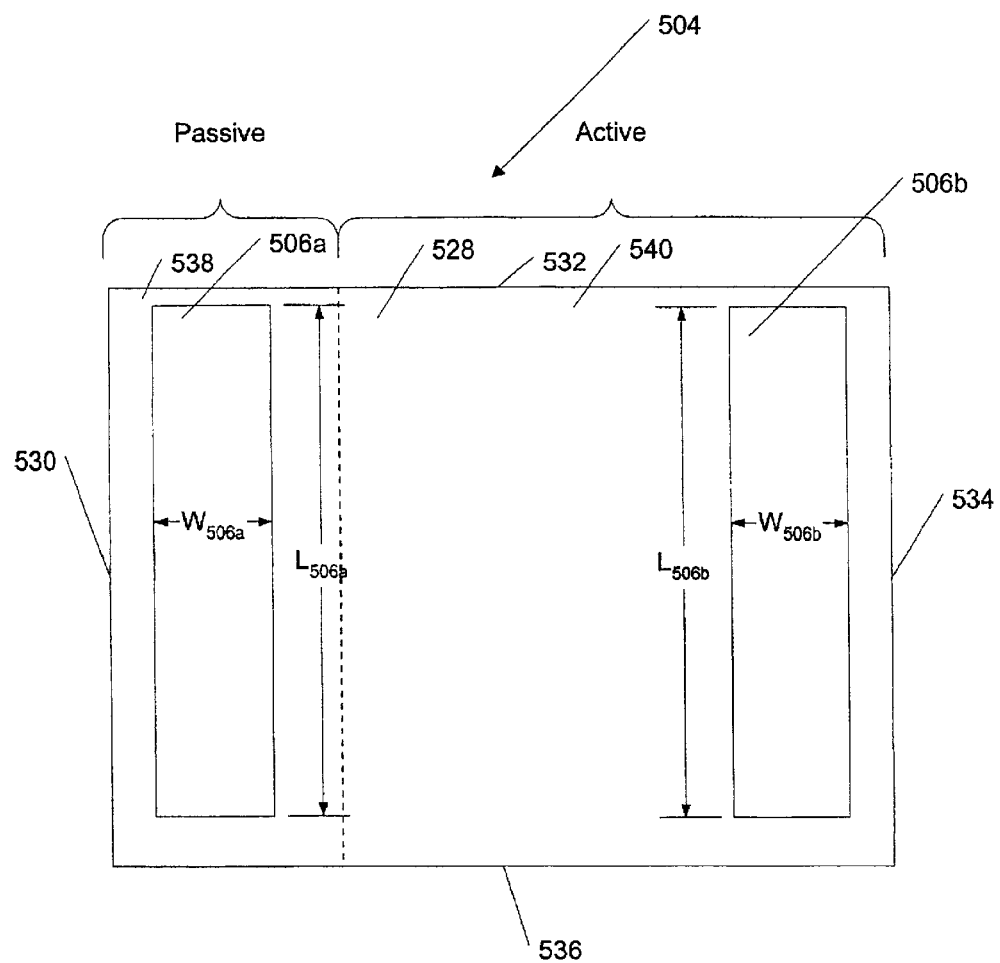
FIG. 5C is a bottom view of an embodiment of the mass of the apparatus of FIG. 5A.
Figure 5D:
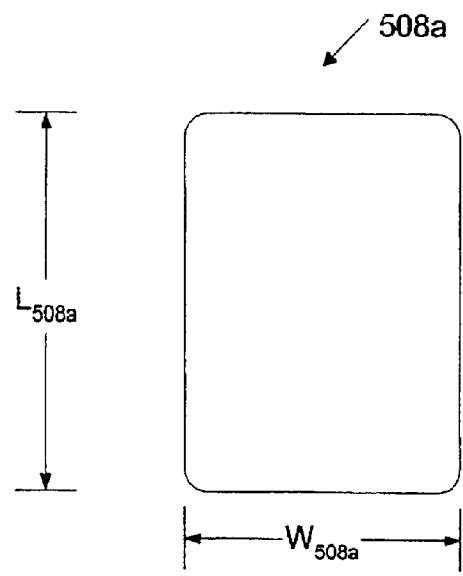
FIG. 5D is a top view of an embodiment of the first resilient coupling of the apparatus of FIG. 5A.
Figure 5E:
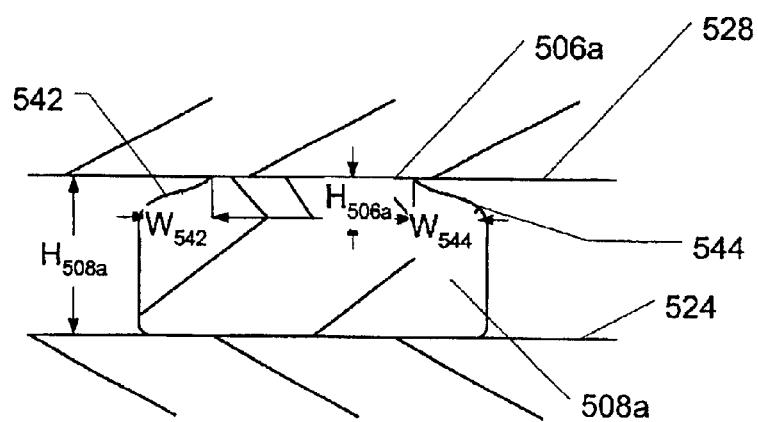
FIG. 5E is a detailed view of the embodiment of the first resilient coupling of FIG. 5D.
Figure 5F:
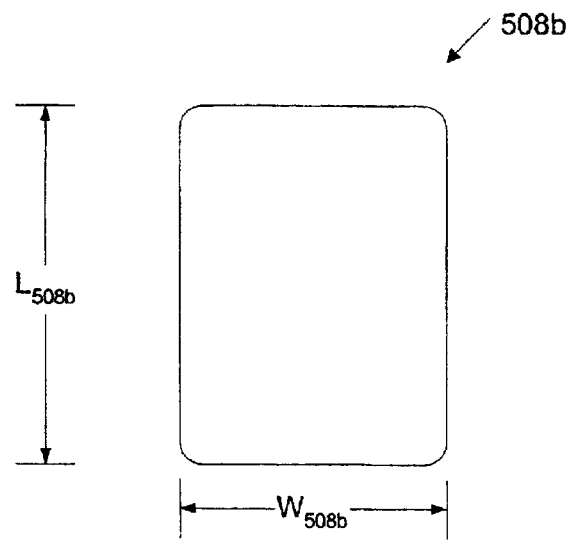
FIG. 5F is a top view of an embodiment of the second resilient coupling of the apparatus of FIG. 5A.
Figure 5G:
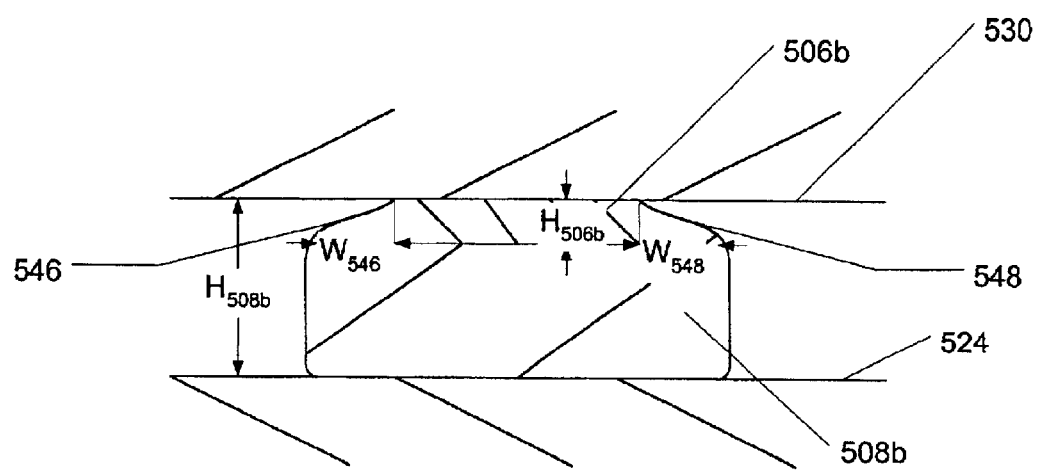
FIG. 5G is a detailed view of the embodiment of the second resilient coupling of FIG. 5F.
Figure 5H:
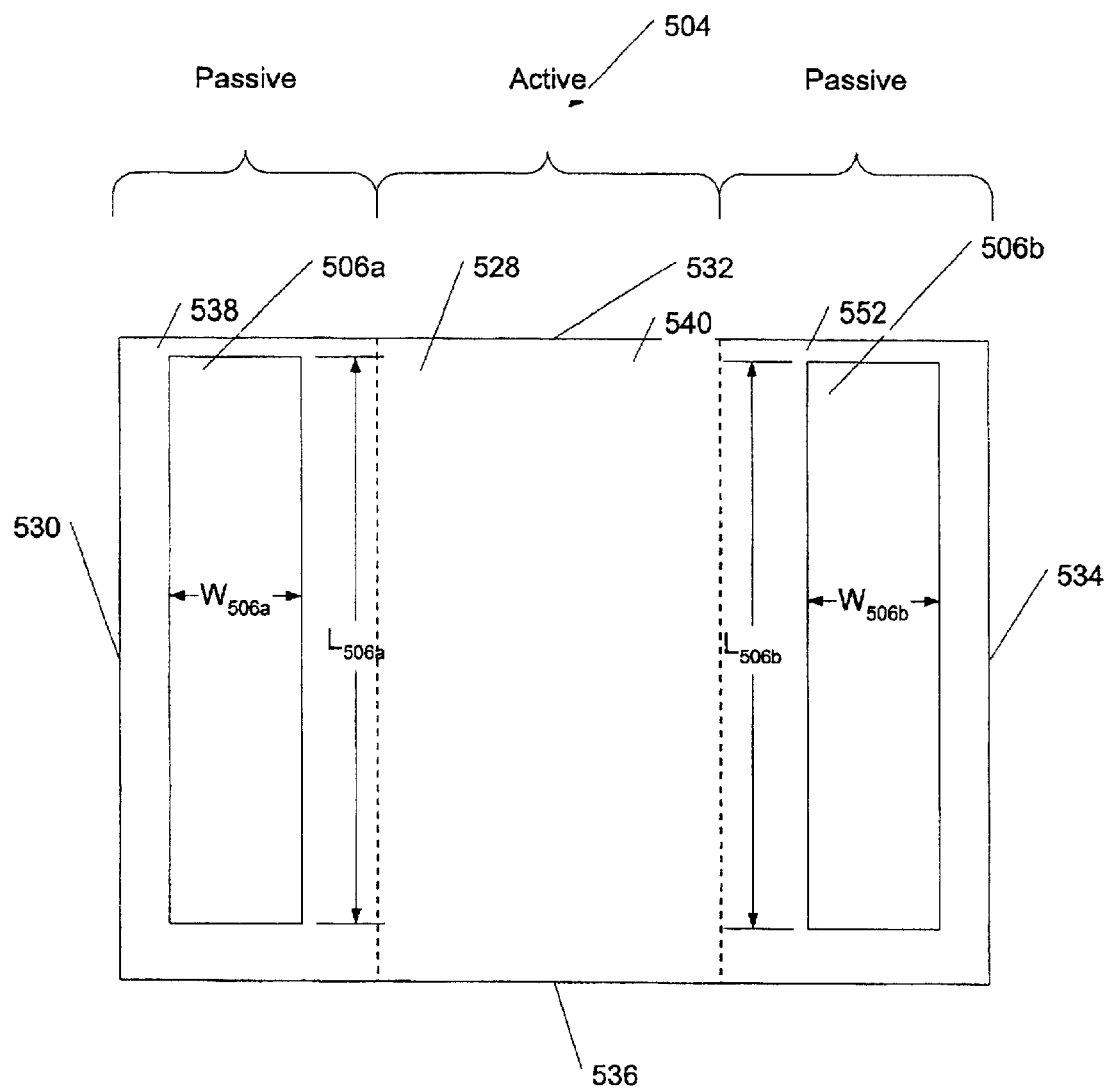
FIG. 5H is a bottom view of an alternate embodiment of the mass of the apparatus of FIG. 5A.

Referring to FIG. 5H, in an alternate embodiment, the mass 504 further includes a second passive region 552 at the opposite end of the bottom parallel planar surface of the mass 504 from the passive region 538. The active region 540 is preferably located between the passive region 538 and the second passive region 552. In a preferred embodiment, the second bond pad 506b is located in the second passive region 552.

Figure 5J:
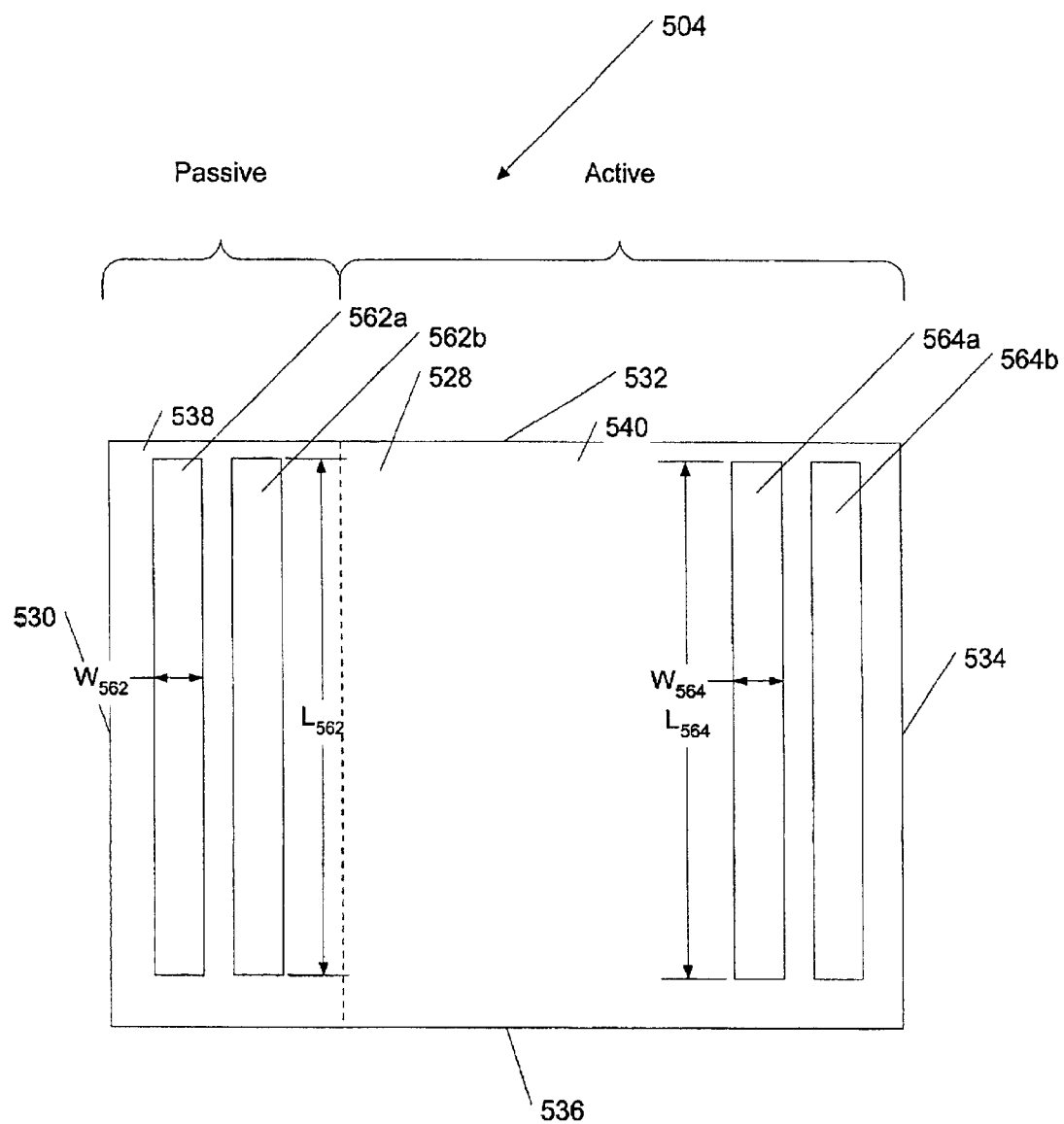
FIG. 5J is a bottom view of an alternate embodiment of the mass of the apparatus of FIG. 5A.

Referring to FIG. 5J, in an alternate embodiment, there are one or more bond pads 562 and one or more bond pads 564. In a preferred embodiment there is a first bond pad 562a and a second bond pad 562b. The bond pads 562a and 562b are substantially equal in size and vertically horizontally proximate to each other. The bond pads 562a and 562b may be used for, for example, solder, glass frit, conductive epoxy, or non-conductive epoxy bonding. In a preferred embodiment, the bond pads 562a and 562b are used for solder bonding in order to provide good manufacturability. The bond pads 562a and 562b preferably have an approximately rectangular cross-sectional shape. The length $L_{562}$ of the bond pads 562a and 562b may range, for example, from about 180 to 240 mils. In a preferred embodiment, the length $L_{562}$ of the bond pads 562a and 562b range from about 200 to 220 mils in order to optimally minimize thermal stresses. The width $W_{562}$ of the bond pads 562a and 562b may range, for example, from about 10 to 20 mils. In a preferred embodiment, the width $W_{562}$ of the bond pads 562a and 562b range from about 13 to 18 mils in order to optimally minimize thermal stresses. The height $H_{502}$ of the bond pads 562a and 562b may range, for example, from about 0.1 to 1 micron. In a preferred embodiment, the height $H_{562}$ of the bond pads 562a and 562b range from about 0.24 to 0.72 microns in order to optimally minimize thermal stresses.

In a preferred embodiment, the first bond pad 562a is preferably located in the passive region 538 the bottom parallel planar surface 528 of the mass 504. The first bond pad 562a may be located a perpendicular distance ranging, for example, from about 5 to 25 mils from the first side 530 of the bottom parallel planar surface 528 of the mass 504 and may be located a perpendicular distance ranging, for example, from about 5 to 25 mils from the second side 532 of the bottom parallel planar surface 530 of the mass 504. The first bond pad 562a is preferably located a perpendicular distance ranging from about 7 to 12 mils from the first side 530 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

In a preferred embodiment, the second bond pad 562b is located in the passive region 538 of the bottom parallel planar surface 528 of the mass 504. The second bond pad 562b may be located a perpendicular distance ranging, for example, from about 15 to 45 mils from the first side 530 of the bottom parallel planar surface 528 of the mass 504 and may be located a perpendicular distance ranging, for example, from about 5 to 25 mils from the second side 532 of the bottom parallel planar surface 528 of the mass 504. The second bond pad 562b is preferably located a perpendicular distance ranging from about 20 to 30 mils from the first side 530 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

In a preferred embodiment, there is a third bond pad 564a and a fourth bond pad 564b. The bond pads 564a and 564b may be used for solder, glass frit, conductive epoxy, or non-conductive epoxy bonding. In a preferred embodiment, the bond pads 564 are used for solder bonding in order to optimally provide good manufacturability. The bond pads 564a and 564b preferably have an approximately rectangular cross-sectional shape. The length $L_s$ of the bond pads 564a and 564b may range, for example, from about 180 to 240 mils. In a preferred embodiment, the length $L_{564}$ of the bond pads 564a and 564b range from about 200 to 220 mils in order to optimally minimize thermal stresses. The width $W_{564}$ of the bond pads 564a and 564b may range, for example, from about 10 to 20 mils. In a preferred embodiment, the width $W_{564}$ of the bond pads 564a and 564b range from about 13 to 18 mils in order to optimally minimize thermal stresses. The height $H_{564}$ of the bond pads 564a and 564b may range, for example, from about 0.1 to 1 micron. In a preferred embodiment, the height $H_{564}$ of the bond pads 564a and 564b range from about 0.24 to 0.72 microns in order to optimally minimize thermal stresses.

In a preferred embodiment, the third bond pad 564a is located in the active region 540 of the bottom parallel planar surface 528 of the mass 504. The third bond pad 564a may be located a perpendicular distance ranging, for example, from about 15 to 45 mils from the third side 534 of the bottom parallel planar surface 528 of the mass 504 and may be located a perpendicular distance ranging, for example, from about 5 to 25 mils from the second side 532 of the bottom parallel planar surface 528 of the mass 504. The third bond pad 564a is preferably located a perpendicular distance ranging from about 20 to 30 mils from the third side 534 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

The fourth bond pad 564b is preferably located in the active region 540 of the bottom parallel planar surface 528 of the mass 504. The fourth bond pad 564b may be located a perpendicular distance ranging, for example, from about 5 to 25 mils from the third side 534 of the bottom parallel planar surface 528 of the mass 504 and may be located a perpendicular distance ranging, for example, from about 5 to 25 mils from the second side 532 of the bottom parallel planar surface 528 of the mass 504. The fourth bond pad 564b is preferably located a perpendicular distance ranging from about 7 to 12 mils from the third side 534 of the bottom parallel planar surface 528 of the mass 504 in order to optimally minimize thermal stresses and located a perpendicular distance ranging from about 7 to 12 mils from the second side 532 of the bottom parallel planar surface 528 of the mass 504 in order to optimally minimize thermal stresses.

In an alternate embodiment, the third bond pad 564a and the fourth bond pad 564b are located in the second passive region 552 of the mass 504.

Referring to FIG. 5K through 5S, in several alternate embodiments, a bond pad 506c, a pair of bond pads 506d and 506e, a bond pad 506f, a bond pad 506g, a pair of bond pads 506h and 506i, a trio of bond pads 506j and 506k and 506l, a bond pad 506m, and a pair of bond pads 506n and 506o may be substantially substituted for each of the bond pads 506a and 506b described above with reference to FIG. 5A.

Figure 5K:
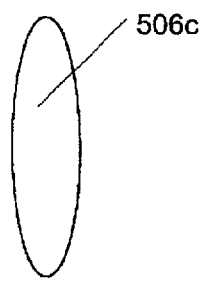
FIG. 5K is a top view of an alternate embodiment of the bond pad of the apparatus of FIG. 5A.

Referring to FIG. 5K, the bond pad 506c may have an approximately oval cross-sectional shape. The bond pad 506c may have an approximate cross-sectional area ranging from about 4000 to 8750 square mils, individually. In a preferred embodiment, the bond pad 506 has an approximate cross-sectional area ranging from about 5625 to 7050 square mils, individually, in order to optimally minimize thermal stresses. The height $H_{506}$ of the bond pad 506c may range, for example, from about 0.1 to 1 micron. In a preferred embodiment, the height $H_{506}$ of the bond pads 506 range from about 0.24 to 0.72 microns in order to optimally minimize thermal stresses.

Figure 5L:
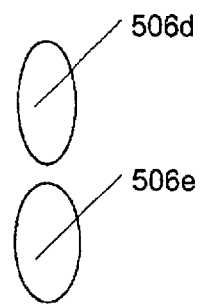
FIG. 5L is a top view of an alternate embodiment of the bond pad of the apparatus of FIG. 5A.

Referring to FIG. 5L, in an alternate embodiment, the bond pads 506d and 506e are substantially equal in size, vertically proximate to each other, and have an approximately oval cross-sectional shape. The bond pads 506d and 506e may have an approximate total cross-sectional area ranging from about 4000 to 8750 square mils. In a preferred embodiment, the bond pads 506d and 506e have an approximate total cross-sectional area ranging from about 5625 to 7050 square mils in order to optimally minimize thermal stresses. The height $H_{506}$ of the bond pads 506d and 506e may range, for example, from about 0.1 to 1 micron. In a preferred embodiment, the height $H_{506}$ of the bond pads 506d and 506e ranges from about 0.24 to 0.72 microns in order to optimally minimize thermal stresses.

Figure 5M:
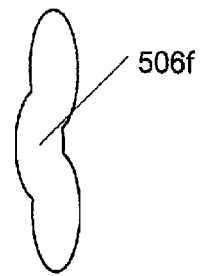
FIG. 5M is a top view of an alternate embodiment of the bond pad of the apparatus of FIG. 5A.

Referring to FIG. 5M, in an alternate embodiment, the bond pad 506f has an approximately tri-oval cross-sectional shape. The bond pad 506f may have approximate cross-sectional area ranging from about 4000 to 8750 square mils. In a preferred embodiment, the bond pad 506f has an approximate cross-sectional area ranging from about 5625 to 8750 square mils in order to optimally minimize thermal stresses. The height $H_{506}$ of the bond pad 506f may range, for example, from about 0.1 to 1 micron. In a preferred embodiment, the height $H_{506}$ of the bond pad 506f ranges from 0.24 to 0.72 microns in order to optimally minimize thermal stresses.

Figure 5N:
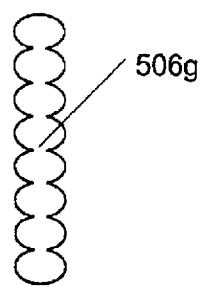
FIG. 5N is a top view of an alternate embodiment of the bond pad of the apparatus of FIG. 5A.

Referring to FIG. 5N, in an alternate embodiment, the bond pad 506g has an approximately oct-oval cross-sectional shape. The bond pad 506g may have an approximate cross-sectional area ranging from about 4000 to 8750 square mils. In a preferred embodiment, the bond pad 506g have an approximate cross-sectional area ranging from about 5625 to 7050 square mils in order to optimally minimize thermal stresses. The height $H_{506}$ of the bond pad 506g may range, for example, from about 0.1 to 1 micron. In a preferred embodiment, the height $H_{506}$ of the bond pad 506g range from about 0.24 to 0.72 microns in order to optimally minimize thermal stresses.

Figure 5P:
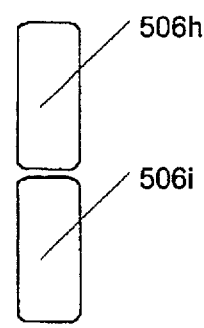
FIG. 5P is a top view of an alternate embodiment of the bond pad of the apparatus of FIG. 5A.

Referring to FIG. 5P, in an alternate embodiment, the bond pads 506h and 506i are substantially equal in size, vertically proximate to each other, and have an approximately rectangular cross-sectional shape. The bond pads 506h and 506i may have an approximate total cross-sectional area ranging from about 4000 to 8750 square mils. In a preferred embodiment, the bond pads 506h and 506i have an approximate total cross-sectional area ranging from about 5625 to 8750 square mils in order to optimally minimize thermal stresses. The height $H_{506}$ of the bond pads 506h and 506i may range, for example, from about 0.1 to 1 micron. In a preferred embodiment, the height $H_{506}$ of the bond pads 506h and 506i range from about 0.24 to 0.72 microns in order to optimally minimize thermal stresses.

Figure 5Q:
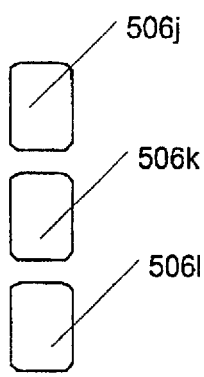
FIG. 5Q is a top view of an alternate embodiment of the bond pad of the apparatus of FIG. 5A.

Referring to FIG. 5Q, in an alternate embodiment, the bond pads 506j, 506k, and 506l are substantially equal in size, vertically proximate to each other, and have an approximately rectangular cross-sectional shape. The bond pads 506j, 506k, and 506l may have an approximate total cross-sectional area ranging from about 4000 to 8750 square mils. In a preferred embodiment, the bond pads 506j, 506k, and 506l have an approximate total cross-sectional area ranging from about 5625 to 8750 square mils in order to optimally minimize thermal stresses. The height $H_{506}$ of the bond pads 506j, 506k, and 506l may range, for example, from about 0.1 to 1 micron. In a preferred embodiment, the height $H_{506}$ of the bond pads 506j, 506k, and 506l range from about 0.24 to 0.72 microns in order to optimally minimize thermal stresses.

Figure 5R:
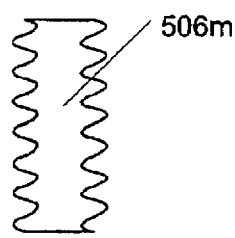
FIG. 5R is a top view of an alternate embodiment of the bond pad of the apparatus of FIG. 5A.

Referring to FIG. 5R in an alternate embodiment, the bond pad 506m may have an approximately wavy sided rectangular cross-sectional shape. The bond pad 506m may have an approximate cross-sectional area ranging from about 4000 to 8750 square mils. In a preferred embodiment, the bond pad 506m have an approximate cross-sectional area ranging from about 5625 to 7050 square mils in order to optimally minimize thermal stresses. The height $H_{506}$ of the bond pad 506m may range, for example, from about 0.1 to 1 microns. In a preferred embodiment, the height $H_{506}$ of the bond pad 506m range from about 0.24 to 0.72 microns in order to optimally minimize thermal stresses.

Figure 5S:
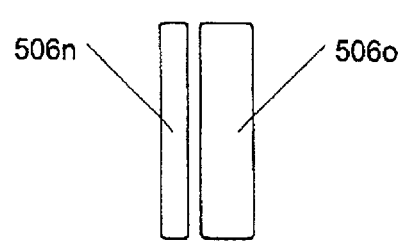
FIG. 5S is a top view of an alternate embodiment of the bond pad of the apparatus of FIG. 5A.
Figure 5T:
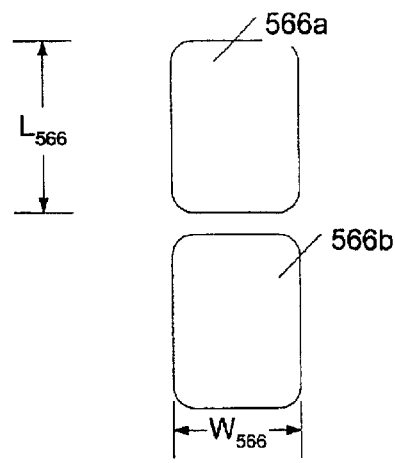
FIG. 5T is a top view of an alternate embodiment of the first resilient coupling of the apparatus of FIG. 5A.
Figure 5U:
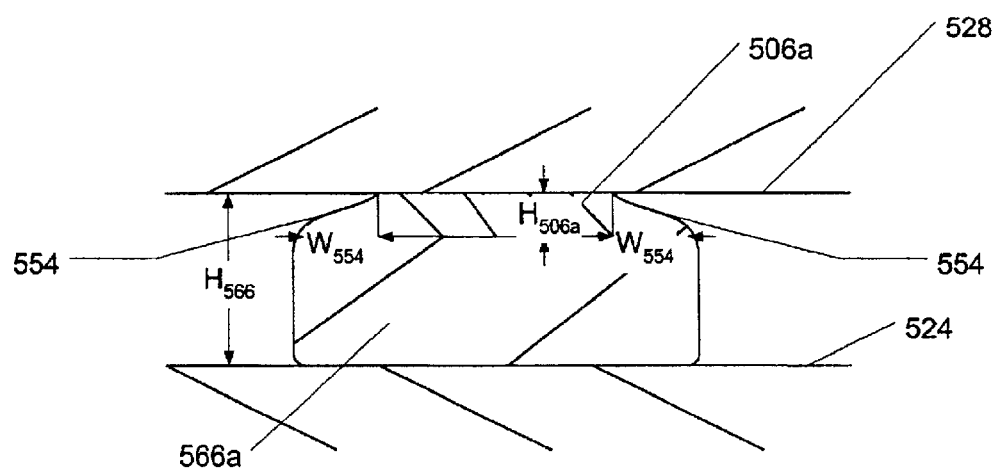
FIG. 5U is a detailed view of the alternate embodiment of the first resilient coupling of FIG. 5T.
Figure 5V:
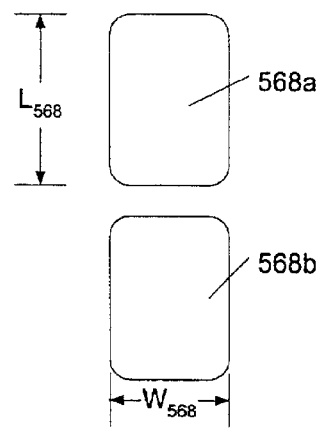
FIG. 5V is a top view of an alternate embodiment of the second resilient coupling of the apparatus of FIG. 5A.
Figure 5W:
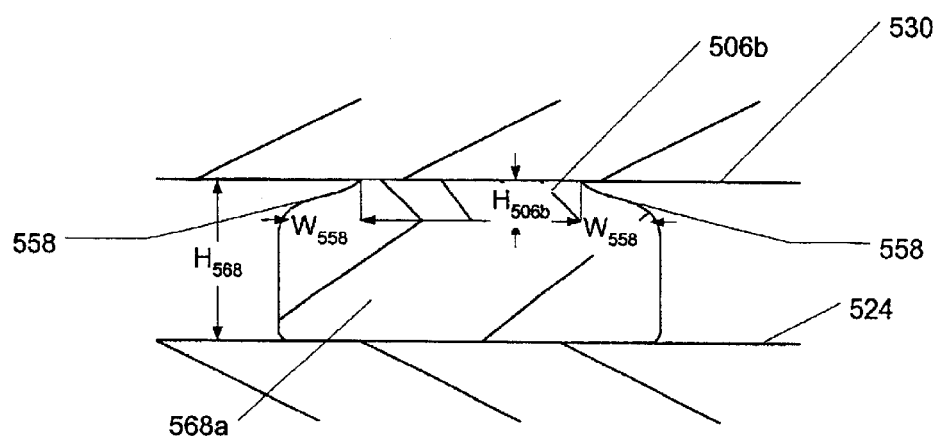
FIG. 5W is a detailed view of the alternate embodiment of the second resilient coupling of FIG. 5V.

Referring to FIG. 5S, in an alternate embodiment, the bond pads 506n and 506o are horizontally proximate to each other and have an approximately rectangular cross-sectional shape. The bond pad 506n is approximately smaller in size than the bond pad 506o. The bond pads 506n and 506o may have an approximate cross-sectional area ranging from about 4000 to 8750 square mils. In a preferred embodiment, the bond pads 506n and 506o have an approximate total cross-sectional area ranging from about 5625 to 7050 square mils in order to optimally minimize thermal stresses. The height $H_{506}$ of the bond pads 506n and 506o may range, for example, from about 0.1 to 1 micron. In a preferred embodiment, the height $H_{506}$ of the bond pads 506n and 506o range from about 0.24 to 0.72 microns in order to optimally minimize thermal stresses.

Referring to FIGS. 5T through 5W, in an alternate embodiment, there are one or more resilient couplings 566 and one or more resilient couplings 568. In a preferred embodiment, the resilient couplings 566 are solder preforms preferably having an approximately rectangular cross-sectional shape. The resilient couplings 566 may be any number of conventional commercially available solder preforms of the type, for example, eutectic or non-eutectic. In a preferred embodiment, the resilient couplings 566 are a eutectic type in order to optimally provide good yield strength with a reasonable melt temperature. The length $L_{566}$ of the resilient couplings 566 may range, for example, from about 90 to 120 mils. In a preferred embodiment, the length $L_{566}$ of the resilient couplings 566 ranges from about 101 to 112 mils in order to optimally minimize thermal stresses. The width $W_{566}$ of the resilient couplings 566 may range, for example, from about 20 to 35 mils. In a preferred embodiment, the width $W_{566}$ of the resilient couplings 566 ranges from about 25 to 30 mils in order to optimally minimize thermal stresses. The height $H_{566}$ of the resilient couplings 566 may range, for example, from about 2 to 4 mils. In a preferred embodiment, the height $H_{566}$ of the resilient couplings 566 ranges from about 2.5 to 3 mils in order to optimally minimize thermal stresses. In a preferred embodiment, the resilient couplings 566 are coupled to the bottom surface 524 of the cavity 514 the package 502 using conventional solder equipment and processes. In a preferred embodiment, the resilient couplings 566 are coupled to the bond pads 506 using conventional solder equipment and processes. In a preferred embodiment, there is a first resilient coupling 566a and a second resilient coupling 566b.

The first resilient coupling 566a be located a perpendicular distance ranging, for example, from about 5 to 25 mils from the first wall 516 the cavity 514 of the package 502 and may be located a perpendicular distance ranging, for example, from about 5 to 25 mils from the second wall 518 of the cavity 514 of the package 502. In a preferred embodiment, the first resilient coupling 566a is located a perpendicular distance ranging from about 7 to 12 mils from the first wall 516 of the cavity 514 of the package 502 in order to optimally minimize thermal stresses and located a distance ranging from about 7 to 12 mils from the second wall 518 of the cavity 514 of the package 502 in order to optimally minimize thermal stresses.

The first resilient coupling 566a further includes one or more first bumpers 554 for slidingly supporting the mass 504. In a preferred embodiment, the first bumpers 554 are located on both sides of the first bond pad 506a. In a preferred embodiment, the first bumpers 554 are proximate to the first bond pad 506a. The width $W_{554}$ of the first bumpers 554 may range, for example, from about 2 to 6 mils. In a preferred embodiment, the width $W_{554}$ of the first bumpers 554 ranges from about 3 to 5 mils in order to optimally minimize thermal stresses.

The second resilient coupling 566b may be located a perpendicular distance ranging, for example, from about 5 to 25 mils from the first wall 516 the cavity 514 of the package 502 and may be located a perpendicular distance ranging, for example, from about 105 to 145 mils from the second wall 518 of the cavity 514 of the package 502. In a preferred embodiment, the second resilient coupling 566b is located a perpendicular distance ranging from about 7 to 12 mils from the first wall 516 of the cavity 514 of the package 502 in order to optimally minimize thermal stresses and located a distance ranging from about 112 to 127 mils from the second wall 518 of the cavity 514 of the package 502 in order to optimally minimize thermal stresses.

The second resilient coupling 566b further includes one or more second bumpers 556 for slidingly supporting the mass 504. In a preferred embodiment, the second bumpers 556 are located on one side of the first bond pad 506a. In a preferred embodiment, the second bumpers 556 are proximate to the first bond pad 506a. The width $W_{556}$ of the second bumpers 556 may range, for example, from about 2 to 6 mils. In a preferred embodiment, the width $W_{556}$, of the second bumpers 556 range from about 3 to 5 mils in order to optimally minimize thermal stresses.

In a preferred embodiment, the resilient couplings 568 are solder preforms preferably having an approximately rectangular cross-sectional shape. The resilient couplings 568 may be any number of conventional commercially available solder preforms of the type, for example, eutectic or non-eutectic. In a preferred embodiment, the resilient couplings 568 are a eutectic type in order to optimally provide good yield strength with a reasonable melt temperature. The length $L_{568}$ of the resilient couplings 568 may range, for example, from about 90 to 120 mils. In a preferred embodiment, the length $L_{568}$ of the resilient couplings 568 ranges from about 101 to 112 mils in order to optimally minimize thermal stresses. The width $W_{568}$ of the resilient couplings 568 may range, for example, from about 20 to 35 mils. In a preferred embodiment, the width $W_{568}$ of the resilient couplings 568 ranges from about 25 to 30 mils in order to optimally minimize thermal stresses. The height $H_{568}$ of the resilient couplings 568 may range, for example, from about 2 to 4 mils. In a preferred embodiment, the height $H_{568}$ of the resilient couplings 568 ranges from about 2.5 to 3 mils in order to optimally minimize thermal stresses. In a preferred embodiment, the resilient couplings 568 are coupled to the bottom surface 524 of the cavity 514 the package 502 using conventional solder equipment and processes. In a preferred embodiment, the resilient couplings 568 are coupled to the bond pads 506 using conventional solder equipment and processes. In a preferred embodiment, there is a third resilient coupling 568a and a fourth resilient coupling 568b.

The third resilient coupling 568a may be located a perpendicular distance ranging, for example, from about 5 to 25 mils from the third wall 520 the cavity 514 of the package 502 and may be located a perpendicular distance ranging, for example, from about 5 to 25 mils from the second wall 518 of the cavity 514 of the package 502. In a preferred embodiment, the third resilient coupling 568a is located a perpendicular distance ranging from about 7 to 12 mils from the third wall 520 of the cavity 514 of the package 502 in order to optimally minimize thermal stresses and located a distance ranging from about 7 to 12 mils from the second wall 518 of the cavity 514 of the package 502 in order to optimally minimize thermal stresses.

The third resilient coupling 568a further includes one or more third bumpers 558 for slidingly supporting the mass 504. In a preferred embodiment, the third bumpers 558 are located on both sides of the second bond pad 506b In a preferred embodiment, the third bumpers 558 are proximate to the second bond pad 506b. The width $W_{558}$ of the third bumpers 558 may range, for example, from about 2 to 6 mils. In a preferred embodiment, the width $W_{558}$ of the third bumpers 558 range from about 3 to 5 mils in order to optimally minimize thermal stresses.

The fourth resilient coupling 568b may be located a perpendicular distance ranging, for example, from about 5 to 25 mils from the third wall 520 the cavity 514 of the package 502 and may be located a perpendicular distance ranging, for example, from about 105 to 145 mils from the second wall 518 of the cavity 514 of the package 502. In a preferred embodiment, the fourth resilient coupling 568b is located a perpendicular distance ranging from about 7 to 12 mils from the third wall 520 of the cavity 514 of the package 502 in order to optimally minimize thermal stresses and located a distance ranging from about 112 to 127 mils from the second wall 518 of the cavity 514 of the package 502 in order to optimally minimize thermal stresses.

The fourth resilient coupling 568b further includes one or more fourth bumpers 560 for slidingly supporting the mass 504. In a preferred embodiment, the fourth bumpers 560 are located on both sides of the second bond pad 506b. In a preferred embodiment, the fourth bumpers 560 are proximate to the second bond pad 506b. The width $W_{560}$ of the fourth bumpers 560 may range, for example, from about 2 to 6 mils. In a preferred embodiment, the width $W_{560}$ of the fourth bumpers 560 ranges from about 3 to 5 mils in order to optimally minimize thermal stresses.

Figure 5X:
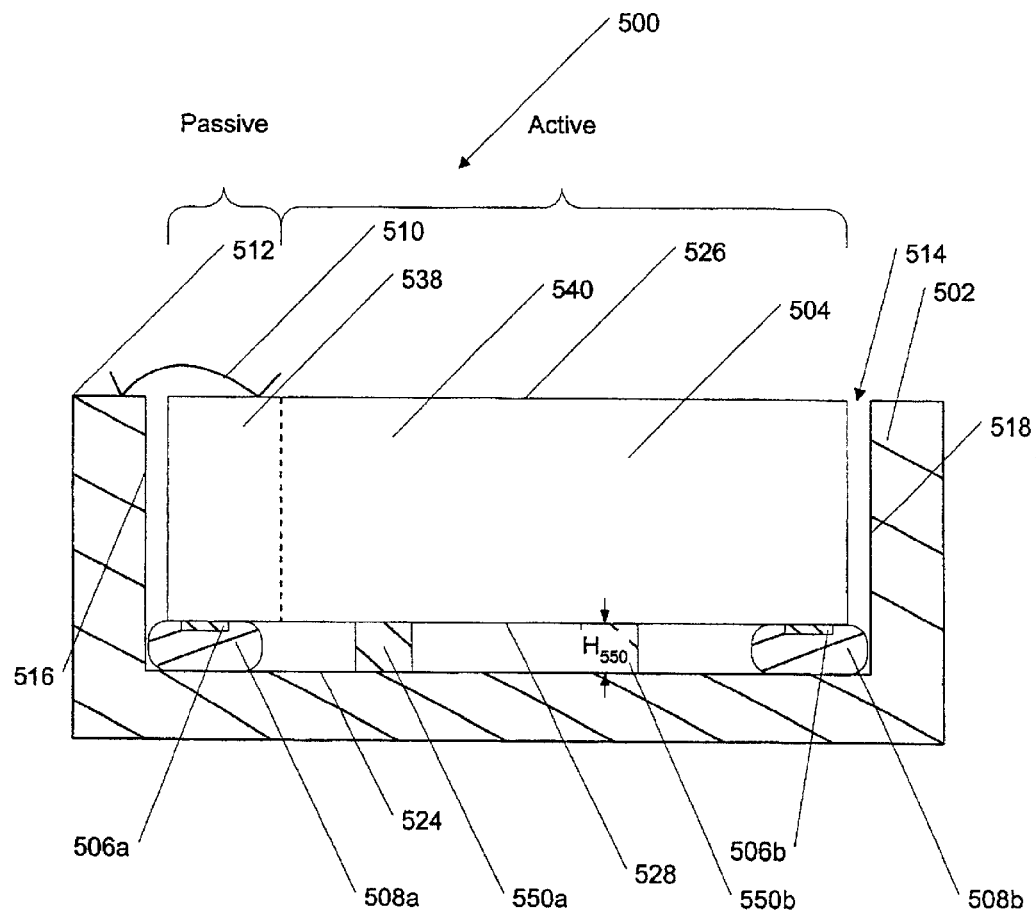
FIG. 5X is a cross-sectional view illustrating an alternate embodiment of an apparatus for resiliently attaching a mass to a package.
Figures 5Y, 5Z:
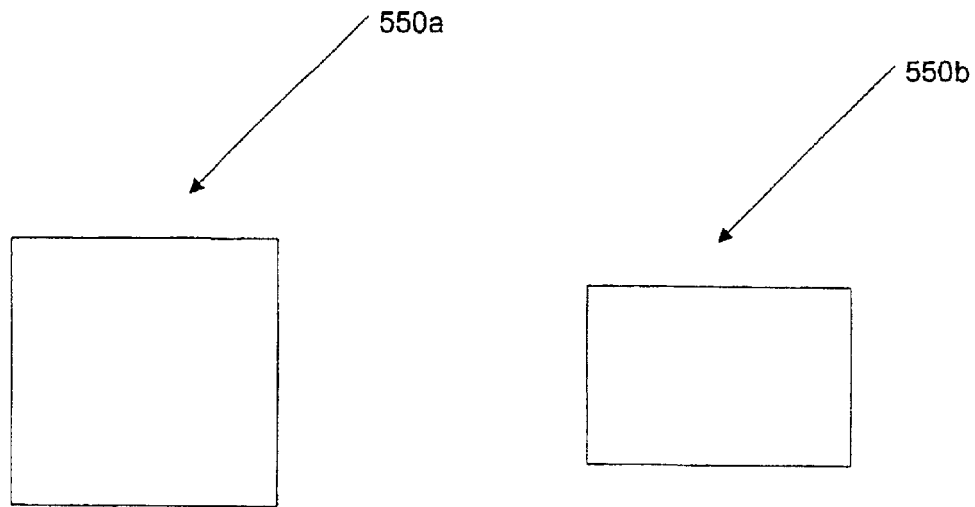
FIG. 5Y is a top view of an embodiment of the sliding supports of the apparatus of FIG. 5X.
FIG. 5Z is a top view of an alternate embodiment of the sliding supports of the apparatus of FIG. 5X.
Figures 5A, 5B:
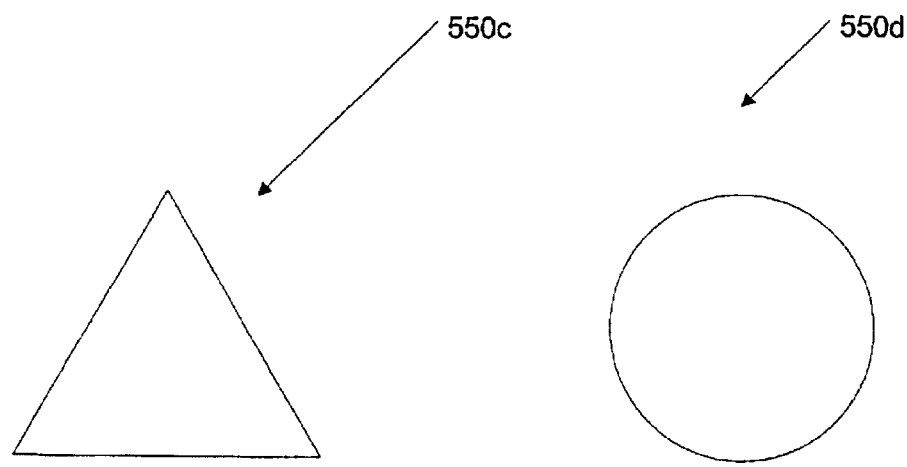

Referring to FIGS. 5X through 5BB, in an alternate embodiment, the system 500 further includes one or more sliding supports 550a, 550b, 550c, or 550d. The sliding supports 550a, 550b, 550c, or 550d preferably slidingly support the mass 504. The sliding supports 550a, 550b, 550c, or 550d are preferably coupled to the bottom surface 524 of the cavity 514 of the package 502. The number of sliding supports 550a, 550b, 550c, or 550d preferably depends upon having a sufficient amount of sliding supports in order to optimally slidingly support the mass 504. The sliding supports 550a may have an approximately square cross sectional shape. The sliding supports 550b may have an approximately rectangular cross sectional shape. The sliding supports 550c may have an approximately triangular cross sectional shape. The sliding supports 550d may have an approximately circular cross sectional shape. The sliding supports 550a, 550b, 550c, or 550d may be, for example, tungsten or ceramic. In a preferred embodiment, the sliding supports 550a, 550b, 550c, or 550d are tungsten in order to optimally provide a standard packaging process. The cross-sectional area of the sliding supports 550a, 550b, 550c, or 550d may range, for example, from about 400 to 1600 square mils, individually. In a preferred embodiment, the cross-sectional area of the sliding supports 550a, 550b, 550c, or 550d may range, for example, from about 625 to 1225 square mils, individually, in order to optimally minimize thermal stresses. The height $H_{550}$ of the sliding supports 550a, 550b, 550c, or 550d may range, for example, from about 0.5 to 3 mils. In a preferred embodiment, the height $H_{550}$ of the sliding supports 550a, 550b, 550c, or 550d ranges from about 1 to 1.5 mils in order to optimally minimize thermal stresses.

In a preferred embodiment, there is a first sliding support 550aa, a second sliding support 550ab, a third sliding support 550ac, and a fourth sliding support 550ad. The first sliding support 550aa may be located a perpendicular distance ranging, for example, from about 45 to 75 mils from the first wall 516 of the cavity 514 of the package 502 and may be located a perpendicular distance ranging, for example, from about 85 to 115 mils from the second wall 518 of the cavity 514 of the package 502. In a preferred embodiment, the first sliding support 550aa is located a perpendicular distance ranging from about 52 to 62 mils from the first wall 516 of the cavity 514 of the package 502 in order to optimally minimize thermal stresses and located a perpendicular distance from about 90 to 105 mils from the second wall 518 of the cavity 514 of the package 502 in order to optimally minimize thermal stresses.

The second sliding support 550ab may be located a perpendicular distance ranging, for example, from about 45 to 75 mils from the first wall 516 of the cavity 514 of the package 502 and may be located a perpendicular distance ranging, for example, from about 15 to 30 mils from the second wall 518 of the cavity 514 of the package 502. In a preferred embodiment, the second sliding support 550ab is located a perpendicular distance ranging from about 52 to 62 mils from the first wall 516 of the cavity 514 of the package 502 in order to optimally minimize thermal stresses and located a perpendicular distance ranging from about 20 to 25 mils from the second wall 518 of the cavity 514 of the package 502 in order to optimally minimize thermal stresses.

The third sliding support 550ac may be located a perpendicular distance ranging, for example, from about 85 to 115 mils from the first wall 516 of the cavity 514 of the package 509 and may be located a perpendicular distance ranging, for example, from about 15 to 30 mils from the second wall 518 of the cavity 514 of the package 502. In a preferred embodiment, the third sliding support 550ac is located a perpendicular distance ranging from about 90 to 105 mils from the first wall 516 of the cavity 514 of the package 502 in order to optimally minimize thermal stresses and located a perpendicular distance ranging from about 20 to 25 mils from the second wall 518 of the cavity 514 of the package 502 in order to optimally minimize thermal stresses.

The fourth sliding support 550ad may be located a perpendicular distance ranging, for example, from about 85 to 115 mils from the first wall 516 of the cavity 514 of the package 502 and may be located a perpendicular distance ranging, for example, from about 85 to 115 mils from the second wall 518 of the cavity 514 of the package 502. In a preferred embodiment, the fourth sliding support 550ad is located a perpendicular distance ranging from about 90 to 105 mils from the first wall 516 of the cavity 514 of the package 502 in order to optimally minimize thermal stresses and located a perpendicular distance ranging from about 90 to 105 mils from the second wall 518 of the cavity 514 of the package 502 in order to optimally minimize thermal stresses.

In an alternate embodiment, the resilient couplings 508 may also electrically couple the mass 504 to the package 502.

In an alternate embodiment, the resilient couplings 566 and 568 may also electrically couple the mass 504 to the package 502.

Referring to FIGS. 6A through 6G, an alternate embodiment of a system 600 for resiliently coupling a mass to a package preferably includes a package 602, a mass 604, one or more bond pads 606, one or more resilient couplings 608, and one or more electrical connections 610.

The package 602 is preferably coupled to the resilient couplings 608 and the electrical connections 610. The package 602 may be, for example, a housing or a substrate. In a preferred embodiment, the package 602 is a housing in order to optimally provide a surface mount component. The package 602 preferably includes a first parallel planar surface 612, a second parallel planar surface 614 and a cavity 616. The cavity 616 preferably includes a first wall 618, a second wall 620, a third wall 622 and a fourth wall 624. The first wall 618 and the third wall 622 are preferably approximately parallel to each other and the second wall 620 and the fourth wall 624 are preferably approximately parallel to each other. The second wall 620 and the fourth wall 624 are also preferably perpendicular to the first wall 618 and the third wall 622. The cavity 616 preferably includes a bottom surface 626. The package 602 may be any number of conventional commercially available housings of the type, for example, metal, ceramic or plastic. In a preferred embodiment, the package 602 is ceramic in order to optimally provide vacuum sealing of the mass 604 in the package 602.

The mass 604 is preferably resiliently attached to the package 602 by the resilient couplings 608 and electrically coupled to the package 602 by the electrical connections 610. The mass 604 preferably has an approximately rectangular cross-sectional shape. The mass 604 preferably includes a passive region 648 on one end and an active region 650 on the opposite end.

In a preferred embodiment, the mass 604 includes a first member 628, a second member 630, and a third member 632. The first member 628 is preferably on top of the second member 630 and the second member 630 is preferably on top of the third member 632. In a preferred embodiment, the first member 628, the second member 630, and the third member 632 are a micro machined sensor substantially as disclosed in copending U.S. patent application Ser. No. 09/936,640, Sep. 12, 2001, the disclosure of which is incorporated herein by reference.

The first member 628 preferably includes one or more parallel planar surfaces. In a preferred embodiment, the first member 628 includes a top parallel planar surface 634. The second member 630 preferably includes one or more parallel planar surfaces. In a preferred embodiment, the second member 630 includes a middle parallel planar surface 636. The third member 632 preferably includes one or more parallel planar surfaces. In a preferred embodiment, the third member 632 includes a bottom parallel planar surface 638. The bottom parallel planar surface 638 of the mass 604 preferably includes a first side 640, a second side 642, a third side 644, and a fourth side 646. The first side 640 and the third side 644 are preferably approximately parallel to each other and the second side 642 and the fourth side 646 are preferably approximately parallel to each other and preferably approximately perpendicular to the first side 640 and the third side 644.

In a preferred embodiment, the bottom parallel planar surface 638 of the mass 604 includes the bond pads 606. In a preferred embodiment, the bond pads 606 contact area is maximized in order to optimize the shock tolerance of the mass 604. In a preferred embodiment, the bond pads 606 have minimal discontinuities in order to optimize the distribution of thermal stresses in the mass 604. In several alternate embodiments, there is a plurality of bond pads 606 in order to optimize the relief of thermal stresses in the mass 604. In a preferred embodiment, there is a first bond pad 606a and a second bond pad 606b. In a preferred embodiment, the first bond pad 606a is located in the passive region 648 of the bottom parallel planar surface 638 of the mass 604. The first bond pad 606a may be located a perpendicular distance ranging, for example, from about 5 to 25 mils from the first side 640 of the bottom parallel planar surface 638 of the mass 604 and may be located a perpendicular distance ranging, for example, from about 5 to 25 mils from the second side 642 of the bottom parallel planar surface 638 of the mass 604. In a preferred embodiment, the first bond pad 606a is located a perpendicular distance ranging from about 7 to 12 mils from the first side 640 of the bottom parallel planar surface 638 of the mass 604 in order to optimally minimize thermal stresses and located a perpendicular distance ranging from about 7 to 12 mils from the second side 642 of the bottom parallel planar surface 638 of the mass 604 in order to optimally minimize thermal stresses.

In a preferred embodiment, the second bond pad 606b is located in the active region 650 of the bottom parallel planar surface 638 of the mass 604. The second bond pad 606b may be located a perpendicular distance ranging, for example, from about 5 to 25 mils from the third side 644 of the bottom parallel planar surface 638 of the mass 604 and may be located a perpendicular distance ranging, for example, from about 5 to 25 mils from the second side 642 of the bottom parallel planar surface 638 of the mass 604. In a preferred embodiment, the second bond pad 606b is located a perpendicular distance ranging from about 7 to 12 mils from the third side 644 of the bottom parallel planar surface 638 of the mass 604 in order to optimally minimize thermal stresses and located a perpendicular distance ranging from about 7 to 12 mils from the second side 642 of the bottom parallel planar surface 638 of the mass 604 in order to optimally minimize thermal stresses.

The first bond pad 606a may be used for, for example, solder, glass frit, conductive epoxy, or non-conductive epoxy bonding. In a preferred embodiment, the first bond pad 606a is used for solder bonding in order to optimally provide good manufacturability. The first bond pad 606a preferably has an approximately rectangular cross-sectional shape. The length $L_{606a}$ of the first bond pad 606a may range, for example, from about 180 to 240 mils. In a preferred embodiment, the length $L_{606a}$ of the first bond pad 606a ranges from about 200 to 220 mils in order to optimally minimize thermal stresses. The width $W_{606A}$ of the first bond pad 606a may range, for example, from about 15 to 25 mils. In a preferred embodiment, the width $W_{606a}$ of the first bond pad 606a ranges from about 18 to 22 mils in order to optimally minimize thermal stresses. The height $H_{606e}$ of the first bond pad 606a may range, for example, from about 0.1 to 1 micron. In a preferred embodiment, the height $H_{606a}$ of the first bond pad 606a ranges from about 0.24 to 0.72 microns in order to optimally minimize thermal stresses.

The second bond pad 606b may, for example, be used for solder, glass frit, conductive epoxy, or non-conductive epoxy bonding. In a preferred embodiment, the second bond pad 606b is used for solder bonding in order to optimally provide solderability. The second bond pad 606b preferably has an approximately rectangular cross-sectional shape. The length $L_{606b}$ of the second bond pad 606b may range, for example, from about 180 to 240 mils. In a preferred embodiment, the length $L_{606b}$ of the second bond pad 606b ranges from about 200 to 220 mils in order to optimally minimize thermal stresses. The width $W_{606b}$ of the second bond pad 606b may range, for example, from about 15 to 25 mils. In a preferred embodiment, the width $W_{606b}$ of the second bond pad 606b ranges from about 18 to 22 mils in order to optimally minimize thermal stresses. The height $H_{506b}$ of the second bond pad 606b may range, for example, from about 0.1 to 1 microns. In a preferred embodiment, the height $H_{606b}$ of the second bond pad 606b ranges from about 0.24 to 0.72 microns in order to optimally minimize thermal stresses.

The resilient couplings 608 preferably resiliently attach the bond pads 606 to the package 602. In a preferred embodiment, the resilient couplings 608 have minimal discontinuities in order to optimize the distribution of thermal stresses. In several alternate embodiments, there is a plurality of resilient couplings 608 in order to optimize the relief of thermal stresses in the mass 604. In a preferred embodiment, the resilient couplings 608 are solder preforms preferably having an approximately rectangular cross-sectional shape. In a preferred embodiment, the resilient couplings 608 are coupled to the bottom surface 626 of the cavity 616. The resilient couplings 608 may be any number of conventional commercially available solder preforms of the type, for example, eutectic or non-eutectic. In a preferred embodiment, the resilient couplings 608 are a eutectic type in order to optimally provide good yield strength with a reasonable melt temperature.

In a preferred embodiment, there is a first resilient coupling 608a and a second resilient coupling 608b. The length $L_{608a}$ of the first resilient coupling 608a may range, for example, from about 200 to 250 mils. In a preferred embodiment, the length $L_{608a}$ of the first resilient coupling 608a ranges from about 225 to 235 mils in order to optimally minimize thermal stresses. The width $W_{608a}$ of the first resilient coupling 608a may range, for example, from about 20 to 35 mils. In a preferred embodiment, the width $W_{606a}$ of the first resilient coupling 608a ranges from about 25 to 30 mils in order to optimally minimize thermal stresses. The height $H_{606a}$ of the first resilient coupling 608a may range, for example, from about 2 to 4 mils. In a preferred embodiment, the height $H_{608a}$ of the first resilient coupling 608a ranges from about 2.5 to 3 mils in order to optimally minimize thermal stresses.

The length $L_{608b}$ of the second resilient coupling 608b may range, for example, from about 200 to 250 mils. In a preferred embodiment, the length $L_{608b}$ of the second resilient coupling 608b ranges from about 225 to 235 mils in order to optimally minimize thermal stresses. The width $W_{608b}$ of the second resilient coupling 608b may range, for example, from about 20 to 35 mils. In a preferred embodiment, the width $W_{608b}$ of the second resilient coupling 608b ranges from about 25 to 30 mils in order to optimally minimize thermal stresses. The height $H_{608b}$ of the second resilient coupling 608b may range, for example, from about 2 to 4 mils. In a preferred embodiment, the height $H_{608b}$ of the second resilient coupling 608b ranges from about 2.5 to 3 mils in order to optimally minimize thermal stresses.

The first resilient coupling 608a may be located a perpendicular distance ranging, for example, from about 5 to 25 mils from the first wall 618 of the cavity 616 of the package 602 and may be located a perpendicular distance ranging, for example, from about 5 to 25 mils from the second wall 620 of the cavity 616 of the package 602. In a preferred embodiment, the first resilient coupling 608a is located a perpendicular distance ranging from about 7 to 12 mils from the first wall 618 of the cavity 616 of the package 602 in order to optimally minimize thermal stresses and located a distance ranging from about 7 to 12 mils from the second wall 620 of the cavity 616 of the package 602 in order to optimally minimize thermal stresses.

The second resilient coupling 608b may be located a perpendicular distance ranging, for example, from about 5 to 25 mils from the third wall 622 of the cavity 616 of the package 602 and may be located a perpendicular distance ranging, for example, from about 5 to 25 mils from the second wall 620 of the cavity 616 of the package 602. In a preferred embodiment, the second resilient coupling 608b is located a perpendicular distance ranging from about 7 to 12 mils from the third wall 622 of the cavity 616 of the package 602 in order to optimally minimize thermal stresses and located a distance ranging from about 7 to 12 mils from the second wall 620 of the cavity 616 of the package 602 in order to optimally minimize thermal stresses.

In a preferred embodiment, the first resilient coupling 608a further includes a first bumper 652 and a second bumper 654 for slidingly supporting the mass 604. In a preferred embodiment, the first bumper 652 of the first resilient coupling 608a is located on one side of the first bond pad 606a and the second bumper 654 of the first resilient coupling 608a is located on another side of the first bond pad 606a. In a preferred embodiment, the first bumper 652 of the first resilient coupling 608a and the second bumper 654 of the first resilient coupling 608a are proximate to the first bond pad 606a. The width $W_{652}$ of the first bumper 652 of the first resilient coupling 608a may range, for example, from about 2 to 6 mils. In a preferred embodiment, the width $W_{652}$ of the first bumper 652 of the first resilient coupling 608a ranges from about 3 to 5 mils in order to optimally minimize thermal stresses. The width $W_{654}$ of the second bumper 654 of the first resilient coupling 608a may range, for example, from about 2 to 6 mils. In a preferred embodiment, the width $W_{654}$ of the second bumper 654 of the first resilient coupling 608a ranges from about 3 to 5 mils in order to optimally minimize thermal stresses.

In a preferred embodiment, the second resilient coupling 608b further includes a first bumper 656 and a second bumper 658 for slidingly supporting the mass 604. In a preferred embodiment, the first bumper 656 of the second resilient coupling 608b is located on one side of the second bond pad 606b and the second bumper 658 of the second resilient coupling 608b is located on another side of the second bond pad 606b. In a preferred embodiment, the first bumper 656 of the second resilient coupling 608b and the second bumper 658 of the second resilient coupling 608b are proximate to the second bond pad 606b. The width $W_{656}$ of the first bumper 656 of the second resilient coupling 608b may range, for example, from about 2 to 6 mils. In a preferred embodiment, the width $W_{656}$ of the first bumper 656 of the second resilient coupling 608b ranges from about 3 to 5 mils in order to optimally minimize thermal stresses. The width $W_{656}$ of the second bumper 658 of the second resilient coupling 608b may range, for example, from about 2 to 6 mils. In a preferred embodiment, the width $W_{658}$ of the second bumper 658 of the second resilient coupling 608b ranges from about 3 to 5 mils in order to optimally minimize thermal stresses. In a preferred embodiment, the resilient couplings 608 are coupled to the bond pads 606 using conventional solder equipment and processes. In a preferred embodiment, the resilient couplings 608 are coupled to the bottom surface 626 of the cavity 616 of the package 602 using conventional solder equipment and processes.

The electrical connections 610 preferably electrically couple the mass 604 to the package 602. In a preferred embodiment, the electrical connections 610 are wire bonds. The electrical connections 610 may be any number of conventional commercially available wire bonds of the type, for example, gold or aluminum. In a preferred embodiment, the electrical connections 610 are gold in order to optimally provide compatibility with the package 602 and the mass 604 metallization. In a preferred embodiment, there is a first electrical connection 610a and a second electrical connection 610b. The first electrical connection 610a preferably electrically couples the first parallel planar surface 612 of the package 602 to the top parallel planar surface 634 of the mass 404. The second electrical connection 610b preferably electrically couples the second parallel planar surface 614 of the package 602 to the middle parallel planar surface 636 of the mass 604. In a preferred embodiment, the electrical connections 610 are coupled to the package 602 using conventional wire-bonding equipment and processes. In a preferred embodiment, the electrical connections 610 are coupled to the mass 604 using conventional wire-bonding equipment and processes.

Referring to FIG. 6H, in an alternate embodiment, the mass 604 further includes a second passive region 662 at the opposite end of the bottom parallel planar surface 638 of the mass 604 from the passive region 648. The active region 650 is preferably located between the passive region 648 and the second passive region 662. In a preferred embodiment, the second bond pad 606b is located in the second passive region 662.

Referring to FIG. 6J, in an alternate embodiment, there are one or more bond pads 672 and one or more bond pads 674. In a preferred embodiment, there is a first bond pad 672a and a second bond pad 672b. The bond pads 672a and 672b are preferably substantially equal and horizontally proximate to each other. The bond pads 672a and 672b may be used for, for example, solder, glass frit, non-conductive epoxy, or conductive epoxy bonding. In a preferred embodiment, the bond pads 672 are used for solder bonding in order to optimally provide good manufacturability. The bond pads 672a and 672b preferably have an approximately rectangular cross-sectional shape. The length $L_{672}$ of the bond pads 672a and 672b may range, for example, from about 180 to 240 mils. In a preferred embodiment, the length $L_{672}$ of the bond pads 672a and 672b range from about 200 to 220 mils in order to optimally minimize thermal stresses. The width $W_{672}$ of the bond pads 672a and 672b may range, for example, from about 10 to 20 mils. In a preferred embodiment, the width $W_{672}$ of the bond pads 672a and 672b range from about 13 to 18 mils in order to optimally minimize thermal stresses. The height $H_{672}$ of the bond pads 672a and 672b may range, for example, from about 0.1 to 1 micron. In a preferred embodiment, the height $H_{672}$ of the bond pad 672a and 672b ranges from about 0.24 to 0.72 microns in order to minimize thermal stresses.

The first bond pad 672a is preferably located in the passive region 648 the bottom parallel planar surface 638 of the mass 604. The first bond pad 672a may be located a perpendicular distance ranging, for example, from about 5 to 25 mils from the first side 640 of the bottom parallel planar surface 638 of the mass 604 and may be located a perpendicular distance ranging, for example, from about 5 to 25 mils from the second side 642 of the bottom parallel planar surface 638 of the mass 604. The first bond pad 672a is preferably located a perpendicular distance ranging from about 7 to 12 mils from the first side 640 of the bottom parallel planar surface 638 of the mass 604 in order to optimally minimize thermal stresses and located a perpendicular distance ranging from about 7 to 12 mils from the second side 642 of the bottom parallel planar surface 638 of the mass 604 in order to optimally minimize thermal stresses.

The second bond pad 672b is preferably located in the passive region 648 of the bottom parallel planar surface 638 of the mass 604. The second bond pad 672b may be located a perpendicular distance ranging, for example, from about 15 to 45 mils from the first side 640 of the bottom parallel planar surface 638 of the mass 604 and may be located a perpendicular distance ranging, for example, from about 5 to 25 mils from the second side 642 of the bottom parallel planar surface 638 of the mass 604. The second bond pad 672b is preferably located a perpendicular distance ranging from about 20 to 30 mils from the first side 640 of the bottom parallel planar surface 638 of the mass 604 in order to optimally minimize thermal stresses and located a perpendicular distance ranging from about 5 to 25 mils from the second side 642 of the bottom parallel planar surface 638 of the mass 604 in order to optimally minimize thermal stresses.

In a preferred embodiment, there is a third bond pad 674a and a fourth bond pad 674b. The bond pads 674a and 674b are preferably substantially equal in size and horizontally proximate to each other. The bond pads 674a and 674b may be used for, for example, solder, glass frit, conductive epoxy, or non-conductive epoxy bonding. In a preferred embodiment, the bond pads 674a and 674b are used for solder bonding in order to optimally provide good manufacturability. The bond pads 674a and 674b preferably have an approximately rectangular cross-sectional shape. The length $L_{674}$ of the bond pads 674a and 674b may range, for example, from about 180 to 240 mils. In a preferred embodiment, the length $L_{674}$ of the bond pads 674a and 674b range from about 200 to 220 mils in order to optimally minimize thermal stresses. The width $W_{674}$ of the bond pads 674a and 674b may range, for example, from about 10 to 20 mils. In a preferred embodiment, the width $W_{674}$ of the bond pads 674a and 674b range from about 13 to 18 mils in order to optimally minimize thermal stresses. The height $H_{674}$ of the bond pads 674a and 674b may range, for example, from about 0.1 to 1 micron. In a preferred embodiment, the height $H_{674}$ of the bond pad 674a and 674b ranges from about 0.24 to 0.72 microns in order to optimally minimize thermal stresses.

The third bond pad 674a is preferably located in the active region 650 of the bottom parallel planar surface 638 of the mass 604. The third bond pad 674a may be located a perpendicular distance ranging, for example, from about 15 to 45 mils from the third side 644 of the bottom parallel planar surface 638 of the mass 604 and may be located a perpendicular distance ranging, for example, from about 5 to 25 mils from the second side 642 of the bottom parallel planar surface 638 of the mass 604. The third bond pad 674a is preferably located a perpendicular distance ranging from about 20 to 30 mils from the third side 644 of the bottom parallel planar surface 638 of the mass 604 in order to optimally minimize thermal stresses and located a perpendicular distance ranging from about 7 to 12 mils from the second side 642 of the bottom parallel planar surface 638 of the mass 604 in order to optimally minimize thermal stresses.

The fourth bond pad 674b is preferably located in the active region 650 of the bottom parallel planar surface 638 of the mass 604. The fourth bond pad 674b may be located a perpendicular distance ranging, for example, from about 5 to 25 mils from the third side 644 of the bottom parallel planar surface 638 of the mass 604 and may be located a perpendicular distance ranging, for example, from about 5 to 25 mils from the second side 642 of the bottom parallel planar surface 638 of the mass 604. The fourth bond pad 674b is preferably located a perpendicular distance ranging from about 7 to 12 mils from the third side 644 of the bottom parallel planar surface 638 of the mass 604 in order to optimally minimize thermal stresses and located a perpendicular distance ranging from about 7 to 12 mils from the second side 642 of the bottom parallel planar surface 638 of the mass 604 in order to optimally minimize thermal stresses.

In an alternate embodiment, the third bond pad 674a and the fourth bond pad 674b are located in the second passive region 662. Referring to FIGS. 6K through 6S, in an alternate embodiment, a bond pad 606c, a pair of bond pads 606*d* and 606*e*, a bond pad 606*f*, a bond pad 606*g*, a pair of bond pads 606*h* and 606*i*, a trio of bond pads 606*j* and 606*k* and 606*l*, a bond pad 606*m*, and a pair of bond pads 606*n* and 606*o* may be substantially substituted for each of the bond pads 606*a* and 606*b* described above with reference to FIG. 6A.

Referring to FIG. 6K, in an alternate embodiment, the bond pad 606*c* may have an approximately oval cross-sectional shape. The bond pad 606*c* may have an approximate cross-sectional area ranging from about 4000 to 8750 square mils, individually. In a preferred embodiment, the bond pad 606*c* have an approximate cross-sectional area ranging from about 5625 to 7050 square mils, individually, in order to optimally minimize thermal stresses. The height $H_{606}$ of the bond pad 606*c* may range, for example, from about 0.1 to 1 micron. In a preferred embodiment, the height $H_{606}$ of the bond pad 606*c* ranges from about 0.24 to 0.72 microns in order to optimally minimize thermal stresses.

Referring to FIG. 6L, in an alternate embodiment, the bond pads 606*e* and 606*d* are substantially equal in size, vertically proximate to each other, and have an approximately oval cross-sectional shape. The bond pads 606*e* and 606*d* may have an approximate total cross-sectional area ranging from about 4000 to 8750 square mils. In a preferred embodiment, the bond pads 606*e* and 606*d* have an approximate total cross-sectional area ranging from about 5625 to 7050 square mils in order to optimally minimize thermal stresses. The height $H_{606}$ of the bond pads 606*e* and 606*d* may range, for example, from about 0.1 to 1 micron. In a preferred embodiment, the height $H_{606}$ of the bond pad 606*e* and 606*d* ranges from about 0.24 to 0.72 microns in order to optimally minimize thermal stresses.

Referring to FIG. 6M, in an alternate embodiment, the bond pad 606*f* has an approximately tri-oval cross-sectional shape. The bond pad 606*f* may have approximate cross-sectional area ranging from about 4000 to 8750 square mils, individually. In a preferred embodiment, the bond pad 606*f* have an approximate cross-sectional area ranging from about 5625 to 7050 square mils, individually, in order to optimally minimize thermal stresses. The height $H_{606}$ of the bond pad 606*f* may range, for example, from about 0.1 to 1 micron. In a preferred embodiment, the height $H_{606}$ of the bond pad 606*f* ranges from about 0.24 to 0.72 microns in order to optimally minimize thermal stresses.

Referring to FIG. 6N, in an alternate embodiment, the bond pad 606*g* has an approximately oct-oval cross-sectional shape. The bond pad 606*g* may have an approximate cross-sectional area ranging from about 4000 to 8750 square mils. In a preferred embodiment, the bond pad 606*g* has an approximate cross-sectional area ranging from about 5625 to 7050 square mils in order to optimally minimize thermal stresses. The height $H_{606}$ of the bond pad 606*g* may range, for example, from about 0.1 to 1 micron. In a preferred embodiment, the height $H_{606}$ of the bond pad 606*g* ranges from about 0.24 to 0.72 microns in order to optimally minimize thermal stresses.

Referring to FIG. 6P, in an alternate embodiment, the bond pads 606*h* and 606*i* are substantially equal in size, vertically proximate to each other, and have an approximately rectangular cross-sectional shape. The bond pads 606*h* and 606*i* may have an approximate total cross-sectional area ranging from about 4000 to 8750 square mils. In a preferred embodiment, the bond pads 606*h* and 606*i* have an approximate total cross-sectional area ranging from about 5625 to 7050 square mils in order to optimally minimize thermal stresses. The height $H_{606}$ of the bond pads 606*h* and 606*i* may range, for example, from about 0.1 to 1 micron. In a preferred embodiment, the height $H_{606}$ of the bond pad 606*h* and 606*i* ranges from about 0.24 to 0.72 microns in order to optimally minimize thermal stresses.

Referring to FIG. 6Q, in an alternate embodiment, the bond pads 606*j* 606*k*, and 606*l* are substantially equal in size, vertically proximate to each other, and have an approximately rectangular cross-sectional shape. The bond pads 606*j* 606*k*, and 606*l* may have an approximate total cross-sectional area ranging from about 4000 to 8750 square mils. In a preferred embodiment, the bond pads 606*j* 606*k*, and 606*l* have an approximate total cross-sectional area ranging from about 5625 to 7050 square mils in order to optimally minimize thermal stresses. The height $H_{606}$ of the bond pads 606*j* 606*k*, and 606*l* may range, for example, from about 0.1 to 1 micron. In a preferred embodiment, the height 606 of the bond pad 606*j* 606*k*, and 606*l* ranges from about 0.24 to 0.72 microns in order to optimally minimize thermal stresses.

Referring to FIG. 6R in an alternate embodiment, the bond pad 606*m* may have an approximately wavy sided rectangular cross-sectional shape. The bond pad 606*m* may have an approximate cross-sectional area ranging from about 4000 to 8750 square mils, individually. In a preferred embodiment, the bond pad 606*m* have an approximate cross-sectional area ranging from about 5625 to 7050 square mils, individually, in order to optimally minimize thermal stresses. The height $H_{606}$ of the bond pad 606*m* may range, for example, from about 0.1 to 1 micron. In a preferred embodiment, the height $H_{606}$ of the bond pad 606*m* ranges from about 0.24 to 0.72 microns in order to optimally minimize thermal stresses.

Referring to FIG. 6S, in an alternate embodiment, the bond pads 606*n* and 606*o* are horizontally proximate to each other and have an approximately rectangular cross-sectional shape. The bond pad 606*n* is approximately smaller in size than the bond pad 606*o*. The bond pads 606*n* and 606*o* may have an approximate total cross-sectional area ranging from about 4000 to 8750 square mils. In a preferred embodiment, the bond pads 606*n* and 606*o* have an approximate total cross-sectional area ranging from about 5625 to 7050 square mils in order to optimally minimize thermal stresses. The height $H_{606}$ of the bond pads 606*n* and 606*o* may range, for example, from about 0.1 to 1 micron. In a preferred embodiment, the height $H_{606}$ of the bond pads 606*n* and 606*o* ranges from about 0.24 to 0.72 microns in order to optimally minimize thermal stresses.

Referring to FIGS. 6T through 6W, in an alternate embodiment, there are one or more resilient couplings 676 and one or more resilient couplings 678. In a preferred embodiment, the resilient couplings 676 are solder preforms preferably having an approximately rectangular cross-sectional shape. The resilient couplings 676 are preferably substantially equal in size and vertically proximate to each other. The resilient couplings 676 may be any number of conventional commercially available solder preforms of the type, for example, eutectic or non-eutectic. In a preferred embodiment, the resilient couplings 676 are a eutectic type in order to optimally provide good yield strength with a reasonable melt temperature. The length $L_{676}$ of the resilient couplings 676 may range, for example, from about 90 to 120 moils. In a preferred embodiment, the length $L_{676}$ of the resilient couplings 676 ranges from about 101 to 112 mils in order to optimally minimize thermal stresses. The width $W_{676}$ of the resilient couplings 676 may range, for example, from about 20 to 35 mils. In a preferred embodiment, the width $W_{676}$ of the resilient couplings 676 ranges from about 25 to 30 mils in order to optimally minimize thermal stresses. The height $H_{676}$ of the resilient couplings 676 may range, for example, from about 2 to 4 mils. In a preferred embodiment, the height $H_{676}$ of the resilient couplings 676 ranges from about 2.5 to 3 mils in order to optimally minimize thermal stresses. In a preferred embodiment, the resilient couplings 676 are coupled to the bottom surface 626 of the cavity 616 the package 602 using conventional solder equipment and processes. In a preferred embodiment, the resilient couplings 676 are coupled to the bond pads 606 using conventional solder equipment and processes. In a preferred embodiment, there is a first resilient coupling 676a and a second resilient coupling 676b.

The first resilient coupling 676a be located a perpendicular distance ranging, for example, from about 5 to 25 mils from the first wall 618 the cavity 616 of the package 602 and may be located a perpendicular distance ranging, for example, from about 5 to 25 mils from the second wall 620 of the cavity 616 of the package 602. In a preferred embodiment, the first resilient coupling 676a is located a perpendicular distance ranging from about 7 to 12 mils from the first wall 618 of the cavity 616 of the package 602 in order to optimally minimize thermal stresses and located a distance ranging from about 7 to 12 mils from the second wall 620 of the cavity 616 of the package 602 in order to optimally minimize thermal stresses.

The first resilient coupling 676a further includes one or more first bumpers 664 for slidingly supporting the mass 604. In a preferred embodiment, the first bumpers 664 are located on both sides of the first bond pad 606a In a preferred embodiment, the first bumpers 664 are proximate to the first bond pad 606a. The width $W_{664}$ of the first bumpers 664 may range, for example, from about 2 to 6 mils. In a preferred embodiment, the width $W_{664}$ of the first bumpers 664 range from about 3 to 5 mils in order to optimally minimize thermal stresses.

The second resilient coupling 676b may be located a perpendicular distance ranging, for example, from about 5 to 25 mils from the first wall 618 the cavity 616 of the package 602 and may be located a perpendicular distance ranging, for example, from about 105 to 145 mils from the second wall 620 of the cavity 616 of the package 602. In a preferred embodiment, the second resilient coupling 676b is located a perpendicular distance ranging from about 7 to 12 mils from the first wall 618 of the cavity 616 of the package 602 in order to optimally minimize thermal stresses and located a distance ranging from about 112 to 127 mils from the second wall 620 of the cavity 616 of the package 602 in order to optimally minimize thermal stresses.

The second resilient coupling 676b further includes one or more second bumpers 666 for slidingly supporting the mass 604. In a preferred embodiment, the second bumpers 666 are located on one side of the first bond pad 606a. In a preferred embodiment, the second bumpers 666 are proximate to the first bond pad 606a. The width $W_{666}$ of the second bumpers 666 may range, for example, from about 2 to 6 mils. In a preferred embodiment, the width $W_{666}$ of the second bumpers 666 range from about 3 to 5 mils in order to optimally minimize thermal stresses.

In a preferred embodiment, the resilient couplings 678 are solder preforms preferably having an approximately rectangular cross-sectional shape. The resilient couplings 678 may be any number of conventional commercially available solder preforms of the type, for example, eutectic or non-eutectic. In a preferred embodiment, the resilient couplings 678 are a eutectic type in order to optimally provide good yield strength with a reasonable melt temperature. The length $L_{678}$ of the resilient couplings 678 may range, for example, from about 90 to 120 mils. In a preferred embodiment, the length $L_{678}$ of the resilient couplings 678 ranges from about 101 to 112 mils in order to optimally minimize thermal stresses. The width $W_{678}$ of the resilient couplings 678 may range, for example, from about 20 to 35 mils. In a preferred embodiment, the width $W_{678}$ of the resilient couplings 676 ranges from about 25 to 30 mils in order to optimally minimize thermal stresses. The height $H_{678}$ of the resilient couplings 678 may range, for example, from about 2 to 4 mils. In a preferred embodiment, the height $H_{678}$ of the resilient couplings 678 ranges from about 2.5 to 3 mils in order to optimally minimize thermal stresses. In a preferred embodiment, the resilient couplings 678 are coupled to the bottom surface 626 of the cavity 616 the package 602 using conventional solder equipment and processes. In a preferred embodiment, the resilient couplings 678 are coupled to the bond pads 606 using conventional solder equipment and processes. In a preferred embodiment, there is a third resilient coupling 678a and a second resilient coupling 678b.

The third resilient coupling 678a may be located a perpendicular distance ranging, for example, from about 5 to 25 mils from the third wall 622 the cavity 616 of the package 602 and may be located a perpendicular distance ranging, for example, from about 5 to 25 mils from the second wall 620 of the cavity 616 of the package 602. In a preferred embodiment, the third resilient coupling 678a is located a perpendicular distance ranging from about 7 to 12 mils from the third wall 622 of the cavity 616 of the package 602 in order to optimally minimize thermal stresses and located a distance ranging from about 7 to 12 mils from the second wall 620 of the cavity 616 of the package 602 in order to optimally minimize thermal stresses.

The third resilient coupling 678a further includes one or more third bumpers 668 for slidingly supporting the mass 604. In a preferred embodiment, the third bumpers 668 are located on both sides of the second bond pad 606b In a preferred embodiment, the third bumpers 668 are proximate to the second bond pad 606b. The width $W_{668}$ of the third bumpers 668 may range, for example, from about 2 to 6 mils. In a preferred embodiment, the width $W_{668}$ of the third bumpers 668 range from about 3 to 5 mils in order to optimally minimize thermal stresses.

The fourth resilient coupling 678b may be located a perpendicular distance ranging, for example, from about 5 to 25 mils from the third wall 622 the cavity 616 of the package 602 and may be located a perpendicular distance ranging, for example, from about 105 to 145 mils from the second wall 620 of the cavity 616 of the package 602. In a preferred embodiment, the fourth resilient coupling 678b is located a perpendicular distance ranging from about 7 to 12 mils from the third wall 622 of the cavity 616 of the package 602 in order to optimally minimize thermal stresses and located a distance ranging from about 112 to 127 mils from the second wall 620 of the cavity 616 of the package 602 in order to optimally minimize thermal stresses.

The fourth resilient coupling 678b further includes one or more fourth bumpers 670 for slidingly supporting the mass 604. In a preferred embodiment, the fourth bumpers 670 are located on one side of the second bond pad 606b. In a preferred embodiment, the fourth bumpers 670 are proximate to the second bond pad 606b. The width $W_{670}$ of the fourth bumpers 670 may range, for example, from about 2 to 6 mils. In a preferred embodiment, the width $W_{670}$ of the fourth bumpers 670 range from about 3 to 5 mils in order to optimally minimize thermal stresses.

Referring to FIGS. 6X through 6BB, in an alternate embodiment, the system 600 further includes one or more sliding supports 660a, 660b, 660c, or 660d. The sliding supports 660a, 660b, 660c, or 660d preferably slidingly support the mass 604. The sliding supports 660a, 660b, 660c, or 660d are preferably coupled to the bottom surface 626 of the cavity 616 of the package 602. The sliding supports 660a may have an approximately square cross sectional shape. The sliding supports 660b may have an approximately rectangular cross sectional shape. The sliding supports 660c may have an approximately triangular cross sectional shape. The sliding supports 660d may have an approximately circular cross sectional shape. The sliding supports 660a, 660b, 660c, or 660d may be, for example, tungsten or ceramic. In a preferred embodiment, the sliding supports 660a, 660b, 660c, or 660d are tungsten order to optimally provide a standard packaging process. The cross-sectional area of one of the sliding supports 660a, 660b, 660c, or 660d may range, for example, from about 400 to 1600 square mils, individually. In a preferred embodiment, the cross-sectional area of the sliding supports 660a, 660b, 660c, or 660d ranges from about 625 to 1225 square mils, individually, in order to optimally minimize thermal stresses. The height $H_{660}$ of the sliding supports 660a, 660b, 660c, or 660d may range, for example, from about 0.5 to 3 mils. In a preferred embodiment, the height $H_{660}$ of the sliding supports 660a, 660b, 660c, or 660d ranges from about 1 to 1.5 mils in order to optimally minimize thermal stresses.

In a preferred embodiment, there is a first sliding support 660aa, a second sliding support 660ab, a third sliding support 660ac, and a fourth sliding support 660ad. The first sliding support 660aa may be located a perpendicular distance ranging, for example, from about 45 to 75 mils from the first wall 618 of the cavity 616 of the package 602 and may be located a perpendicular distance ranging, for example, from about 85 to 115 mils from the second wall 620 of the cavity 616 of the package 602. In a preferred embodiment, the first sliding support 660aa is located a perpendicular distance ranging from about 52 to 62 mils from the first wall 618 of the cavity 616 of the package 602 in order to optimally minimize thermal stresses and located a perpendicular distance from about 90 to 105 mils from the second wall 620 of the cavity 616 of the package 602 in order to optimally minimize thermal stresses.

The second sliding support 660ab may be located a perpendicular distance ranging, for example, from about 45 to 75 mils from the first wall 618 of the cavity 616 of the package 602 and may be located a perpendicular distance ranging, for example, from about 15 to 30 mils from the second wall 620 of the cavity 616 of the package 602. In a preferred embodiment, the second sliding support 660ab is located a perpendicular distance ranging from about 52 to 62 mils from the first wall 618 of the cavity 616 of the package 602 in order to optimally minimize thermal stresses and located a perpendicular distance ranging from about 20 to 25 mils from the second wall 620 of the cavity 616 of the package 602 in order to optimally minimize thermal stresses.

The third sliding support 660ac may be located a perpendicular distance ranging, for example, from about 85 to 115 mils from the first wall 618 of the cavity 616 of the package 602 and may be located a perpendicular distance ranging, for example, from about 15 to 30 mils from the second wall 620 of the cavity 616 of the package 602. In a preferred embodiment, the third sliding support 660ac is located a perpendicular distance ranging from about 90 to 105 mils from the first wall 618 of the cavity 616 of the package 602 in order to optimally minimize thermal stresses and located a perpendicular distance ranging from about 20 to 25 mils from the second wall 620 of the cavity 616 of the package 602 in order to optimally minimize thermal stresses.

The fourth sliding support 660ad may be located a perpendicular distance ranging, for example, from about 85 to 115 mils from the first wall 618 of the cavity 616 of the package 602 and may be located a perpendicular distance ranging, for example, from about 85 to 115 mils from the second wall 620 of the cavity 616 of the package 602. In a preferred embodiment, the fourth sliding support 660ad is located a perpendicular distance ranging from about 90 to 105 mils from the first wall 618 of the cavity 616 of the package 602 in order to optimally minimize thermal stresses and located a perpendicular distance ranging from about 90 to 105 mils from the second wall 620 of the cavity 616 of the package 602 in order to optimally minimize thermal stresses.

In an alternate embodiment, the resilient couplings 608 may also electrically couple the mass 604 to the package 602.

In an alternate embodiment, the resilient couplings 676 and 678 may also electrically couple the mass 604 to the package 602.

Referring to FIGS. 7A through 7D, in several alternate embodiments, the packages 102, 202, 302, 402, 502 and 602 include one or more pedestals 702a or 702b for supporting one or more resilient couplings 108, 150, 208, 260, 308, 363, 408, 470, 508, 566, 568, 608, 676, and 678. The pedestals 702a and 702b may be fabricated from, for example, tungsten or ceramic. In a preferred embodiment, the pedestals 702a and 702b are fabricated from ceramic. The height $H_{702}$ of the pedestals 702a and 702b may range, for example, from about 0 to 10 mils. In a preferred embodiment, the height $H_{702}$ of the pedestals 702a and 702b is approximately 5 mils. The pedestal 702a is preferably a rectangular shaped support pipe. The pedestal 702a preferably has straight edges. In an alternate embodiment, the pedestal 702b is a cylindrical section. The pedestal 702b preferably has tapered sides. In an alternate embodiment, the pedestal 702b has straight sides. In a preferred embodiment, the pedestals 702a and 702b have a shape that optimally minimizes the thermal stresses between the pedestals 702a and 702b and the supported resilient couplings 108, 150, 208, 260, 308, 363, 408, 470, 508, 566, 568, 608, 676, and 678.

In several alternate embodiments, the packages 102, 202, 502, and 602, as described above with reference to FIGS. 1A, 2A, 5A, and 6A, include one or more recesses 326, as described above with reference to FIG. 3G, for receiving one or more resilient couplings 108, 208, 308, 408, 508 and 608, as described above with reference to FIGS. 1A, 2A, 3A, 4A, 5A, and 6A.

In several alternate embodiments, splitting the resilient attachment of the mass 104, 204, 304, 404, 504, and 604, as described above with reference to FIGS. 1A, 2A, 3A, 4A, 5A, and 6A, to the package 102, 202, 302, 402, 502, and 602, as described above with reference to FIGS. 1A, 2A, 3A, 4A, 5A, and 6A, reduces the stress from the attachment.

In several alternate embodiments, the resilient couplings 108, 208, 308, 408, 508 and 608, as described above with reference to FIGS. 1A, 2A, 3A, 4A, 5A, and 6A, are split into one or more pieces by splitting solder preform, conductive epoxy, non-conductive epoxy, or glass frit.

In several alternate embodiments, the bond pads 106, 206, 306, 406, 506, and 606, as described above with reference to FIGS. 1A, 2A, 3A, 4A, 5A, and 6A, are split into one or more pieces by splitting the bond pads 106, 206, 306, 406, 506, and 606, as described above with reference to FIGS. 1A, 2A, 3A, 4A, 5A, and 6A, using any conventional splitting method.

In several alternate embodiments, the mass 104, 204, 304, 404, 504, and 604, as described above with reference to FIGS. 1A, 2A, 3A, 4A, 5A, and 6A, may be a micromachined device, an integrated circuit chip, or an optical device.

Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. An apparatus including thermal stress protection, comprising:
   a package;
   a mass coupled to the package, the mass having a surface, the mass further including an active region, wherein the mass comprises at least one of a micro-machined device, an integrated circuit chip, and an optical device; an
   one or more substantially rigid members for attaching at least one point on the surface to the package to create a resilient coupling between the mass and the package, wherein at least a portion of the active region is spaced apart from the at least one point of attachment.

2. The apparatus of claim 1, wherein the package comprises;
   a package including a cavity for receiving the mass.

3. The apparatus of claim 1, wherein the package comprises:
   a package including a recess for receiving the rigid member.

4. The apparatus of claim 1, wherein the mass comprises one or more bond pads for coupling the mass to the package.

5. The apparatus of claim 4, wherein the bond pads have a cross-sectional shape selected from the group consisting of approximately rectangular, approximately oval, approximately tri-oval, approximately oct-oval, approximately wavy sided rectangular, approximately oct-pie-wedge, approximately hollow oct-pie-wedge, approximately nine-circular, approximately starburst, or approximately sunburst.

6. The apparatus of claim 4, wherein the mass comprises one or more passive regions; and
   wherein the bond pads are approximately located in the passive regions.

7. The apparatus of claim 4, wherein the mass further comprises a first passive region and a second passive region; and
   wherein the bond pads are located in the first passive region and the second passive region.

8. The apparatus of claim 7, wherein the first passive region is located at one end of the mass; and
   wherein the second passive region is located at the opposite end of the mass.

9. The apparatus of claim 4, wherein the mass further comprises a first passive region integral to the active region; and
   wherein the bond pads are located in the first passive region.

10. The apparatus of claim 9, wherein the first passive region is located at one end of the mass; and
    wherein the active region is located at the opposite end of the mass.

11. The apparatus of claim 4, wherein the bond pads are approximately located in the active region.

12. The apparatus of claim 11, wherein the bond pads are located in the approximate center of the active region.

13. The apparatus of claim 1 wherein the mass includes a passive region located at one end of the mass.

14. The apparatus of claim 1, wherein the rigid members further electrically couple the mass to the package.

15. The apparatus of 1, wherein the rigid members have a cross-sectional shape that is approximately rectangular or approximately circular.

16. The apparatus of claim 1, wherein the rigid members are approximately located at one end of the package.

17. The apparatus of claim 1, wherein the rigid members are approximately located at the approximate center of the package.

18. The apparatus of claim 1, wherein there are one or more first rigid members and one or more second rigid members;
    wherein the first rigid members are approximately located at one end of the package; and
    wherein the second rigid members are approximately located at the opposite end of the package.

19. The apparatus of claim 1, wherein the rigid members are a material selected from the group consisting of solder, conductive epoxy, non-conductive epoxy, and glass frit.

20. The apparatus of claim 1, further comprising one or more sliding supports coupled to the package for slidingly supporting the mass.

21. The apparatus of claim 20, wherein the sliding supports have a cross-sectional shape selected from the group consisting of approximate square, approximate circle, approximate triangle and approximate rectangle.

22. The apparatus of claim 1, wherein the package comprises:
    a package including a pedestal for supporting the rigid members.

23. An apparatus including thermal stress protection, comprising:
    a package;
    a mass coupled to the package, the mass having a surface, the mass further including an active region and a passive region, wherein the mass comprises at least one of a micro-machined device, an integrated circuit chip, and an optical device; and
    one or more substantially rigid members for attaching at least one point on the surface to the package to create a resilient coupling between the mass and the package, wherein the at least one point of attachment is in the passive region and at least a portion of the active region is spaced apart from the at least one point of attachment.

24. A method of coupling a mass having an active region and a passive region to a package to reduce effects of thermal stress, wherein the mass comprises at least one of a micro-machined device, an integrated circuit chip, and an optical device, the method comprising:
    attaching at least one surface point on the mass to the package using one or more substantially rigid members to create a resilient coupling between the mass and the package, wherein the at least one point of attachment is in the passive region and at least a portion of the active region is spaced apart from the at least one point of attachment.

25. A method of coupling a mass having an active region to a package to reduce effects of thermal stress, wherein the mass comprises at least one of a micro-machined device, an integrated circuit chip, and an optical device, the method comprising:

attaching at least one surface point on the mass to the package using one or more substantially rigid members to create a resilient coupling between the mass and the package, wherein at least a portion of the active region is spaced apart from the at least one point of attachment.

26. The method of claim 25, wherein attaching the mass comprises attaching the mass at a plurality of locations.

27. The method of claim 25, wherein the mass comprises a passive region, and wherein attaching the mass comprises attaching the passive region to the package.

28. The method of claim 27, wherein the passive region is located at one end of the mass.

29. The method of claim 25, wherein attaching the mass comprises attaching the active region to the package.

30. The method of claim 29, wherein attaching the active region comprises attaching the approximate center of the active region to the package.

31. The method of claim 25, wherein the mass comprises a first passive region and a second passive region; and wherein attaching the mass comprises attaching the first passive region to the package and attaching the second passive region to the package.

32. The method of claim 31, wherein the first passive region is located at one end of the mass; and wherein the second passive region is located at an opposite end of the mass.

33. The method of claim 25, wherein the mass further comprises a passive region integral to the active region; and wherein attaching the mass comprises attaching the passive region to the package.

34. The method of claim 33, wherein the passive region is at one end of the mass; and wherein the active region is at the opposite end of the mass.

35. The method of claim 25, wherein attaching the mass comprises permitting the mass to expand and contract without inducing stresses in the mass.

36. The method of claim 25, wherein attaching the mass comprises providing for expansion and contraction of the package without inducing stresses in the mass.

37. The method of claim 25, further comprising slidingly supporting the mass at one or more different locations.

38. The method of claim 37, wherein slidingly supporting the mass comprises slidingly supporting the mass at a plurality of locations.

39. The method of claim 37, wherein slidingly supporting the mass comprises providing for expansion and contraction without inducing stresses in the package.

40. The method of claim 25, wherein attaching the mass comprises providing for expansion and contraction without inducing stresses in the package.

41. The method of claim 25, further comprising electrically coupling the mass to the package at one or more different locations.

* * * * *